(12) United States Patent
Benhar et al.

(10) Patent No.: US 8,329,183 B2
(45) Date of Patent: Dec. 11, 2012

(54) RECOMBINANT FUSION PROTEIN AND POLYNUCLEOTIDE CONSTRUCT FOR IMMUNOTOXIN PRODUCTION

(75) Inventors: Itai Benhar, Rehovat (IL); Yariv Mazor, Ra'anana (IL)

(73) Assignee: Ramot at Tel-Aviv University Ltd., Tel Aviv (IL)

( * ) Notice: Subject to any disclaimer, the term of this patent is extended or adjusted under 35 U.S.C. 154(b) by 0 days.

(21) Appl. No.: 13/233,718

(22) Filed: Sep. 15, 2011

(65) Prior Publication Data

US 2012/0003223 A1 Jan. 5, 2012

Related U.S. Application Data

(62) Division of application No. 12/117,494, filed on May 8, 2008, now Pat. No. 8,043,621.

(60) Provisional application No. 60/917,160, filed on May 10, 2007.

(51) Int. Cl.
*A61K 39/104* (2006.01)
(52) U.S. Cl. .................................................. 424/183.1
(58) Field of Classification Search .................. None
See application file for complete search history.

(56) References Cited

U.S. PATENT DOCUMENTS

| | | | | |
|---|---|---|---|---|
| 4,545,985 | A | 10/1985 | Pastan et al. | 424/180.1 |
| 5,602,095 | A | 2/1997 | Pastan et al. | 424/780 |
| 5,608,039 | A | 3/1997 | Pastan et al. | 530/387.3 |
| 5,917,026 | A | 6/1999 | Lowenadler et al. | 536/23.4 |
| 6,051,405 | A | 4/2000 | FitzGerald et al. | 435/69.7 |

FOREIGN PATENT DOCUMENTS

WO WO 99/64073 A2 12/1999

OTHER PUBLICATIONS

Mazor et al. (Cancer Letters, 257:124-135, 2007).*
Bowie et al., "Deciphering the Message in Protein Sequences: Tolerance to Amino Acid Substitutions," Science, 247:1306-1310 (1990).
Braisted et al., "Minimizing a binding domain from protein A," Proc. Natl. Acad. Sci. USA, 93:5688-5692 (1996).
Brinkmann et al., "B3($F_v$)-PE38KDEL, a single-chain immunotoxin that causes complete regression of a human carcinoma in mice," Proc. Natl. Acad. Sci. USA, 88:8616-8620 (1991).
Jendeberg et al., "Kinetic Analysis of the Interaction Between Protein A Domain Variants and Human Fc Using Plasmon Resonance Detection," Journal of Molecular Recognition, 8:270-278 (1995).
Kreitman et al., "Importance of the glutamate residue of KDEL in increasing the cytotoxicity of *Pseudomonas* exotoxin derivatives and for increased binding to the KDEL receptor," Biochem. J., 307:29-37 (1995).
Kufer et al., "A revival of bispecific antibodies," TRENDS in Biotechnology, 22(5):238-224 (2004).
Madshus et al., "Entry of Diphtheria Toxin-Protein A Chimeras into Cells," The Journal of Biological Chemistry, 266(26):17446-17453 (1991).
Mazor et al., "Antibody internalization studied using a novel IgG binding toxin fusion," Journal of Immunological Methods, 321:41-59 (2007).
Nilsson et al., "A synthetic IgG-binding domain based on staphylococcal protein A," Protein Engineering, 1(2):107-113 (1987).
Pini et al., "Phage Display of Antibody Fragments," Current Protein and Peptide Science, 1:155-169 (2000).
Rondahl et al., "Fusions to the 5" end of a gene encoding a two-domain analogue of staphylococcal protein A," Journal of Biotechnology, 25:269-287 (1992).
Siegall et al., "Functional Analysis of Domains II, Ib, and III of *Pseudomonas* Exotoxin," The Journal of Biological Chemistry, 264(24):14256-14261 (1989).
Tonevitskii et al., "Cytotoxic Properties of a Recombinant Hybrid of Protein A from *Staphylococcus aureus* with a Fragment of the *Pseudomonas aeruginosa* Exotoxin A," Mol. Biol. (Mosk), 25:1188-1196 (1991).
Van Esch et al., "Human IgG Fc-binding phage antibodies constructed from synovial fluid $CD38^+B$ cells of patients with rheumatoid arthritis show the imprints of an antigen-dependent process of somatic hypermutation and clonal selection," Clin Exp Immunol, 131:364-376 (2003).
Zdanovskii et al., Molekuliarnaia Genetika, Mikrobiologiia I Virusolog, 7:27-32 (1990).
Zdanovskii et al., Molekuliarnaia Genetika, Mikrobiologiia I Virusolog, 7:27-32 (1990), translation from Russian.
Hakim R, Benhar I., "Inclonals: IgGs and IgG-enzyme fusion proteins produced in an *E. coli* expression-refolding system", MAbs. May-Jun. 2009;1(3):281-287. Epub May 19, 2009.
Pichinuk E, Benhar I, Jacobi O, Chalik M, Weiss L, Ziv R, Sympson C, Karwa A, Smorodinsky NI, Rubinstein DB, Wreschner DH, "Antibody targeting of cell-bound MUC1 SEA domain kills tumor cells", Cancer Res., Apr. 17, 2012.
Shapira S, Shapira A, Starr A, Kazanov D, Kraus S, Benhar I, Arber N., "An immunoconjugate of anti-CD24 and Pseudomonas exotoxin selectively kills human colorectal tumors in mice", Gastroenterology, Mar. 2011;140(3):935-46. Epub Dec. 11, 2010.

\* cited by examiner

*Primary Examiner* — Brian J Gangle
(74) *Attorney, Agent, or Firm* — Rodney J. Fuller; Booth Udall, PLC

(57) ABSTRACT

The present invention relates to a polynucleotide construct encoding a fusion protein consisting of a domain which binds the immunoglobulin Fc region, genetically fused to a truncated form of *Pseudomonas* exotoxin A (PE). In particular, the invention discloses the fusion protein, ZZ-PE38, and further provides immunotoxins, formed from complexes of the fusion protein with antibodies for targeted cell killing.

20 Claims, 28 Drawing Sheets

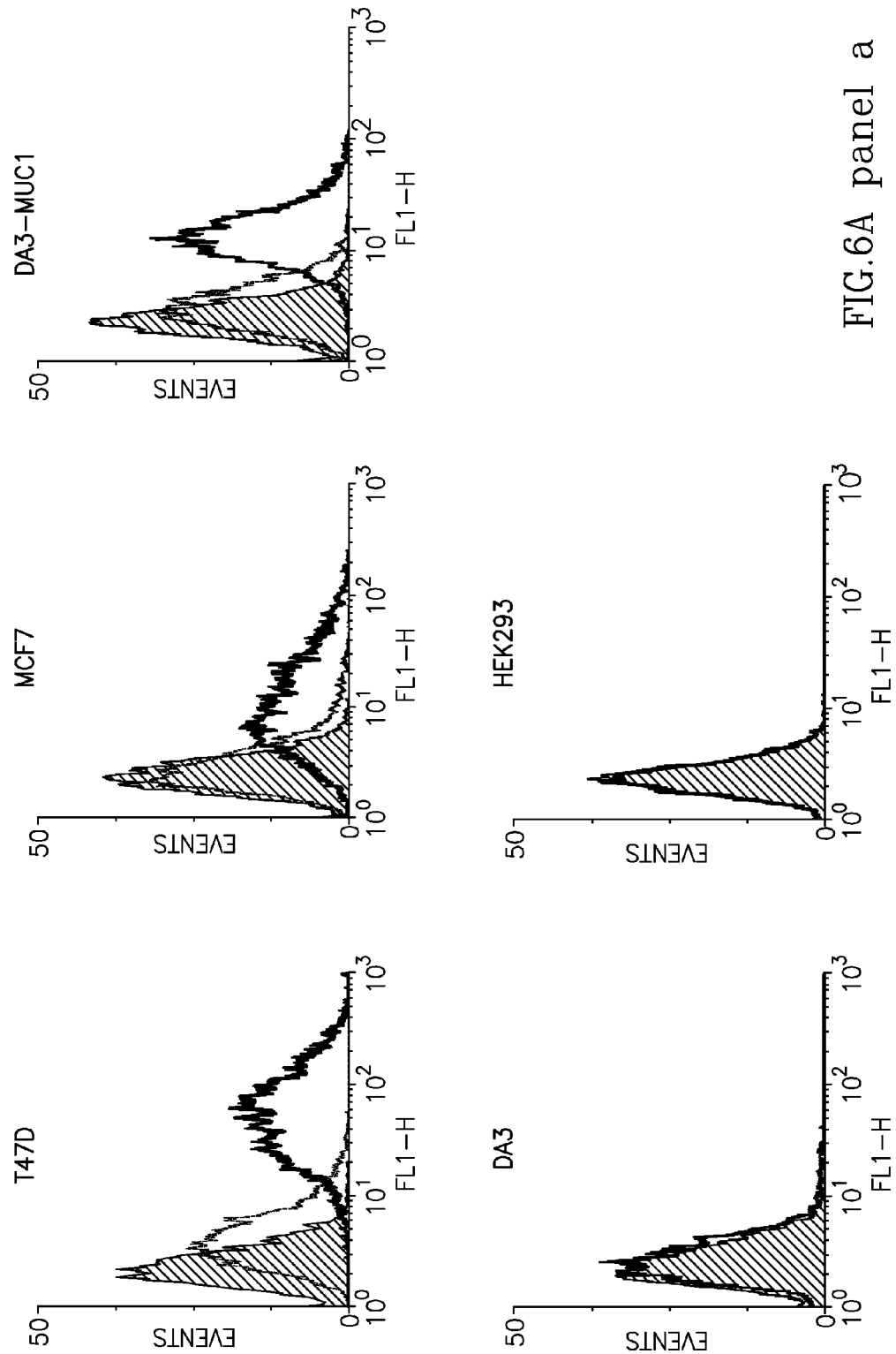
FIG.6A panel a

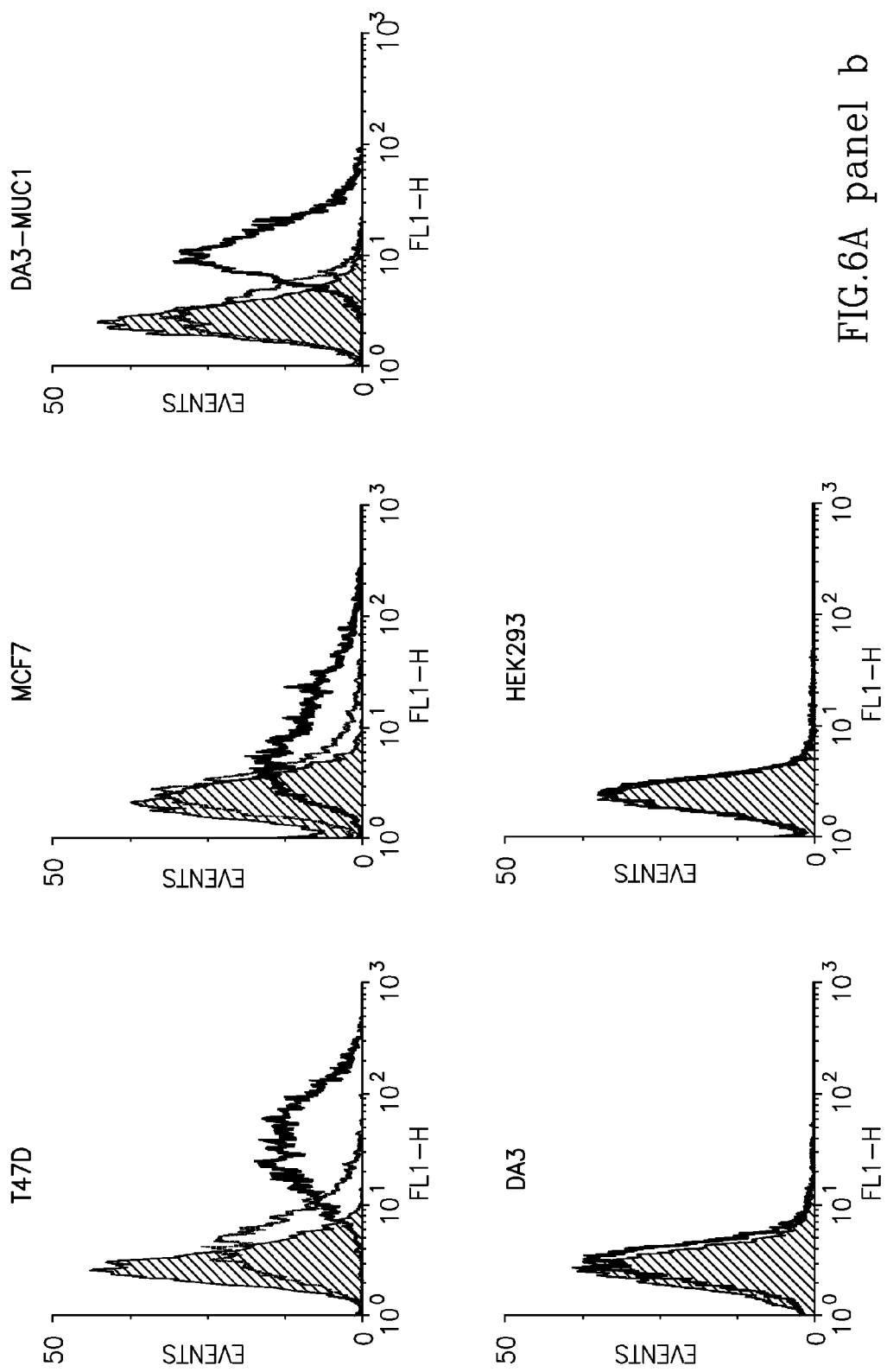
FIG. 6A panel b

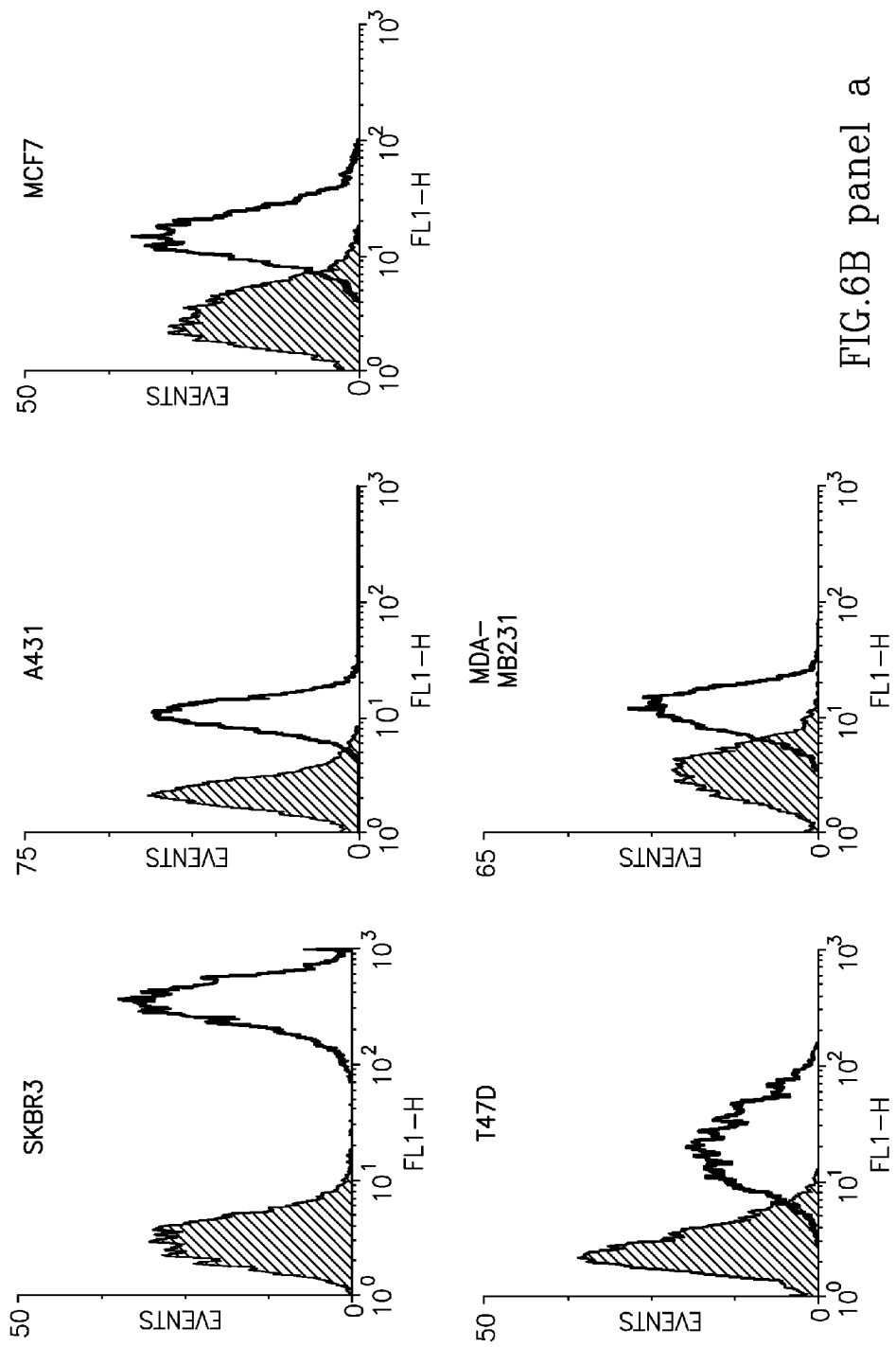
FIG.6B panel a

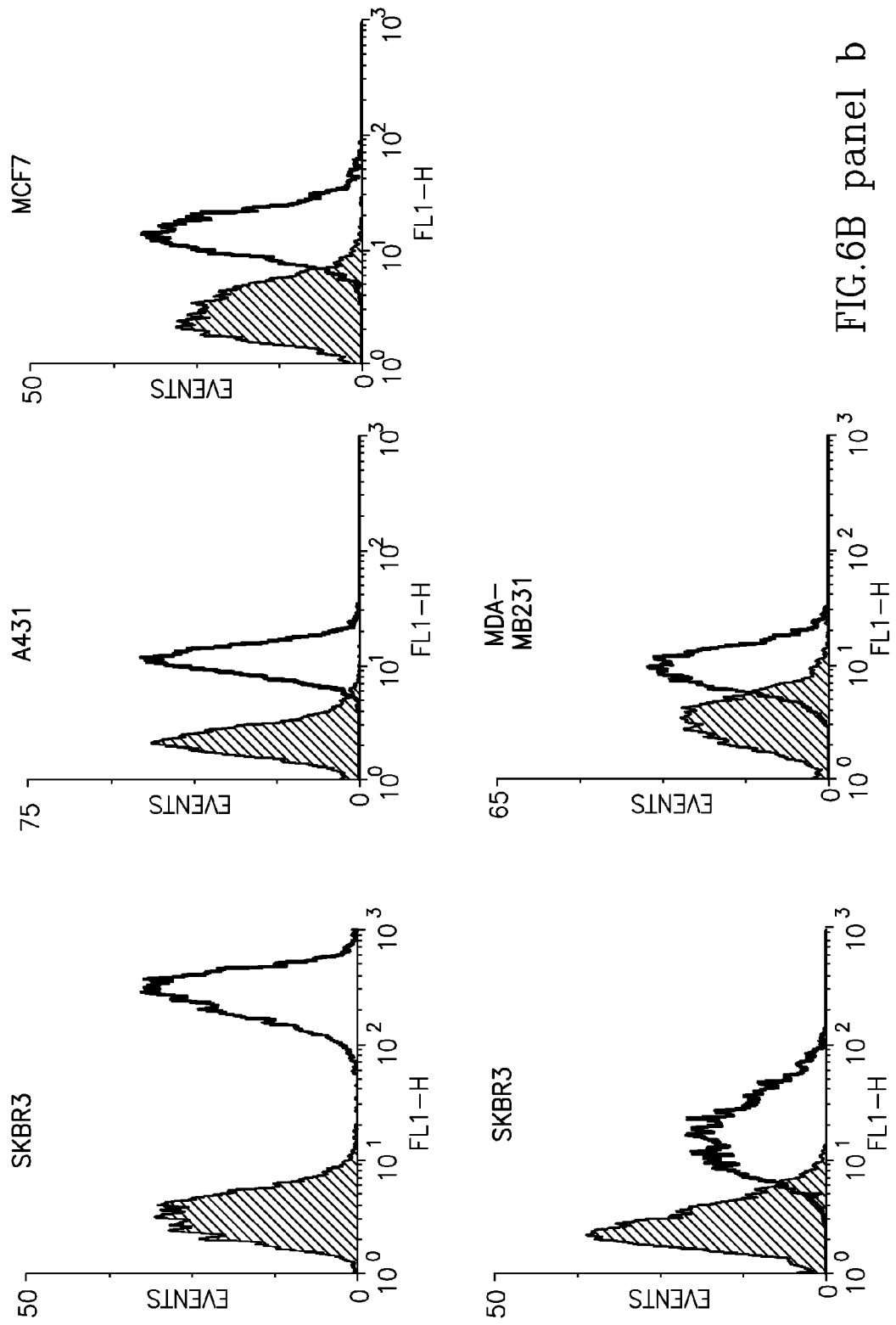
FIG. 6B panel b

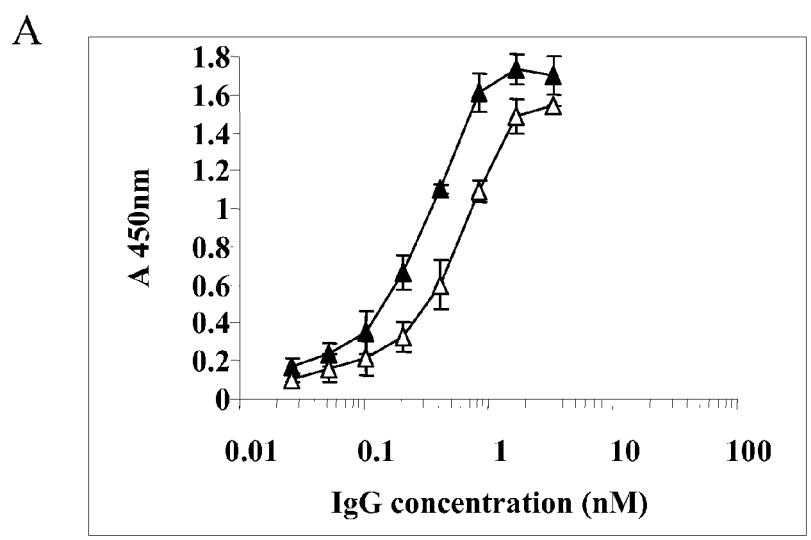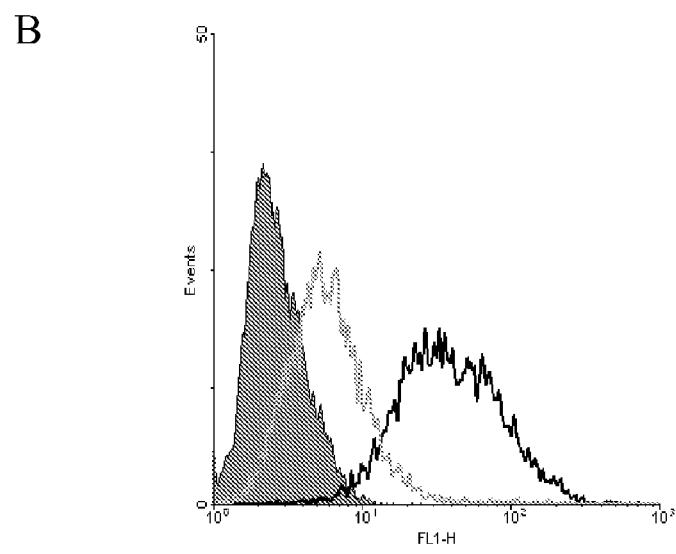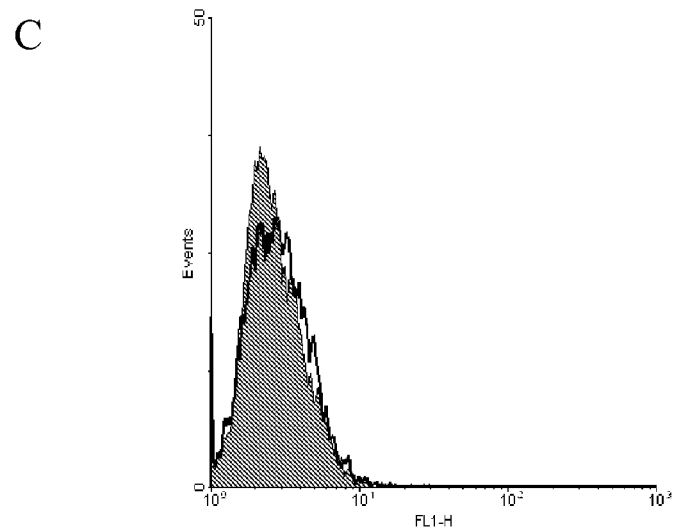
FIGURE 9

A. T47D
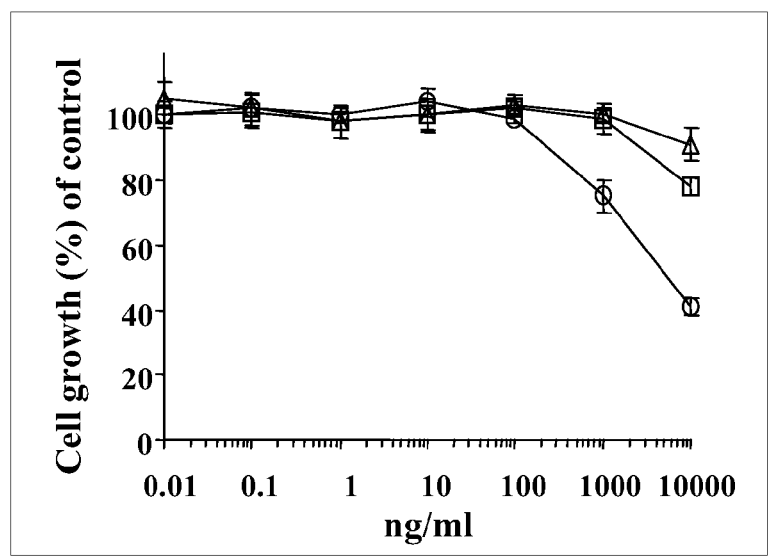
B. MCF7
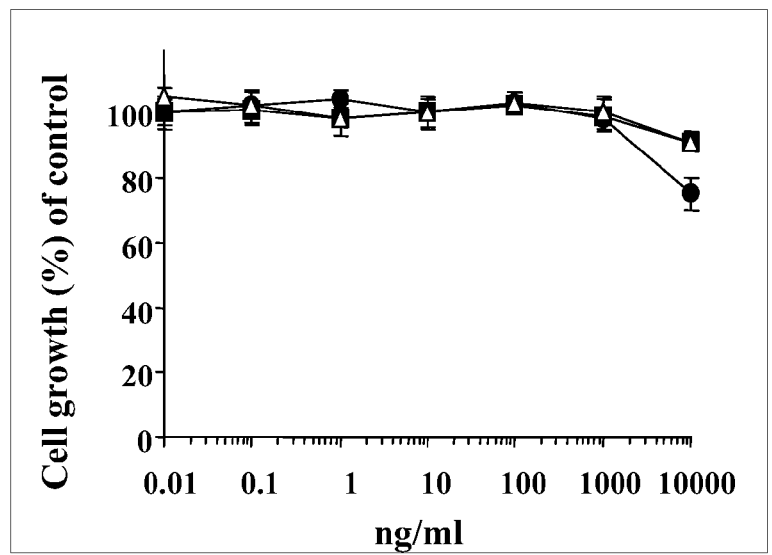
FIGURE 10

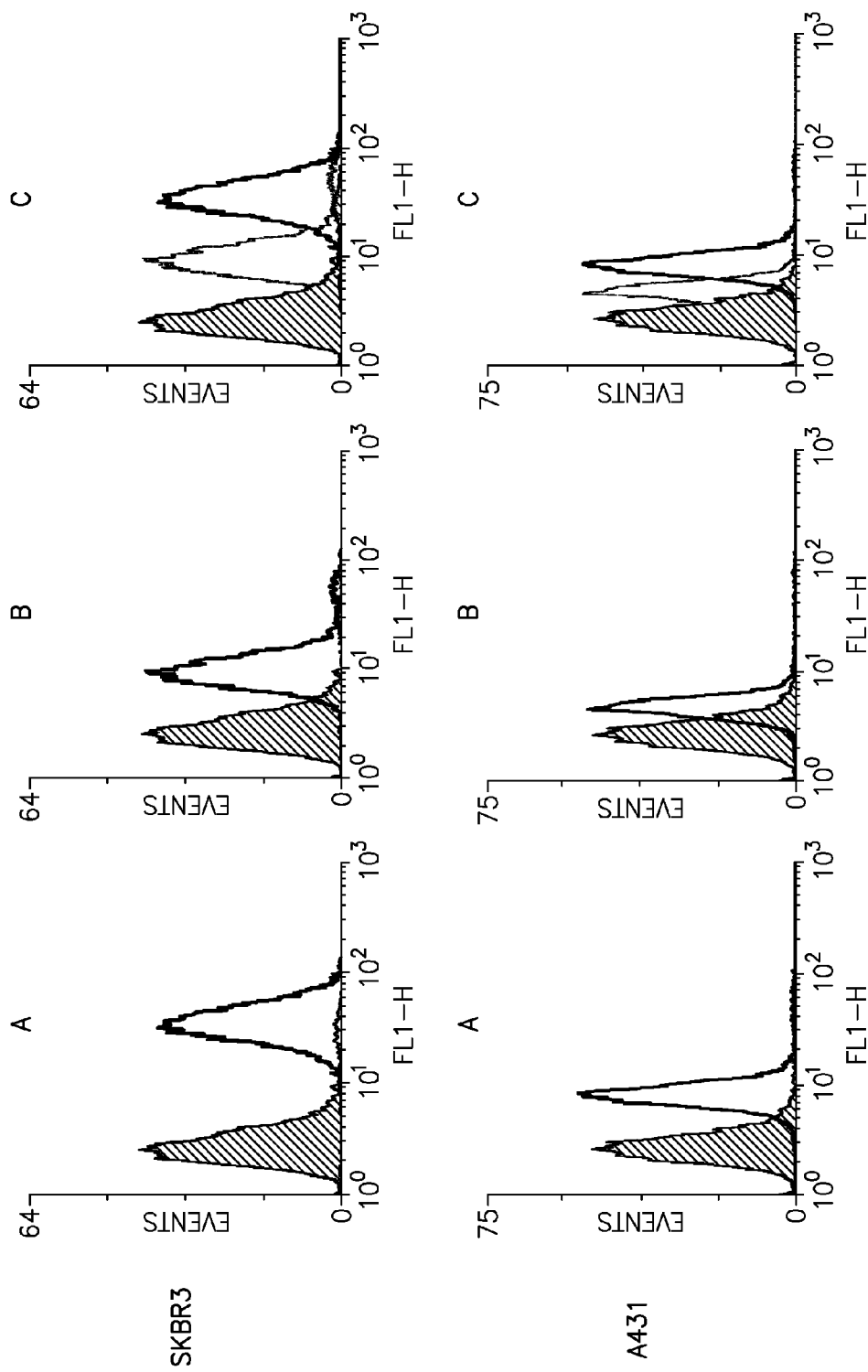
FIG.12 panels 1 and 2

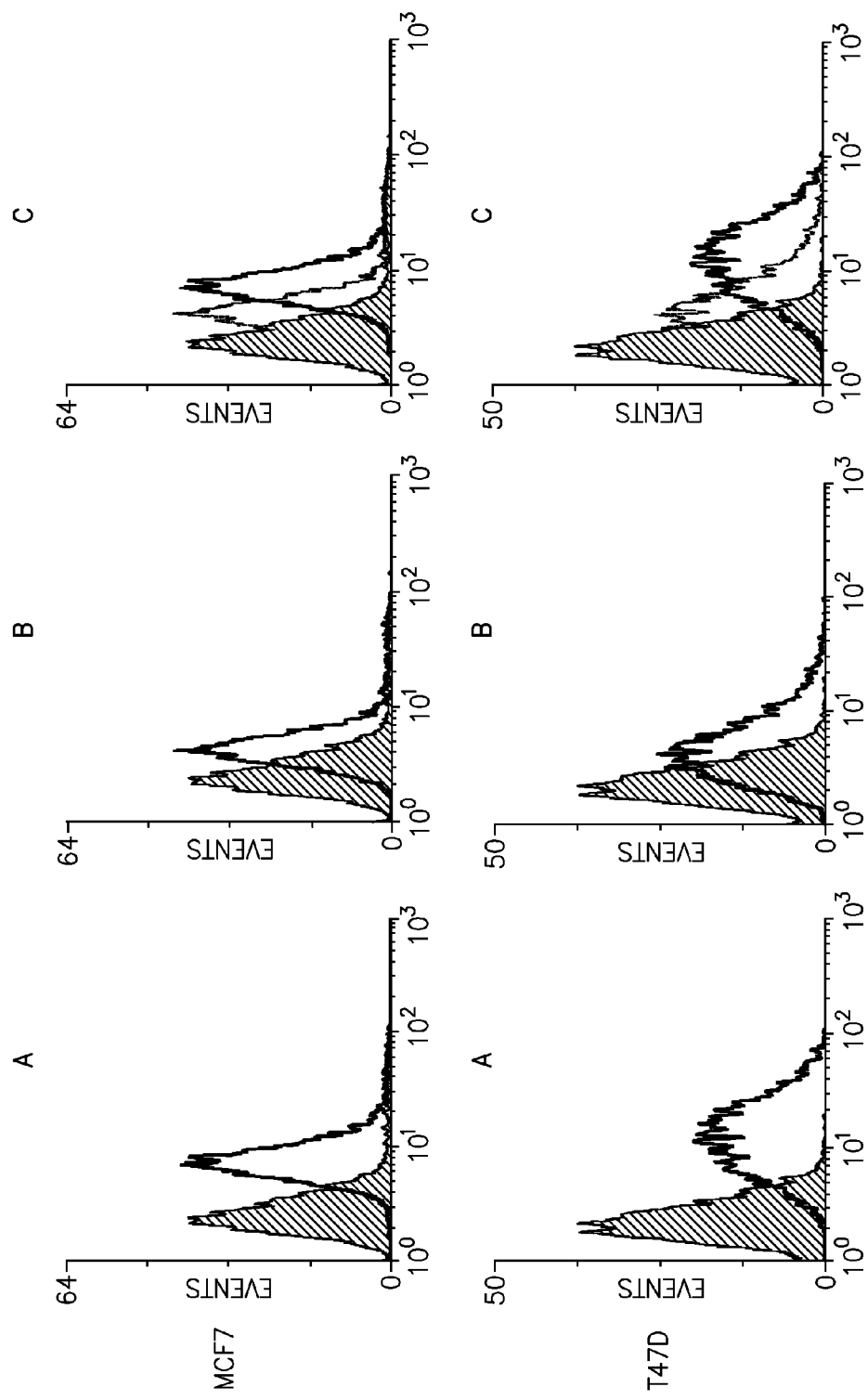
FIG.12 panels 3 and 4

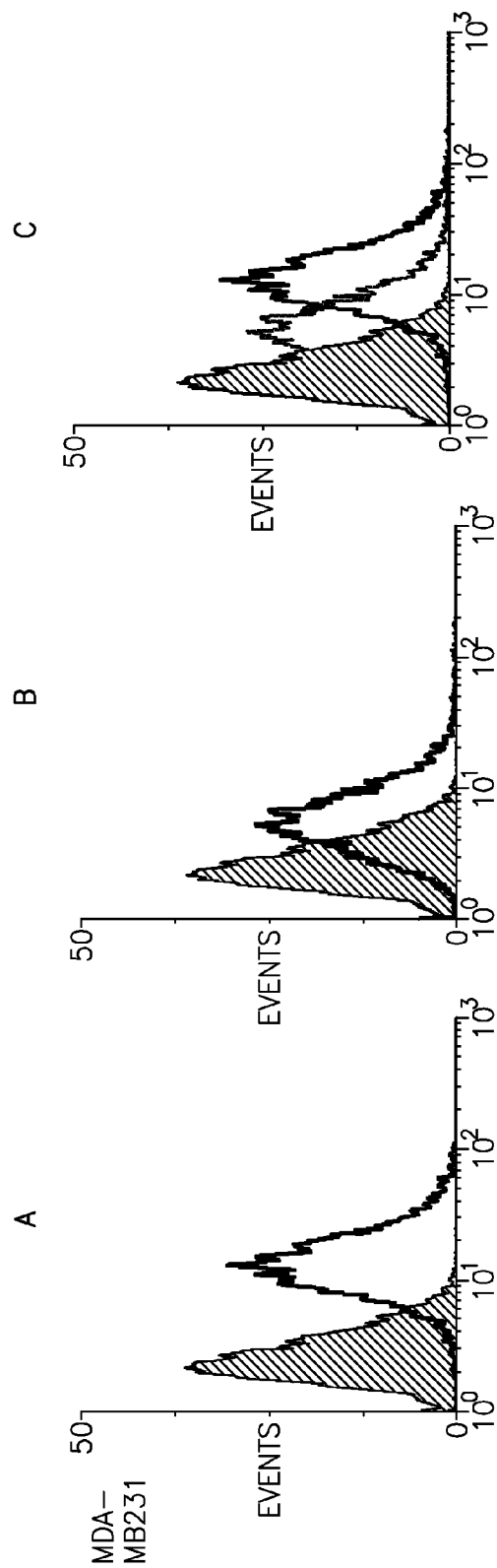
FIG.12 panel 5

A. SKBR3
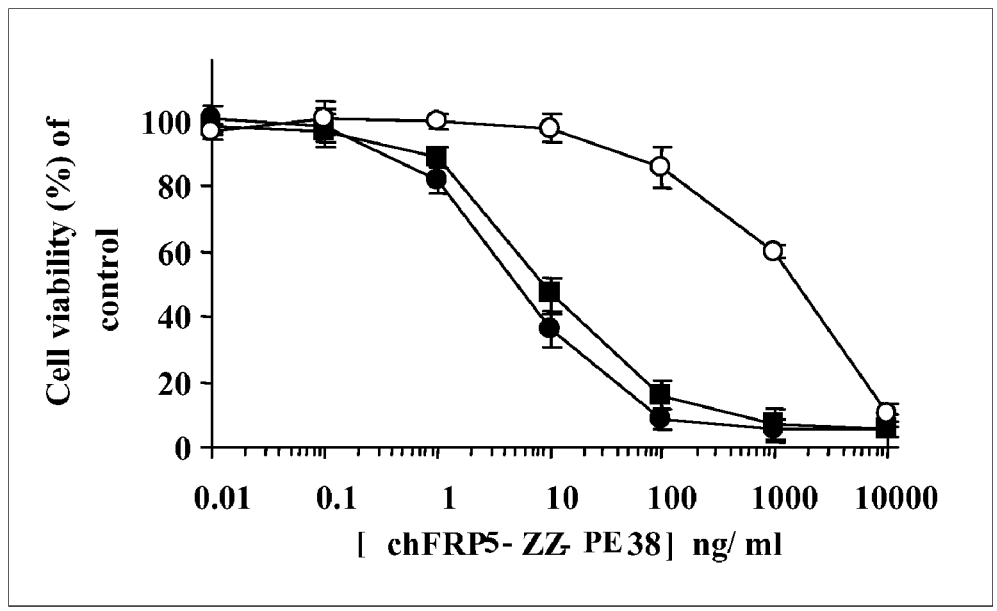
B. A431
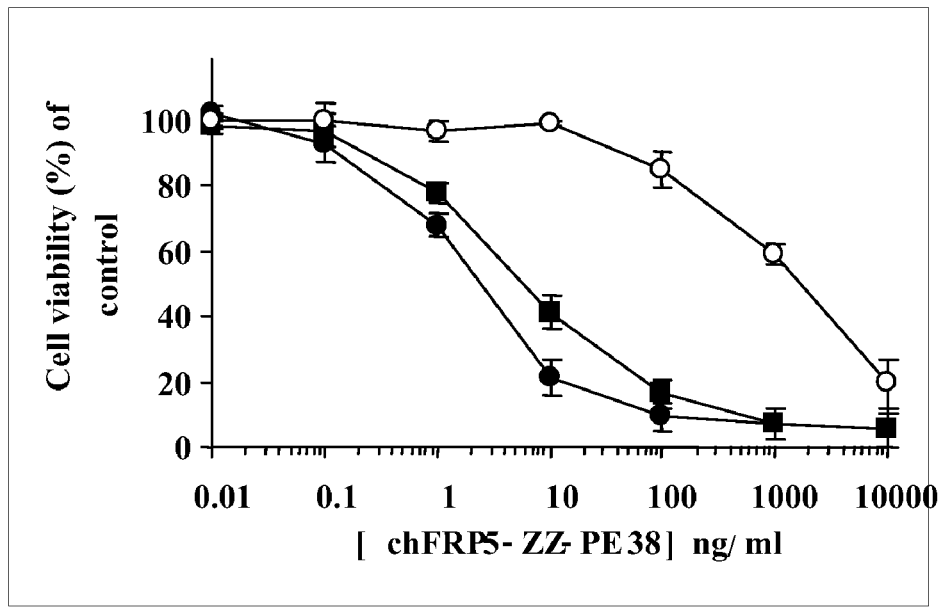
FIGURE 16

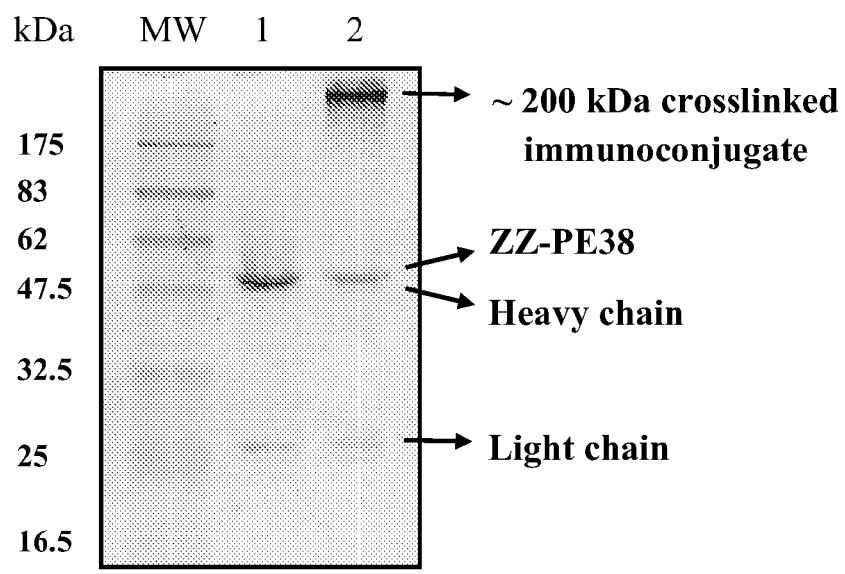
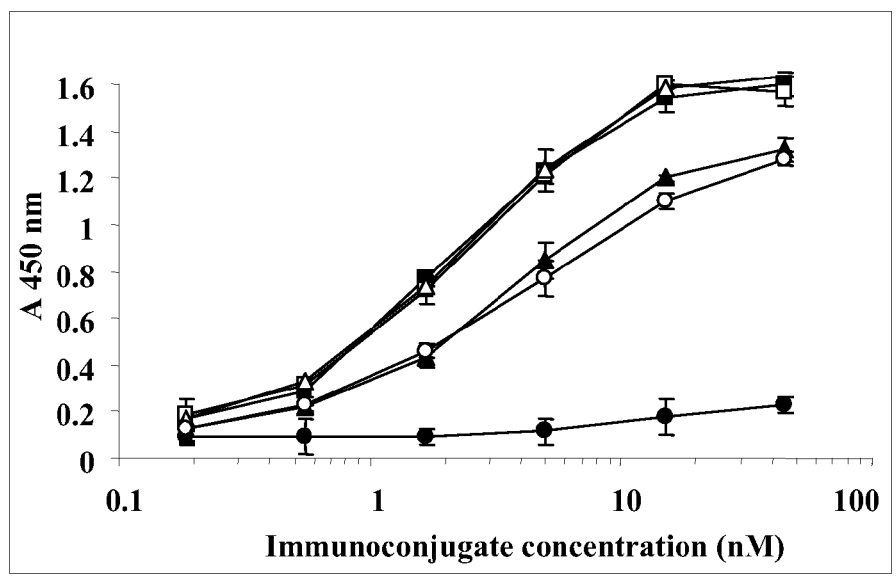
FIGURE 18

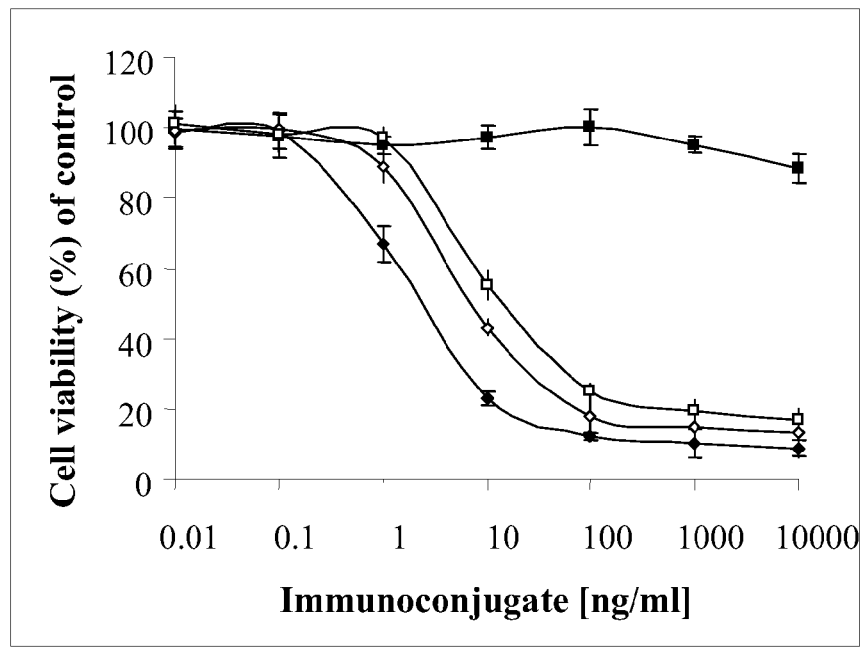
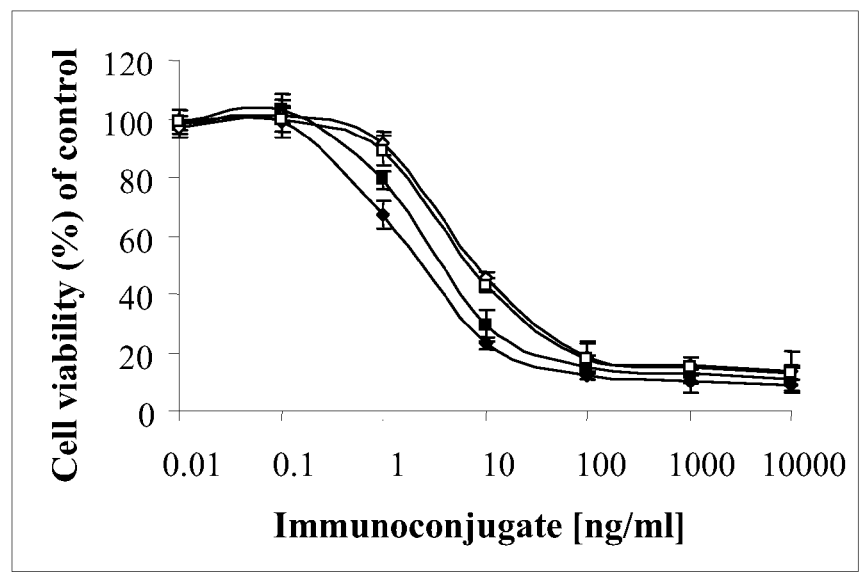
FIGURE 19

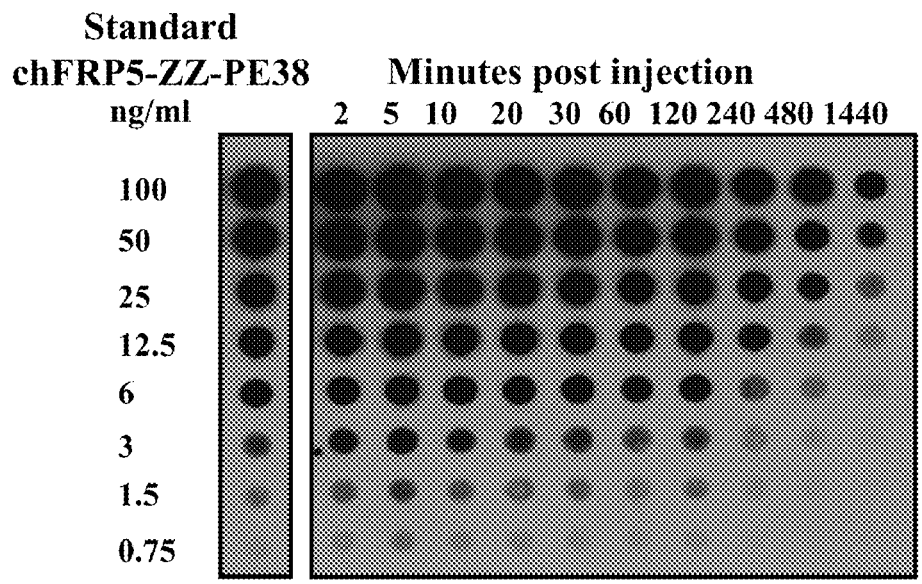
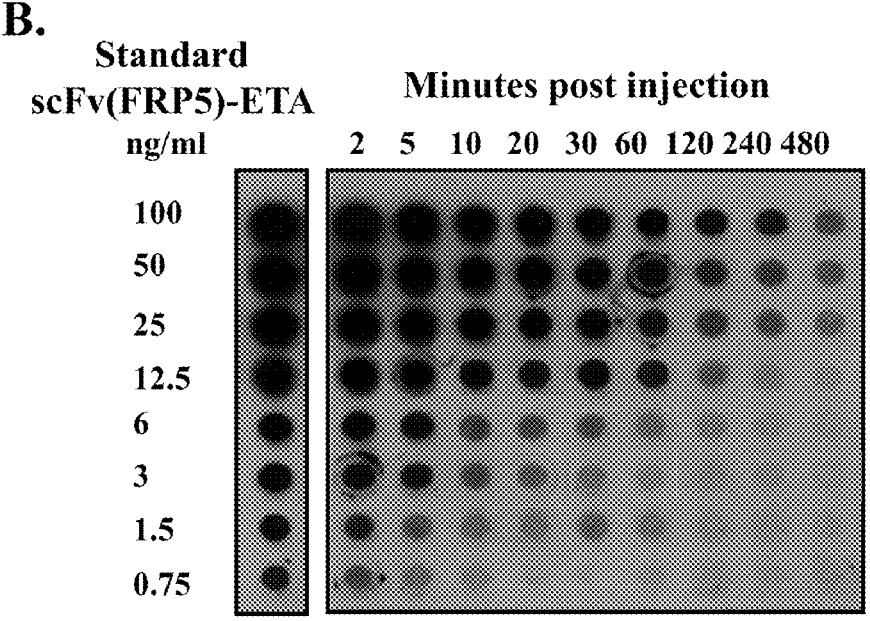
FIGURE 20

RECOMBINANT FUSION PROTEIN AND POLYNUCLEOTIDE CONSTRUCT FOR IMMUNOTOXIN PRODUCTION

CROSS-REFERENCE TO RELATED APPLICATIONS

This application is a divisional of application Ser. No. 12/117,494 filed May 8, 2008 now U.S. Pat. No. 8,043,621, which application claims the benefit of application No. 60/917,160 filed May 10, 2007. The entire content of each application is expressly incorporated herein by reference thereto.

FIELD OF THE INVENTION

The present invention relates to a polynucleotide construct encoding a fusion protein consisting of a domain which binds the immunoglobulin Fc region, genetically fused to a truncated form of Pseudomonas exotoxin A (PE). The present invention further provides immunotoxins, formed from complexes of the fusion protein with antibodies for targeted cell killing.

BACKGROUND OF THE INVENTION

The aim of drug targeting is to kill target cells such as cancer cells, while leaving normal tissues unharmed. Immunotoxins combine the selectivity of an antibody moiety with the potency of a toxin moiety. Such agents kill target cells via a process which involves specific binding to a cell surface antigen preferentially expressed on the cells, such as a tumor-associated antigen, internalization and delivery of the toxic moiety to the cytosol, where a critical cell function is inhibited, leading to cell death. A decisive breakthrough in immunotoxin development was the advent of hybridoma technology, making monoclonal antibodies (mAbs) available in limitless supply. The "first generation" of immunotoxins, for example as disclosed in U.S. Pat. No. 4,545,985, were chemically linked conjugates of mAbs or Fab' fragments capable of binding cancer cell antigens, and potent protein toxins derived from plants or bacteria such as ricin, abrin, saporin, Pseudomonas aeruginosa exotoxin (PE), cholera toxin (CT) and Diphtheria toxin (DT). Such early immunotoxins showed impressive results in vitro but in most cases displayed poor anti-tumor effects in animals or humans, and often with excessive toxicity.

The "second generation" of immunotoxins were generally fully recombinant antibody-toxin chimeric molecules, usually in the form of a single-chain antibody genetically fused to a truncated version of either DT or PE, such as disclosed for example in U.S. Pat. No. 6,051,405.

Over the years, a large number of antibodies that bind tumor-associated antigens have been isolated. Early on, the need for a rapid screening approach to assess the potential of such antibodies was recognized, since internalization is a pre-requisite for most drug delivery approaches (Casalini et al 1993, Cancer Immunol Immunother 37, 54-60). An undisputed proof of internalization can be provided by linking the antibody to a cytotoxic cargo (such as a drug or a toxin) and testing the ability of the antibody to deliver the cargo into a target cell. The first generation of immunotoxins could provide such a tool, but some antibodies are not readily conjugated. While use of second generation recombinant immunotoxins for screening purposes is technically feasible, it is extremely labor intensive.

Some agents that could potentially link any IgG to a toxin have been disclosed, for example in Kim and Weaver 1998, Gene 68, 315-21; O'Hare et al 1990, FEBS Lett 273, 200-4; Madshus et al 1991, J Biol Chem 266, 17446-53; Tonevitskii et al 1991, Mol Biol (Mosk) 25, 1188-96, but none of these disclosures show an agent effective in target cell killing.

The immunoglobulin Fc-binding protein denoted ZZ is a recombinant tandem repeated, mutated form of domain B of protein A from Staphylococcus aureus which has been used in a variety of biotechnological applications (Nilsson et al 1987, Protein Eng. 1, 107-13; Nilsson et al 1996, Protein Eng. 1, 107-13).

Fusion proteins composed of protein ZZ and diphtheria toxin, either the full-length toxin or fragment B thereof, have been disclosed (Madshus et al 1991, supra; Nizard et al 1998, FEBS Lett 433, 83-8). A chimeric protein composed of S. aureus protein A fragments and Pseudomonas aeruginosa exotoxin A has been disclosed (Tonevitskii et al 1991, supra). While the chimeric protein was shown to be capable of ADP-ribosylation of elongation factor 2 and binding to immunoglobulin, evaluation of its cytotoxic properties in two model systems showed only a slight inhibition of target cell growth.

U.S. Pat. No. 5,917,026 discloses DNA sequences encoding fusion proteins comprising a first segment which encodes a native or mutant subunit of a bacterial toxin that confers enzymatic ADP-ribosylating activity inter alia Pseudomonas toxin, and a second segment which encodes a peptide which confers water solubility on the fusion protein and targets the fusion protein to a specific cell receptor different from receptors binding to the native toxin, and can thereby mediate intracellular uptake of at least the toxin subunit. According to the disclosure, the receptor may be one present on B lymphocytes and the peptide may be inter alia S. aureus protein A or a fragment thereof in single or multiple copies. The only fusion proteins specifically disclosed are those composed of cholera toxin subunit A1 linked to DD, the latter being a dimer of the D-region of protein A, and such fusions are described as being non-toxic in vivo and capable of enhancing immune effects of B and T cells. According to the disclosure, the intended use of the fusion protein is for potentiating immune responses.

There remains a need for effective immunotoxins and recombinant reagents for screening of antibodies for their potential as components of such immunotoxins, in particular the ability to be internalized within target cells.

SUMMARY OF THE INVENTION

The present invention provides for the first time a recombinant fusion protein denoted as ZZ-PE, which comprises the IgG Fc-binding ZZ domain derived from S. aureus protein A (ZZ) genetically fused to a specific truncated form of Pseudomonas aeruginosa exotoxin A (PE), and a polynucleotide construct encoding same. The ZZ-PE forms surprisingly tight complexes with IgG and other proteins comprising an Fc-region derived from IgG. When complexed with IgG, the ZZ-PE does not undermine specific antigen recognition. The inventors have surprisingly found that the ZZ-PE fusion protein can be used as a "adaptive" reagent for converting internalizing IgG antibodies into immunotoxin complexes or conjugates for targeted cell killing. More particularly, complexes or conjugates comprising the ZZ-PE fusion protein and IgG antibodies which are efficiently internalized into target cells expressing the antigen recognized by the antibody, can be used as pharmaceutical reagents for targeted cell killing, for example of cancer cells.

According to a first aspect, the present invention provides a polynucleotide construct encoding a fusion protein, wherein the construct comprises a first nucleotide sequence encoding an immunoglobulin Fc-binding domain and a second nucleotide sequence encoding a truncated form of *Pseudomonas* exotoxin.

As used herein, an "immunoglobulin Fc-binding domain" refers to a protein which binds the Fc region of immunoglobulin molecules.

According to one embodiment, the immunoglobulin Fc-binding domain is derived from *S. aureus* protein A. According to one embodiment, the immunoglobulin Fc-binding domain derived from *S. aureus* protein A comprises domain B of protein A. According to one embodiment, the first nucleotide sequence encoding the immunoglobulin Fc-binding domain is in single or multiple copies. According to one embodiment, the immunoglobulin Fc-binding domain derived from *S. aureus* protein A is denoted as ZZ and has the amino acid sequence of SEQ ID NO: 2. According to one embodiment, the immunoglobulin Fc-binding domain is an anti-Fc single chain antibody.

According to one embodiment, the truncated form of *Pseudomonas* exotoxin has an amino acid sequence selected from the group consisting of SEQ ID NO:3 (denoted as PE38); SEQ ID NO:23 (denoted as PE38KDEL), SEQ ID NO:24 (denoted as PE38RDEL), SEQ ID NO:25 (denoted as PE37) and SEQ ID NO:26 (denoted as PE40).

According to a currently preferred embodiment the truncated form of *Pseudomonas* exotoxin is that denoted as PE38 and has the amino acid sequence of SEQ ID NO:3.

According to one embodiment, the first nucleotide sequence and the nucleotide second sequence of the polynucleotide construct are joined by a linker nucleotide sequence, wherein the linker nucleotide sequence encodes a peptide linker having from four to 20 amino acids.

According to one embodiment, the peptide linker comprises SEQ ID NO:27. According to one embodiment, the polynucleotide construct encodes a fusion protein that has the amino acid sequence of SEQ ID NO:1.

According to another embodiment, the polynucleotide comprises the sequence of SEQ ID NO:6. According to another embodiment, an expression vector comprises the polynucleotide construct of the invention. According to one embodiment, the expression vector comprises a T7 promoter and a pelB leader for secretion operably linked to the polynucleotide. According to another embodiment, the expression vector comprises the sequence of SEQ ID NO:5.

According to another embodiment, the expression vector has the sequence of SEQ ID NO:5.

According to yet another embodiment, a host cell comprises the polynucleotide construct of the invention.

According to one embodiment, the host cell is selected from the group consisting of a prokaryotic cell and a eucaryotic cell. According to one embodiment, the prokaryotic cell is a bacterium. According to one embodiment, the bacterium is from a strain of *Escherichia coli*.

According to another aspect, the present invention provides a recombinant fusion protein, wherein the protein comprises a first segment which is an immunoglobulin Fc-binding domain, and a second segment which is a truncated form of *Pseudomonas* exotoxin.

In one embodiment, the Fc-binding domain is derived from *S. aureus* protein A. In one embodiment, the Fc-binding domain derived from *S. aureus* protein A comprises domain B of protein A. In one embodiment, the Fc-binding domain derived from *S. aureus* protein A is denoted as ZZ and has the amino acid sequence of SEQ ID NO: 2. According to one embodiment, the immunoglobulin Fc-binding domain is present in the fusion protein in single or multiple copies. According to one embodiment, the immunoglobulin Fc-binding domain is an anti-Fc single chain antibody.

In another embodiment, the truncated form of *Pseudomonas* exotoxin has an amino acid sequence selected from the group consisting of SEQ ID NO:3 (denoted as PE38); SEQ ID NO:23 (denoted as PE38KDEL), SEQ ID NO:24 (denoted as PE38RDEL), SEQ ID NO:25 (denoted as PE37) and SEQ ID NO:26 (denoted as PE40).

According to one embodiment the truncated form of *Pseudomonas* exotoxin is that denoted as PE38 and has the amino acid sequence of SEQ ID NO:3.

According to one embodiment, the first segment and the second segment of the fusion protein are joined by a peptide linker having from four to 20 amino acids. According to one embodiment, the peptide linker has the sequence of SEQ ID NO:27.

According to a currently preferred embodiment, the fusion protein has the amino acid sequence of SEQ ID NO:1. The fusion protein having the amino acid sequence of SEQ ID NO:1 is specifically referred to herein as "ZZ-PE38".

According to one embodiment, the fusion protein is encoded by the sequence of SEQ ID NO:6. According to one embodiment, the fusion protein is expressed by the expression vector having the sequence of SEQ ID NO:5.

According to one embodiment, an immunotoxin comprises a complex of the fusion protein of the invention and an antibody, wherein the antibody is capable of specifically binding an antigen expressed on the surface of a target cell. In one embodiment, the antibody is selected form the group consisting of a monoclonal antibody, a humanized antibody, a chimeric antibody, a single chain antibody, and a fragment thereof. In one embodiment, the antibody is capable of being internalized into the target cell. According to one embodiment, the antibody is an IgG1.

According to one embodiment, the immunotoxin comprises a fusion protein, wherein the fusion protein has the amino acid sequence of SEQ ID NO:1.

In one embodiment, the complex is an immuno complex. In one embodiment, the complex is a chemically conjugated complex. In one embodiment, the complex is a cross-linked complex. In one embodiment, the target cell is selected from the group consisting of a cancer cell and a pathogen infected cell. In one embodiment, the pathogen is selected from the group consisting of a parasite and a virus.

In one embodiment, the antigen is selected from the group consisting of a tumor-associated antigen, a pathogen-associated antigen, a parasite-associated antigen and a virus-associated antigen. In one embodiment, the tumor-associated antigen is selected from the group consisting of MUC1 and ErbB2. In one embodiment, the target cell is a cancer cell. In one embodiment, the cancer cell is from a site selected from the group consisting of lung, colon, rectum, breast, ovary, prostate gland, head, neck, bone, kidney, liver, skin and the immune system. In one embodiment, the cancer cell is a breast cancer cell.

According to another aspect, the invention provides a method for selectively killing a target cell in a subject in need thereof, the method comprising the steps of:
  a. providing a recombinant fusion protein, wherein the fusion protein comprises a first segment which is an immunoglobulin Fc-binding domain and a second segment which is a truncated form of *Pseudomonas* exotoxin;

b. selecting an antibody which is specific for an antigen present on the target cell and which is capable of being internalized into the target cell;
c. combining the antibody from (b) with the fusion protein from (a) so as to form an immunotoxin complex; and
d. exposing the target cells to an effective amount of the immunotoxin complex of (c) under conditions which enable internalization of the immunotoxin complex, thereby selectively killing the target cell in the subject in need thereof.

Embodiments of the fusion protein, the Fc-binding domain and the truncated form of *Pseudomonas* exotoxin are as hereinbefore described.

According to a currently preferred embodiment, the fusion protein has the amino acid sequence of SEQ ID NO: 1. According to one embodiment, the antibody is an IgG1. In one embodiment, the antibody is selected form the group consisting of a monoclonal antibody, a humanized antibody, a chimeric antibody, a single chain antibody, and a fragment thereof. According to a specific embodiment, the antigen recognized on the target cells is selected from the group consisting of MUC-1 and ErbB2. According to one embodiment, the subject is a mammal. According to one embodiment, the mammal is a human.

In one embodiment, the target cell is a cancer cell. In one embodiment, the cancer cell is from a site selected from the group consisting of lung, colon, rectum, breast, ovary, prostate gland, head, neck, bone, kidney, liver, skin and the immune system. In one embodiment, the cancer cell is a breast cancer cell.

According to one embodiment, the exposing in (d) is carried out in vivo or ex vivo. According to one embodiment, the exposing in (d) comprises administering the immunotoxin complex by a route selected from the group consisting of intravenous, intraperitoneal, subcutaneous, intramuscular and intralymphatic. According to one embodiment, step (c) comprises forming covalent bonds between the antibody and the fusion protein. In one embodiment, the step of forming covalent bonds comprises chemical conjugation or cross-linking.

According to yet another aspect, the invention provides a method for assessing whether an antibody specific for a cell surface antigen is internalized into target cells expressing the antigen, the method comprising:
a. providing a recombinant fusion protein, wherein the fusion protein comprises a first segment which is the ZZ Fc-binding domain derived from *S. aureus* protein A and a second segment which is PE38 derived from *Pseudomonas* exotoxin;
b. selecting at least one antibody specific for the cell surface antigen present on the target cells;
c. combining the antibody from (b) with the ZZ-PE38 fusion protein from (a) to form a complex; and
d. exposing the target cells to the complex of (c); and
e. assessing whether the complex is internalized into the target cells.

According to one embodiment, the fusion protein has the amino acid sequence of SEQ ID NO: 1. According to another embodiment, the fusion protein further comprises a detectable moiety.

B. Comparative cellular ErbB2 binding-affinity by chFRP5 IgG1 (filled triangles) and HERCEPTIN (trastuzumab) mAb (filled squares) was assessed by whole-cell ELISA. The human breast adenocarcinoma SKBR3 cell line was used as ErbB2 expressing cells. Cells were incubated with antibodies (20 μg/ml) for 1.5 h at 4° C. HRP-conjugated goat anti-human and HRP-labeled goat anti-mouse antibodies were used as secondary antibodies. The ELISA was developed using the chromogenic HRP substrate TMB. The error bars represent standard deviations of three independent experiments. The binding-affinity was estimated as the IgG concentration that generates 50% of the maximal signal.

FIGS. 6A and B: Flow-cytometry analysis of antibody binding to cells expressing MUC1.

A. H23 mAb (panel a) and chH23 mAb (panel b) assessed for binding to cellular MUC1 using the cell lines DA3 (murine), DA3-MUC1 (MUC1-transfected DA3), T47D (human breast carcinoma), MCF7 (human breast carcinoma) and HEK293 (human kidney). To confirm specificity, antibodies (10 μg/ml) were incubated in the presence or absence of an excess of MUC1 protein prior to incubation with the cells. Filled areas, negative control; bold black line, specific binding of antibody; black line, competition for cell binding with soluble MUC1 protein.

B. chFRP5 IgG1 (panel a) HERCEPTIN (trastuzumab) mAb (panel b) were assessed for binding to cellular ErbB2 using the cell lines SKBR3 (human breast adenocarcinoma), the A431 (human epidermoid carcinoma), T47D (human breast carcinoma), MCF7 (human breast carcinoma) and MDA-MB231 (human mammary carcinoma). Cells were incubated with antibodies (10 μg/ml) for 1.5 h at 4° C. FITC-conjugated goat anti-human and FITC-labeled goat anti-mouse antibodies were used as secondary antibodies. Filled areas, negative control; black line, specific binding of antibody.

Figure 7:
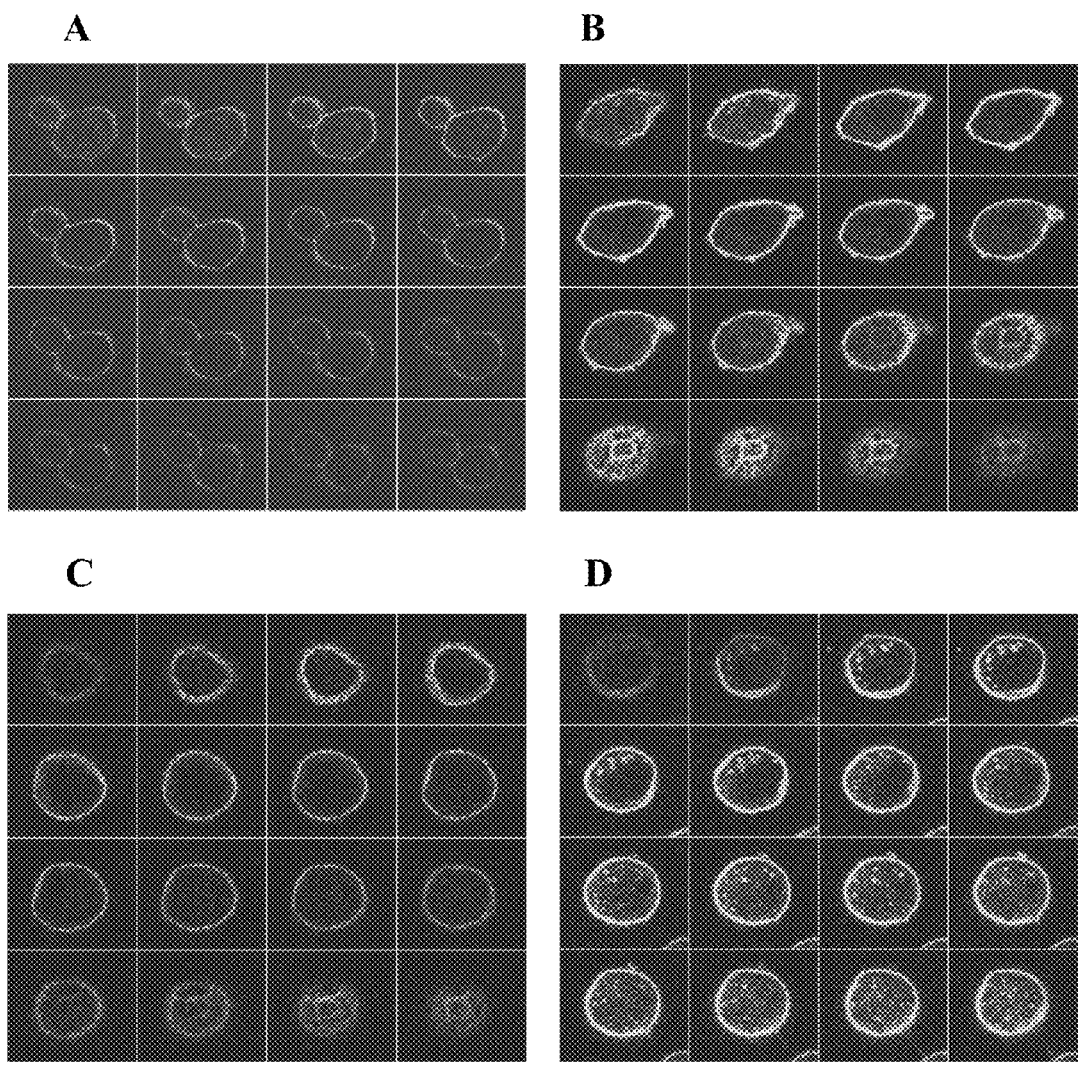

FIG. 7.: Analysis of antibody internalization confocal microscopy.

Internalization of chH23 IgG1 into human breast carcinoma T47D cells and of chFRP5 IgG1 into SKBR3 cells line was evaluated at 4° C. (A and C, respectively) and at 37° C. (B and D, respectively) using confocal microscopy. For evaluation at 4° C., cells were preincubated with complete medium supplemented with 0.5% $NaN_3$ for 2 h at 4° C., followed by the addition of antibody (5 μg/ml) and incubation for 1 h at 4° C. For evaluation at 37° C., cells were incubated with antibody (5 μg/ml) in complete medium for 1 h at 37° C. in a humidified atmosphere of 95% air and 5% $CO_2$.

Figure 8:
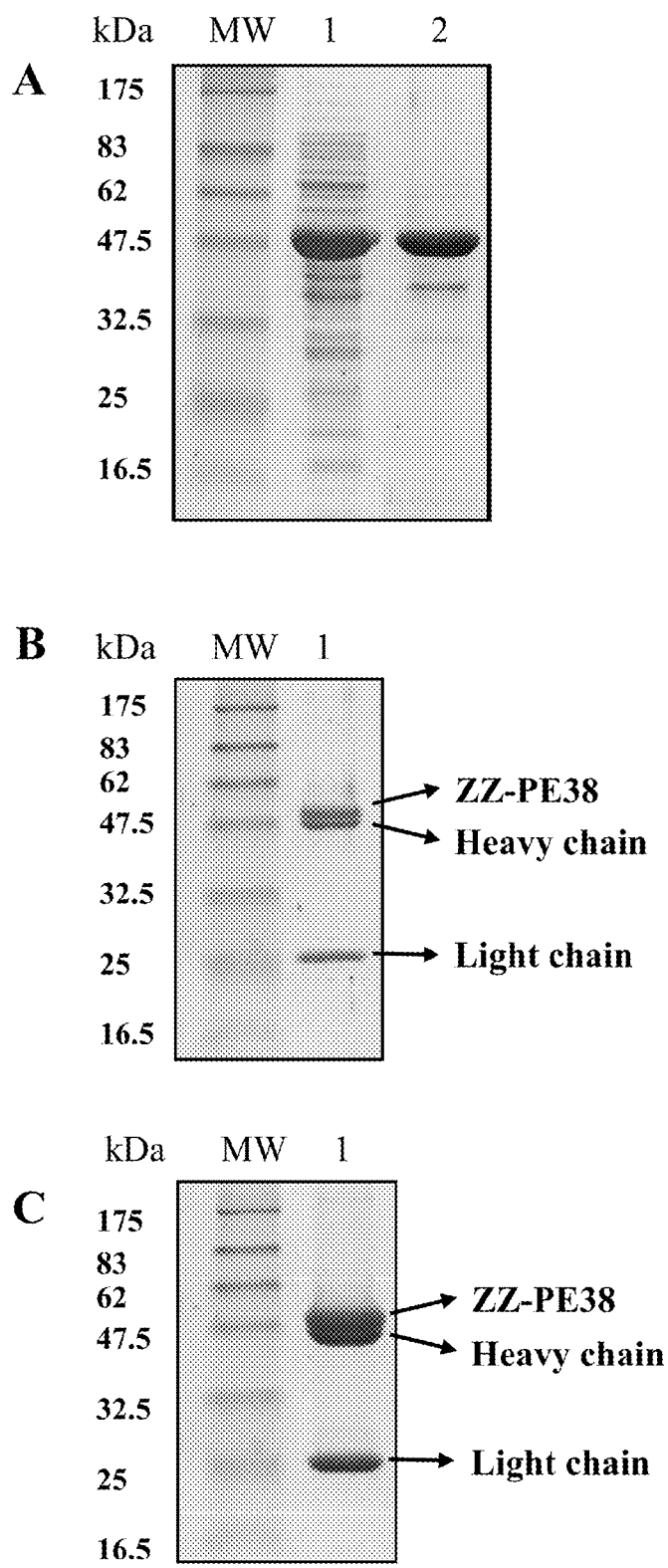

FIGS. 8A, B and C: Purification of soluble ZZ-PE38 fusion protein and immunoconjugates comprising ZZ-PE38.

A. Purification of soluble ZZ-PE38. Purified ZZ-PE38 fusion protein was obtained by subjecting periplasmic fractions to two sequential chromatography steps of Q-SEPHAROSE and MONO-Q anion exchange columns using fast protein liquid chromatography (FPLC). MW, molecular mass marker; lane 1, soluble ZZ-PE38 periplasm extract (15 μg); lane 2, purified ZZ-PE38 (5 μg).

B. Purification of chH23-ZZ-PE38. Immunoconjugate chH23-ZZ-PE38 was purified from a mixed sample containing excess ZZ-PE38 and unbound chH23 by gel filtration using FPLC. MW, molecular mass marker; lane 1, purified chH23-ZZ-PE38 (2 μg).

C. Purification of chFRP5-ZZ-PE38. Immunoconjugate chFRP5-ZZ-PE38 was purified from a mixed sample containing excess ZZ-PE38 and unbound chFRP5 gel filtration using FPLC. MW, molecular mass marker; lane 1, purified chFRP5-ZZ-PE38 (5 μg). In A, B and C, proteins were separated on a 12%/SDS polyacrylamide gel under reducing conditions and visualized by staining with GELCODE BLUE® dye. In B and C, the positions of ZZ-P38 and antibody heavy and light chains are marked.

FIGS. 9A, B and C: Analysis of chH23-ZZ-PE38.

A. Analysis of MUC1 binding by chH23-ZZ-PE38 in whole-cell ELISA. Human breast carcinoma T47D cells were incubated with 1 μg/ml of chH23-ZZ-PE38 or chH23 for 1.5 h at 4° C., washed and incubated with rabbit anti-PE sera mixed with either HRP-conjugated goat anti-rabbit antibody or with HRP-labeled goat anti-human antibody for the detection of bound chH23-ZZ-PE38 immunotoxin (open triangles), or bound chH23 (filled triangles), respectively. The ELISA was developed using the chromogenic HRP substrate TMB. The error bars represent standard deviations of three independent experiments.

B and C. Flow-cytometry analysis of chH23-ZZ-PE38 immunoconjugate. Cellular MUC1 binding activity was evaluated on human breast carcinoma T47D cell line. Cells were incubated with 10 μg/ml of chH23-ZZ-PE38 (B) or control hIgG-ZZ-PE38 (C) for 1.5 h at 4° C. In (B), specific chH23-ZZ-PE38 binding was confirmed by incubation of the immunoconjugate in the presence or absence of 10-fold excess of un-conjugated chH23 IgG1 prior to incubation with the cells. Rabbit anti-PE sera mixed with FITC-labeled goat anti-rabbit was used for the detection of bound chH23-ZZ-PE38 immunotoxin. Filled areas, negative control; black line, specific binding of antibody; grey line, competition for cell binding with chH23 IgG1.

FIG. 10: Inhibition of the growth of human tumor cell lines by chH23-ZZ-PE38 immunoconjugate.

T47D (A) and MCF7 (B) tumor cells were incubated for 48 h with the indicated concentration of chH23-ZZ-PE38 (filled circles), hIgG-ZZ-PE38 (open triangles) or ZZ-PE38 (filled squares). The relative number of viable cells was determined using an enzymatic MTT assay and is indicated as the absorption at 570 nm. Each point represents the mean of a set of data determined in triplicate in three independent experiments. The results are expressed as percentage of living cells respect to the untreated controls that were processed simultaneously using the following equation: ($A_{570}$ of treated sample/$A_{570}$ of untreated sample)×100. The $IC_{50}$ values were defined as the immunotoxin concentrations inhibiting cell growth by 50%.

Figure 11:
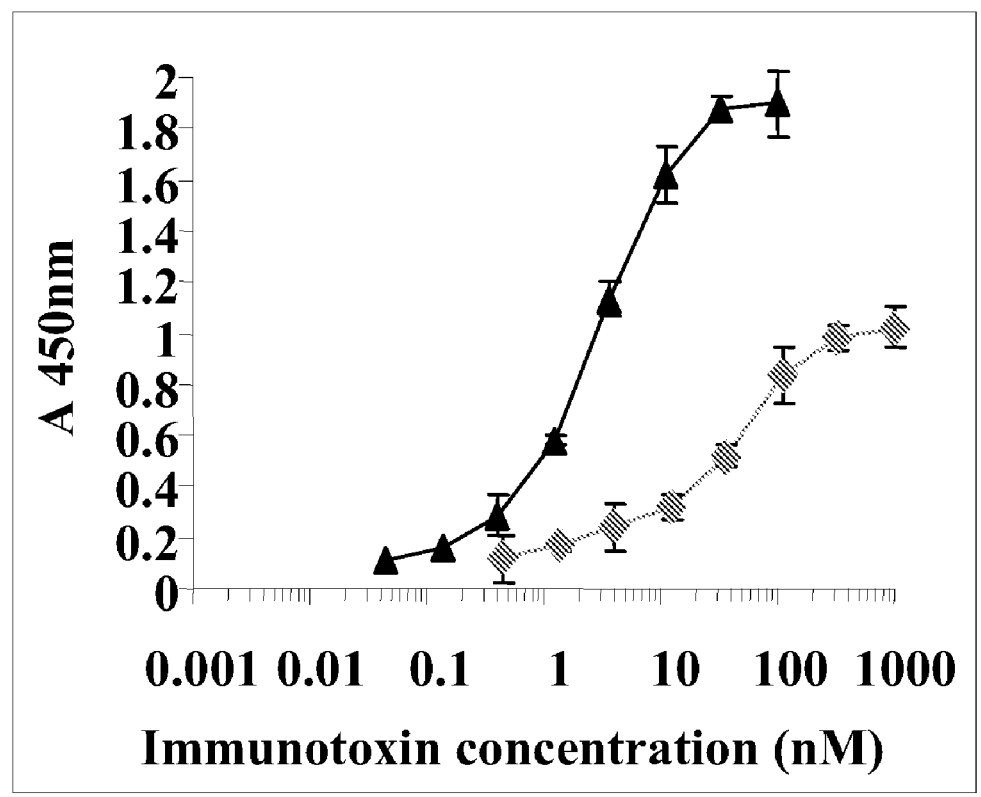

FIG. 11: Evaluation of ErbB2 binding-affinity by whole-cell ELISA.

Comparative cellular ErbB2 binding-affinity by chFRP5-ZZ-PE38 (filled triangles) and scFv(FRP5)-ETA (filled diamonds) was tested by whole-cell ELISA. ErbB2 expressing human breast adenocarcinoma SKBR3 cells were incubated with 100 nm of chFRP5-ZZ-PE38 or 1000 nm of scFv (FRP5)-ETA for 1.5 h at 4° C. Following washing steps, Rabbit anti-PE sera mixed with HRP-conjugated goat anti-rabbit were used for the detection of bound immunotoxins. The ELISA was developed using the chromogenic HRP substrate TMB. The error bars represent standard deviations of three independent experiments. The binding-affinities were estimated as the immunotoxin concentration that generates 50% of the maximal signal.

FIG. 12: Flow cytometry analysis.

Comparison between chFRP5-ZZ-P38 and scFv(FRP5)-ETA for binding to cellular ErbB2 using the cell lines SKBR3 (human breast adenocarcinoma), A431 (human epidermoid carcinoma), T47D (human breast carcinoma), MCF7 human breast carcinoma and MDA-MB231 (human mammary carcinoma). Cells were incubated with 5 μm of each immunotoxin for 1.5 h at 4° C. Rabbit anti-PE sera mixed with FITC-labeled goat anti-rabbit were used for the detection of bound immunotoxin. (A), filled areas, negative control; black line, specific binding of chFRP5-ZZ-P38; (B), filled areas, negative control; black line, specific binding of scFv(FRP5)-ETA; (C), overlapping staining intensities of both immunotoxins, filled areas, negative control; bold black line, specific binding of chFRP5-ZZ-P38; black line, specific binding of scFv (FRP5)-ETA.

Figure 13:
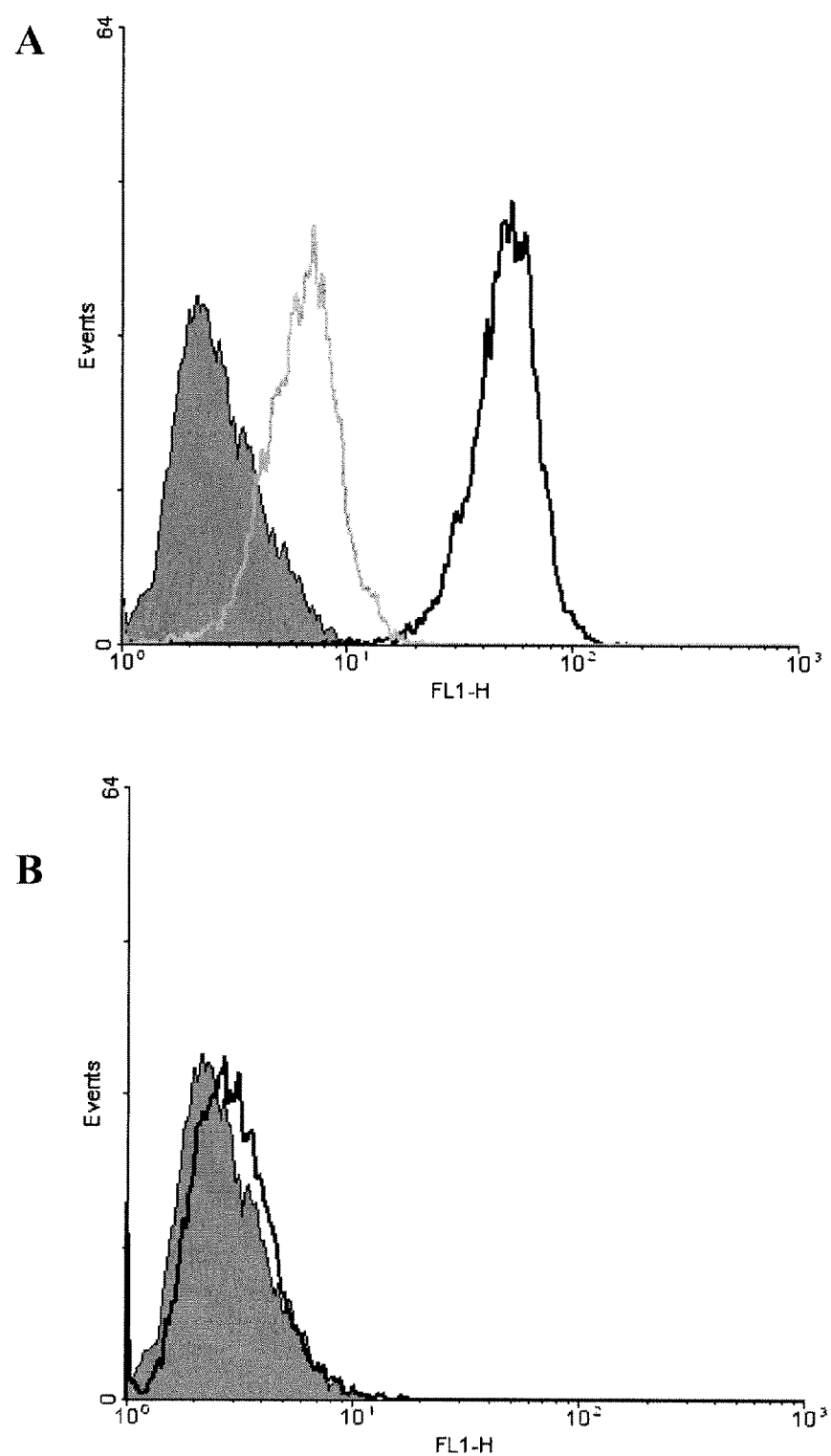

FIG. 13: Flow cytometry analysis of chH23-ZZ-PE38 immunoconjugate.

Cellular ErbB2 binding specificity was evaluated on human breast adenocarcinoma SKBR3 cell line. Cells were incubated with 10 µg/ml of chFRP5-ZZ-PE38 (A) or control hIgG-ZZ-PE38 (B) for 1.5 h at 4° C. In (B), specific chFRP5-ZZ-PE38 binding was confirmed by incubation of the immunoconjugate in the presence or absence of 10-fold excess of un-conjugated chFRP5 IgG1 prior to incubation with the cells. Rabbit anti-PE sera mixed with FITC-labeled goat anti-rabbit were used for the detection of bound chFRP5-ZZ-PE38. Filled areas, negative control; black line, binding of specific antibody; grey line, competition for cell binding with chH23 IgG1.

Figure 14:
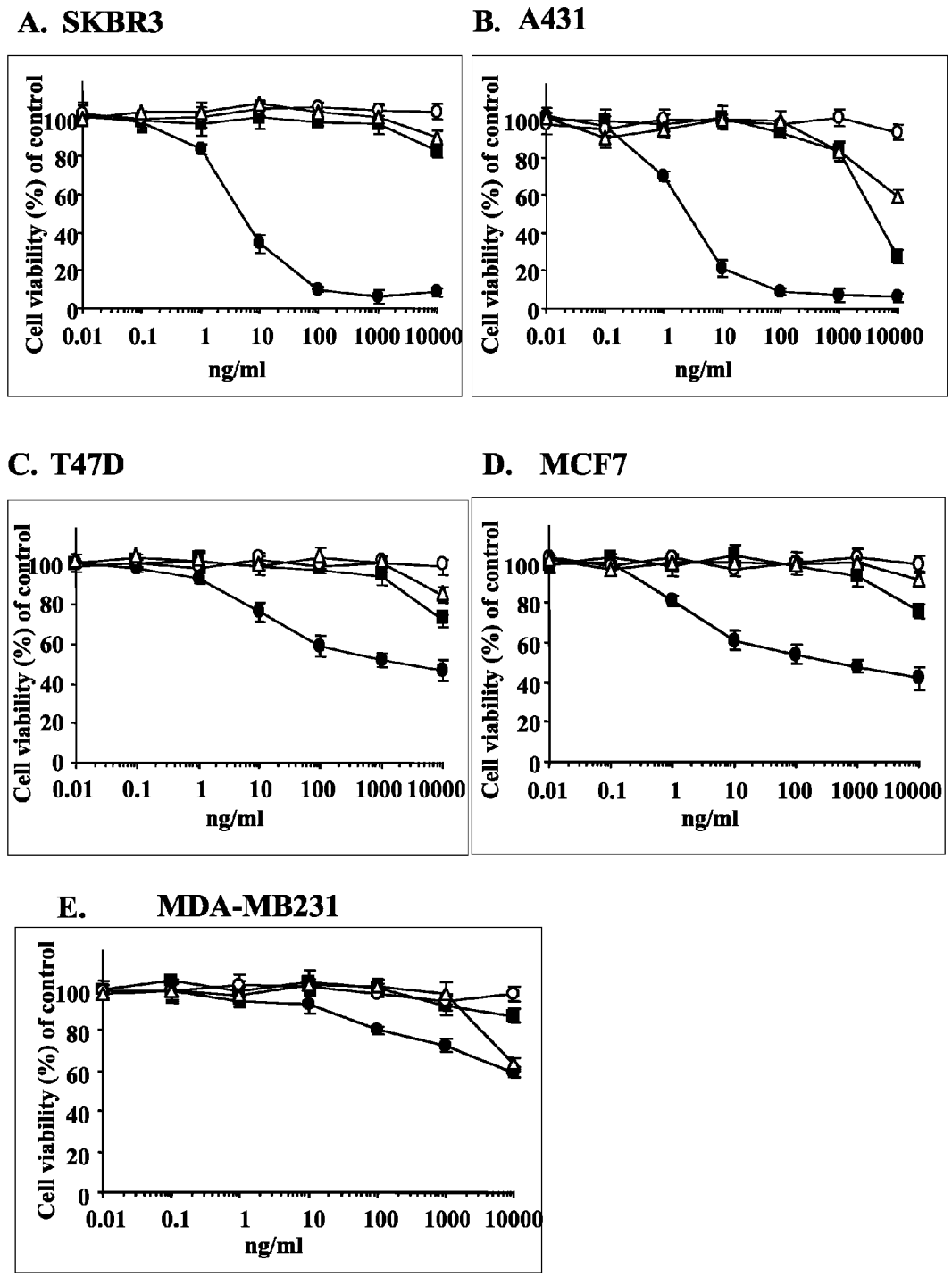

FIG. 14: Inhibition of the growth of human tumor cell lines by the chFRP5-ZZ-PE38.

SKBR3 (A), A431 (B), T47D (C), MCF7 (D) and MDA-MB231 (E) tumor cells were incubated for 48 h with the indicated concentrations of chFRP5-ZZ-PE38 (filled circles), hIgG-ZZ-PE38 (filled squares), chFRP5 IgG1 (open circles) or ZZ-PE38 (open triangles). The relative number of viable cells was determined using an enzymatic MTT assay and is indicated as the absorption at 570 nm. Each point represents the mean of a set of data determined in triplicate in three independent experiments. The results are expressed as percentage of living cells in comparison to the untreated controls that were processed simultaneously using the following equation: ($A_{570}$ of treated sample/$A_{570}$ of untreated sample)×100. The $IC_{50}$ values were defined as the immunoconjugate concentrations inhibiting cell growth by 50%. The error bars represent standard deviation of three independent experiments.

Figure 15:
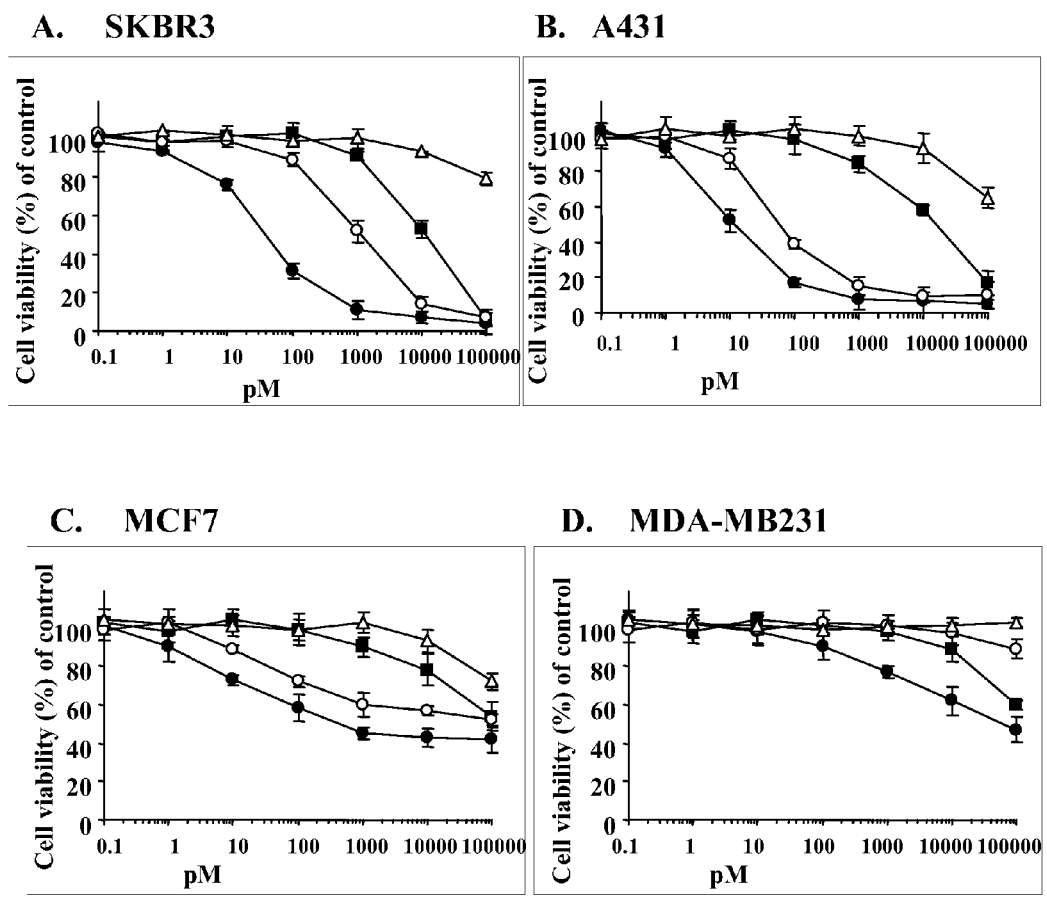

FIG. 15: Comparative cytotoxic activities of chFRP5-ZZ-PE38 and scFv(FRP5)-ETA.

SKBR3 (A), A431 (B), MCF7 (C) and MDA-MB231 (D) cells were incubated for 48 h with the indicated concentrations of chFRP5-ZZ-PE38 or scFv(FRP5)-ETA. To confirm specificity, both immunotoxins were incubated in medium assay with 100 µg/ml of chFRP5 IgG1. The relative number of viable cells was determined using an enzymatic MTT assay and is indicated as the absorption at 570 nm. Filled circles, chFRP5-ZZ-PE38; filled squares, chFRP5-ZZ-PE38 incubated in the presence of 100 µg/ml competing chFRP5 IgG1; open circles, scFv(FRP5)-ETA; open triangles, scFv(FRP5)-ETA incubated in the presence of 100 µg/ml competing chFRP5 IgG1. Each point represents the mean of a set of data determined in triplicate in three independent experiments. The error bars represent standard deviation of three independent experiments.

FIG. 16: Effect of competing IgGs on cell-killing activity of chFRP5-ZZ-PE38.

SKBR3 (A) and A431 (B) cells were incubated for 48 h with the indicated concentrations of chH23-ZZ-PE38 in the presence or absence of 100 µg/ml of HERCEPTIN (trastuzumab) mAb or chFRP5 IgG1 in assay medium. The relative number of viable cells was determined using an enzymatic MTT assay and is indicated as the absorption at 570 nm. Filled circles, chFRP5-ZZ-PE38; filled squares, chFRP5-ZZ-PE38 incubated in the presence of 100 µg/ml competing HERCEPTIN (trastuzumab) mAb; open circles, chFRP5-ZZ-PE38 incubated in the presence of 100 µg/ml competing chFRP5 IgG1. Each point represents the mean of a set of data determined in triplicate in three independent experiments. The error bars represent standard deviation of three independent experiments.

Figure 17:
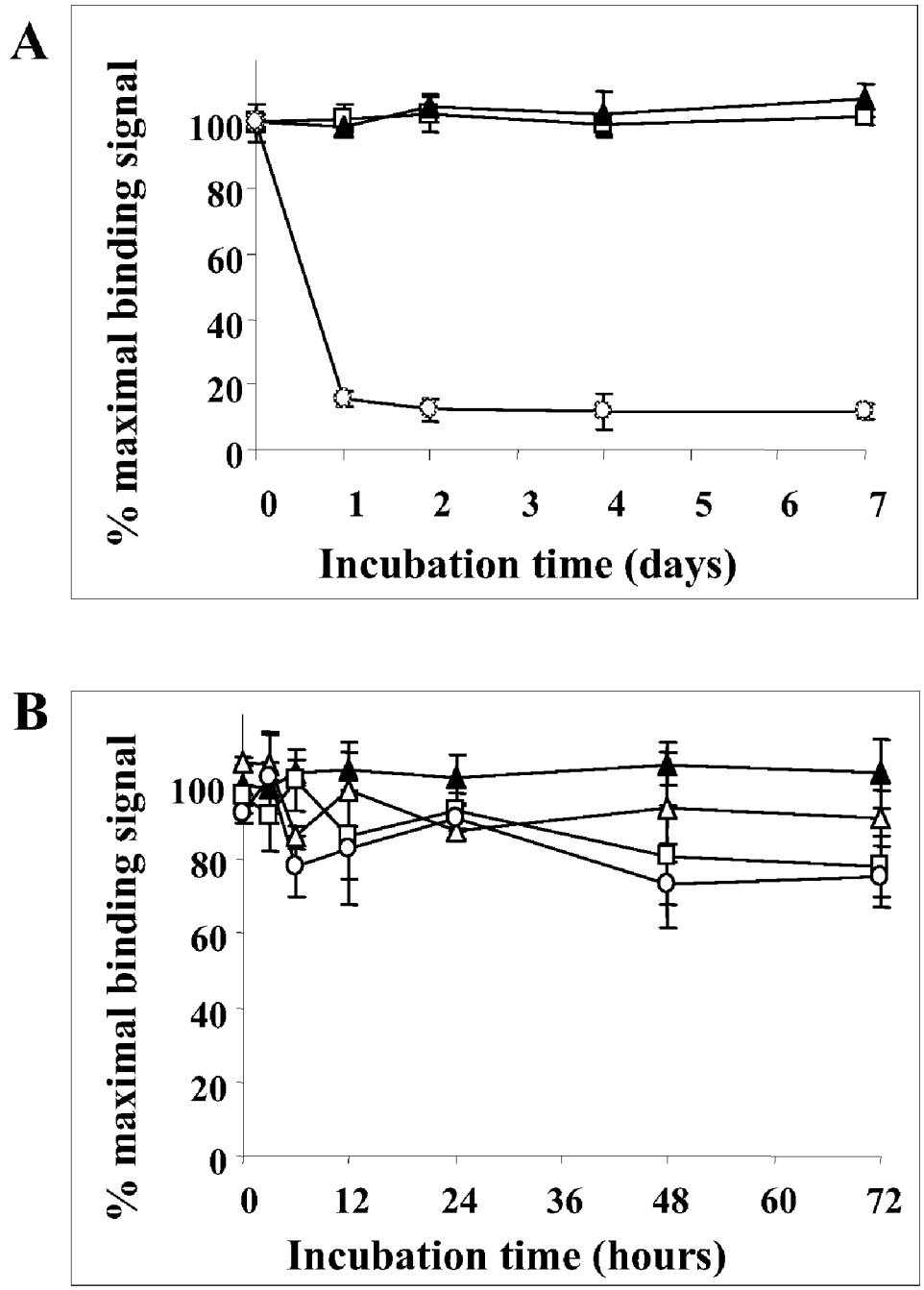

FIG. 17: Analysis of ErbB2 binding by chH23-ZZ-PE38 following preincubation with competitors for ZZ binding.

Cellular ErbB2 binding was evaluated by whole-cell ELISA on human breast adenocarcinoma SKBR3 cell line followed preincubation of chFRP5-ZZ-PE38 at 37° C. in PBS with (A) 10-fold molar excess of protein-A purified human IgG for periods up to 7 days, or (B) incubation in 100% human serum of three individual donors. Rabbit anti-PE sera mixed with HRP-conjugated goat anti-rabbit were used for the detection of bound chFRP5-ZZ-PE38, while HRP-labeled goat anti-human was used for the detection of bound chFRP5. The ELISA was developed using the chromogenic HRP substrate TMB. In A: Open squares, chFRP5; filled triangles, chFRP5-ZZ-PE38; open circles, chFRP5-ZZ-PE38 incubated in the presence of ×10 molar excess of competing human IgG. In (B): open squares, open triangles and open circles represent chFRP5-ZZ-PE38 incubated in the presence of ×10 molar excess of competing human IgG from three different sources respectively. The error bars represent standard deviations of three independent experiments.

FIGS. 18A and B: Analysis of crosslinked chFRP5-ZZ-PE38.

A. Analysis of crosslinked chFRP5-ZZ-PE38 by SDS/PAGE. MW, molecular mass marker, lane 1, purified, untreated chFRP5-ZZ-PE38 immunoconjugate (3 µg); lane 2, unpurified crosslinked chFRP5-ZZ-PE38 immunoconjugate (3 µg). Proteins were separated on a 10%/SDS polyacrylamide gel under reducing conditions and visualized by staining with GELCODE BLUE® dye. Arrows mark the position of ZZ-P38 and chFRP5 heavy and light chains.

B. Analysis of ErbB2 binding by crosslinked-chH23-ZZ-PE38 in whole-cell ELISA. Comparative cellular ErbB2 binding was evaluated by whole-cell ELISA on human breast adenocarcinoma SKBR3 cells following preincubation of crosslinked-chFRP5-ZZ-PE38 and chFRP5-ZZ-PE at 37° C. for 24 h in the presence or absence of 10-fold molar excess of protein-A purified human IgG antibodies or alternatively, in 100% human serum. Rabbit anti-PE sera mixed with HRP-conjugated goat anti-rabbit were used for the detection of bound immunotoxins. Filled squares, chFRP5-ZZ-PE38; filled triangles, chFRP5-ZZ-PE38 following incubation with competing human serum; filled circles, chFRP5-ZZ-PE38 following incubation with competing human IgG; open squares, crosslinked chFRP5-ZZ-PE38; open triangles, crosslinked chFRP5-ZZ-PE38 following incubation with competing human serum; open circles, crosslinked chFRP5-ZZ-PE38 following incubation with competing human IgG. The ELISA was developed using the chromogenic HRP substrate TMB. The error bars represent standard deviations of three independent experiments.

FIG. 19: Cell killing activity of crosslinked-chH23-ZZ-PE38 following preincubation with human IgG or human serum.

Crosslinked-chH23-ZZ-PE38 and chH23-ZZ-PE38 were preincubated at 37° C. for 24 h in the presence or absence of (A) 10-fold molar excess of protein-A purified human IgG antibodies, or (B) incubated for 24 h in 100% human serum before being evaluated for their cytotoxic activity on A431 cells. The relative number of viable cells was determined using an enzymatic MTT assay and is indicated as the absorption at 570 nm. Filled circles, chFRP5-ZZ-PE38; filled squares, chFRP5-ZZ-PE38 following incubation with competitor; open circles, crosslinked chFRP5-ZZ-PE38; open squares, crosslinked chFRP5-ZZ-PE38 following incubation with competitor. Each point represents the mean of a set of data determined in triplicate in three independent experiments. The error bars represent standard deviations of three independent experiments.

FIG. 20: Determination of chFRP5-ZZ-PE38 and scFv (FRP5)-ETA serum concentration by dot-blot analysis.

100 µl of serum samples diluted 1:100 in PBS of mice injected with chFRP5-ZZ-PE38 (A) or scFv(FRP5)-ETA (B) were applied in a two-fold dilution series as dots onto a nitrocellulose filter alongside a two-fold dilution series of 100 ng/ml of chFRP5-ZZ-PE38 (A) and scFv(FRP5)-ETA (B) that were used to determine the immunotoxin concentration in each serum sample. Rabbit anti-PE mixed with HRP-conjugated goat anti-rabbit were used for the detection of the immunotoxins. The membrane was developed using ECL reagents and exposure to X-ray film.

Figure 21:
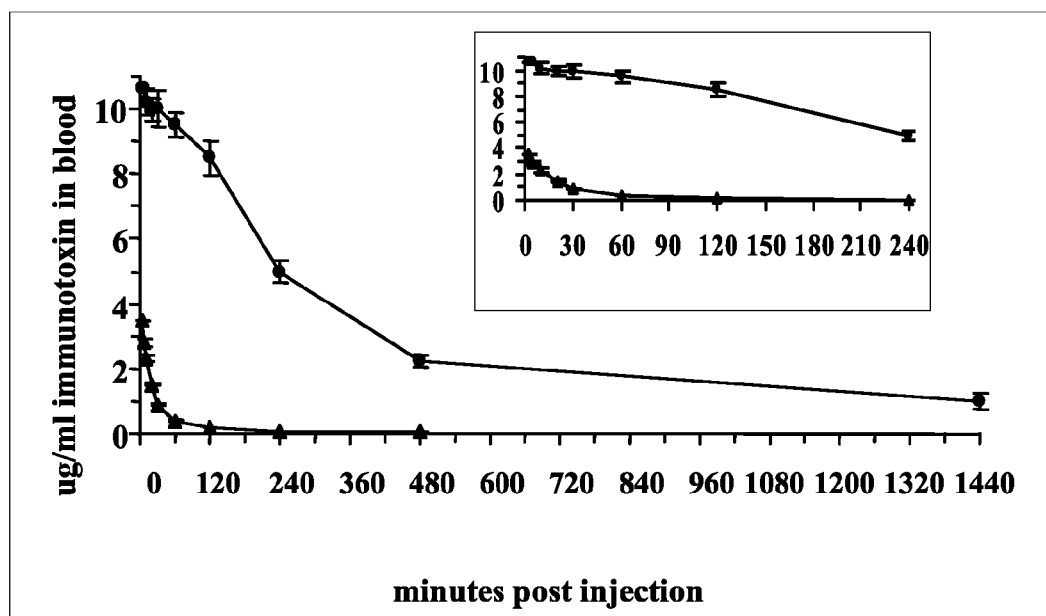

FIG. 21: Blood levels of chFRP5-ZZ-PE38 and scFv (FRP5)-ETA in mice.

Female BALB/c mice were given a single molar equivalent i.v. dose of 15 µg chFRP5-ZZ-PE38 or 5 µg scFv(FRP5)-ETA by injection into the tail vein. Blood samples were drawn from the orbital vein of mice injected with scFv(FRP5)-ETA at 2, 5, 10, 20, 30, 60, 120 and 240 min after injection and at 2, 5, 10, 20, 30, 60, 120, 240, 480 and 1440 min for mice injected with chFRP5-ZZ-PE38. The immunotoxins blood levels at each time point was calculated by dot-blot analysis of serum dilutions and by measuring cell-killing activity of serum dilutions on A431 cells using MTT assay. Results are the mean from two mice for each time point±SE. Filled circles, chFRP5-ZZ-PE38; filled triangles, scFv(FRP5)-ETA. Insert: expanded view of results from the first 4 hrs.

Figure 22:
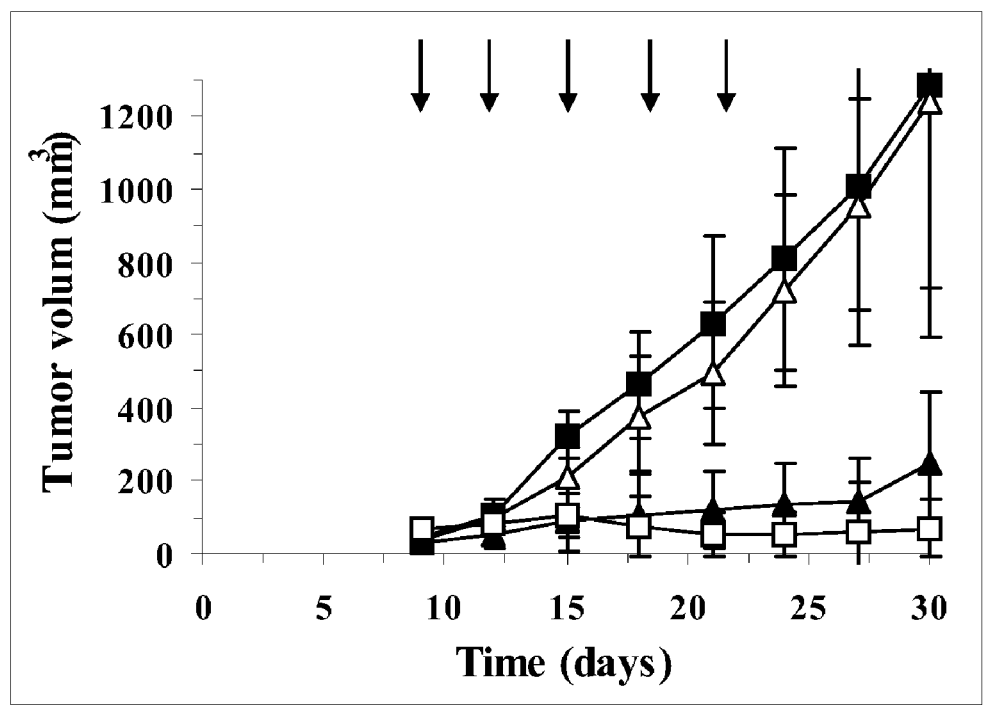

FIG. 22: Antitumor effect of chFRP5-ZZ-PE38 and scFv (FRP5)-ETA on the in vivo growth of A431 tumor xenografts in nude mice.

Groups of 3-5 mice were given s.c. injections of $1.5 \times 10^6$ A431 cells on day 0, and were treated by i.v. injections of 0.5 mg/kg chFRP5-ZZP-E38 (open squares) or 0.25 mg/kg chFRP5-ZZ-PE38 (filled triangles) or scFv(FRP5)-ETA (open triangles) on days 9,12,15,18 and 21 marked by arrows when tumors were established. Control mice were treated with PBS (filled squares). Tumor size was measured at the indicated time points and tumor volumes were calculated. The mean values for each group are shown and the standard deviation is represented by error bars.

Figure 23:
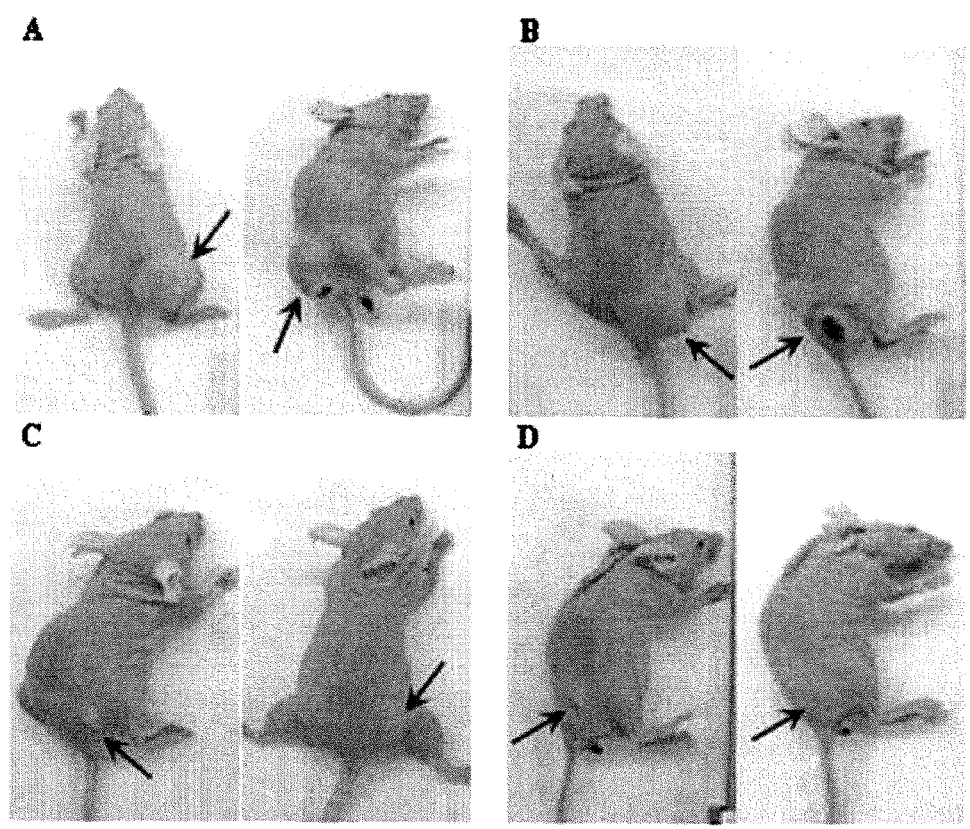

FIG. 23: Xenograft-bearing nude mice photographed on day 30 of the anti-tumor experiment.

Shown are 2 mice of each group: A, control (PBS injected) mice. B, scFv(FRP5)-ETA (0.25 mg/kg) injected mice. C, chFRP5-ZZ-PE38 (0.25 mg/kg) injected mice. D, chFRP5-ZZ-PE38 (0.5 mg/kg) injected mice. Arrows mark location of tumors.

DETAILED DESCRIPTION OF THE INVENTION

The present invention relates to a polynucleotide construct encoding a fusion protein, the polynucleotide construct comprising a first sequence encoding an immunoglobulin Fc-binding domain, for example the synthetic Fc-binding domain derived from *Staphylococcus aureus* protein A denoted as "ZZ", and a second sequence encoding a truncated form of *Pseudomonas* exotoxin (PE), and fusion proteins encoded by the construct. The invention further relates to the preparation of immunotoxin conjugates using the recombinant fusion protein ZZ-PE and efficiently internalizing IgGs, IgG complexes and Fc-fusion proteins. Immunocomplexes incorporating ZZ-PE and efficiently internalizing IgG are highly specific and potent immunotoxins.

Definitions

As used herein, an "immunoglobulin Fc-binding domain" refers to a protein or peptide which binds the Fc region of an immunoglobulin molecule. For example, *S. aureus* protein A (SPA) and various fragments thereof bind a specific region on the Fc of human IgG1 and other Ig molecules.

The terms "polynucleotide construct" and "polynucleotide sequence" are used herein interchangeably to refer to a polymer of nucleotides, such as deoxyribonucleotides, ribonucleotides, or modified forms thereof in the form of an individual fragment or as a component of a larger construct, in a single strand or in a double strand form. The polynucleotides to be used in the invention include sense and antisense polynucleotide sequences of DNA or RNA as appropriate to the goals of the therapy practiced according to the invention. The DNA or RNA molecules may be complementary DNA (cDNA), genomic DNA, synthesized DNA or a hybrid thereof or an RNA molecule such as mRNA. Accordingly, as used herein, the terms "DNA construct", "gene construct" and "polynucleotide" are meant to refer to both DNA and RNA molecules.

The terms "recombinant fusion protein" and "fusion protein" are used herein interchangeably to refer to a protein produced by recombinant technology which comprises segments i.e. amino acid sequences, from heterologous sources, such as different proteins or different organisms. The segments are joined either directly or indirectly to each other via peptide bonds. By indirect joining it is meant that an intervening amino acid sequence, such as a peptide linker is juxtaposed between segments forming the fusion protein. Accordingly, the fusion protein of the invention may optionally comprise a peptide linker. The fusion protein may contain two or more segments. In the case of a fusion protein having more than two segments, some adjacent segments may be directly joined without any peptide linker, while other adjacent segments may be joined via a peptide linker As used herein, "recombinant fusion protein" and "recombinant protein" include reference to a protein produced using cells that do not have, in their native state, an endogenous copy of the DNA able to express the protein. The cells produce the recombinant protein because they have been genetically altered by the introduction of the appropriate isolated nucleic acid sequence. In accordance with the invention, a recombinant fusion protein is encoded by the polynucleotide construct as disclosed herein. The term also includes reference to a cell, or nucleic acid, or vector, that has been modified by the introduction of a heterologous nucleic acid or the alteration of a native nucleic acid to a form not native to that cell, or that the cell is derived from a cell so modified. Thus, for example, recombinant cells express genes that are not found within the native (non-recombinant) form of the cell, express mutants of genes that are found within the native form, or express native genes that are otherwise abnormally expressed, underexpressed or not expressed at all.

The term "antibody" as used herein refers to immunoglobulin (Ig) molecules and immunologically active portions of Ig molecules, i.e. molecules that contain an antigen binding site that specifically binds (immunoreacts with) an antigen. Such antibodies include, but are not limited to, polyclonal, monoclonal, chimeric, single chain, Fab, Fab' and F(ab')$_2$ fragments, and an Fab expression library. In general, antibody molecules obtained from humans relates to any of the classes IgG, IgM, IgA, IgE and IgD, which differ from one another by the nature of the heavy chain present in the molecule. Certain classes have subclasses as well, such as IgG1, IgG2, and others. Furthermore, in humans the light chain may be a kappa chain or a lambda chain. Reference herein to antibodies includes a reference to all such classes, subclasses and types of human antibody species.

The terms "selectively reactive", "specific binding", "specific recognition" and related grammatical forms thereof are used herein interchangeably to refer to the preferential association of an antibody, in whole or part, with a cell or tissue bearing a particular antigen and not to cells or tissues lacking that antigen. It is, of course, recognized that a certain degree of non-specific interaction may occur between an antibody and a non-target cell or tissue. Nevertheless, selective reactivity may be distinguished as mediated through specific recognition of the antigen. Although selectively reactive antibodies bind antigen, they may do so with low affinity. On the other hand, specific binding results in a much stronger association between the antibody and cells bearing the antigen than between the bound antibody and cells lacking the antigen. Specific binding typically results in greater than 2-fold, preferably greater than 5-fold, more preferably greater than 10-fold and most preferably greater than 100-fold increase in amount of bound antibody (per unit time) to a cell or tissue bearing the antigen recognized by the preferred antibody as compared to a cell or tissue lacking expression of the antigen. Specific binding to a protein under such conditions requires an antibody that is selected for its specificity for a particular protein. A variety of immunoassay formats are appropriate for selecting antibodies specifically immunoreactive with a particular protein. For example, solid-phase ELISA immunoassays are routinely used to select monoclonal antibodies specifically immunoreactive with a protein. See Harlow & Lane, Antibodies, A Laboratory Manual, Cold Spring Harbor Publications, New York (1988), for a description of immunoassay formats and conditions that can be used to determine specific immunoreactivity.

*Staphylococcus aureus* protein A (also referred to herein as "protein A", "Staphlococcal protein A" and "SPA") in its native form is a 42 kD polypeptide which exhibits strong binding to the Fc region of many IgG molecules, including human IgG1, IgG2 and IgG4 and mouse IgG2a and IgG2b, without interfering with the antigen binding site (Surolia et al Trends Biochem. Sci. 7(1981):74; Lindmark et al, J. Immunol. Meth. 62(1983):1).

The fusion protein according to the invention comprises an immunoglobulin Fc-binding domain. A suitable immunoglobulin Fc-binding domain is one which is derived from *S. aureus* protein A, for example the tandem repeated, mutated form of domain B termed ZZ (SEQ ID NO:2). Disclosures of derivatives of protein A are provided for example in Nilsson et al 1987, Protein Eng. 1, 107-13; Nilsson et al 1996, Protein Eng. 1, 107-13, and Brasted and Wells (1996) Proc Natl Acad Sci USA 93, 5688-92. The Fc-binding domain may be present in the fusion protein in single or multiple copies. The immunoglobulin Fc-binding domain may be an anti-Fc single-chain antibody, as disclosed for example in Azriel-Rosenfeld et al 2004, J Mol Biol 335, 177-92.

*Pseudomonas* exotoxin (PE) in its native form is a monomeric protein of 613 amino acids (molecular weight 66 kD) secreted by *Pseudomonas aeruginosa*, which inhibit protein synthesis in eukaryotic cells through the inactivation of elongation factor 2 (EF-2) by catalyzing its ADP-ribosylation i.e. the transfer of the ADP ribosyl moiety of oxidized NAD onto EF-2.

The native PE sequence as disclosed for example in U.S. Pat. No. 5,602,095, is provided herein as SEQ ID NO:4. The exotoxin contains three structural domains that act in concert to cause cytotoxicity. Domain Ia (amino acids 1-252) mediates cell binding. Domain II (amino acids 253-364) is responsible for translocation into the cytosol and domain III (amino acids 400-613) mediates ADP ribosylation of elongation factor 2. The function of domain Ib (amino acids 365-399) remains undefined, although a large part of it, amino acids 365-380, can be deleted without loss of cytotoxicity. See Siegall et al., J. Biol. Chem. 264:14256-14261, 1989.

The term "*Pseudomonas* exotoxin" ("PE") as used herein refers as appropriate to a full-length native (naturally occurring) PE or to a PE that has been modified, for example a deletion mutant.

As used herein, the term "a truncated form of *Pseudomonas* exotoxin" refers to any mutant form of PE which comprises a deletion of a portion of the native sequence of PE and retains cytotoxic activity. Thus, the PE used in the invention disclosed herein includes fragments of the native sequence, internal deletion mutants, conservatively modified variants of native PE and fragments thereof, and combinations thereof, with the condition that such forms of PE are cytotoxic with or without subsequent proteolytic or other processing in the target cell (e.g., as a protein or pre-protein). Such mutant forms may further comprise additional sequences, modified amino acids and other variations as are known in the art.

According to various embodiments, truncated forms of PE for use in the invention include, without limitation PE38 (SEQ ID NO:3); PE38KDEL (SEQ ID NO:23); PE38RDEL (SEQ ID NO:24); PE37 (SEQ ID NO:25) and PE40 (SEQ ID NO:26).

PE38 is composed of amino acids 253-364 and 381-613 of native PE which is activated to its cytotoxic form upon processing within a cell (see e.g., U.S. Pat. No. 5,608,039, and Pastan et al 1997, Biochim. Biophys. Acta 1333:C1-C6). PE37 corresponds to amino acids 281-613 of native PE linked to an initial methionine residue, as disclosed for example in U.S. Pat. No. 5,602,095. PE38KDEL corresponds to amino acids 253-364 and 381-609 of native PE linked to the altered C-terminal sequence KDEL, as disclosed for example in Brinkmann et al 1991, Proc Nat Acad Sci USA 88:8616-8621. PE38RDEL corresponds to amino acids 253-364 and 381-609 of native PE linked to the altered C-terminal sequence RDEL as disclosed for example in Kreitman and Pastan 1995, Biochem J 307:29-37. PE40 corresponds to amino acids 253-613 of native PE U.S. Pat. No. 6,051,405.

The invention also encompasses additional truncated forms of PE and variants there of as are known in the art inter alia in the publications cited supra.

The fusion protein of the invention comprises an immunoglobulin Fc-binding domain, for example the synthetic ZZ domain derived from *S. aureus* protein A (SEQ ID NO:2), and a truncated form of *Pseudomonas* exotoxin such as PE38 (SEQ ID NO:3). In a currently preferred embodiment, the fusion protein consists of ZZ (SEQ ID NO:2) and PE38 (SEQ ID NO:3) joined by a peptide linker (SEQ ID NO:27). The two segments may be directly linked, or indirectly linked via an intervening sequence such as a peptide linker. It is generally preferable that any intervening sequences are substantially devoid of any biological activity. A suitable peptide linker is for example one having from about four to about 20 amino acids. It may in some cases be preferable that the linker is composed substantially of neutral amino acids. A suitable linker may for example have the sequence of SEQ ID NO:27. Many peptide linkers are known in the art and may be used alternately or additionally.

In a currently preferred embodiment, the fusion protein consists of ZZ (SEQ ID NO:2) and PE38 (SEQ ID NO:3) joined by a peptide linker (SEQ ID NO:27). In a currently preferred embodiment, the fusion protein is ZZ-PE38 and has the amino acid sequence of SEQ ID NO:1. A nucleotide sequence which encodes ZZ-PE38 is SEQ ID NO:6.

The term "monoclonal antibody" (mAb) as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. mAbs thus contain an antigen binding site capable of immunoreacting with a particular epitope of the antigen characterized by a unique binding affinity for it.

Monoclonal antibodies can be prepared using hybridoma methods, such as those described by Kohler and Milstein, 1975, Nature, 256:495. In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

Additional types of antibodies suitable for use in the invention include humanized antibodies and human antibodies. These antibodies are suitable for administration to humans without engendering an immune response by the human against the administered immunoglobulin. Humanized forms of antibodies are chimeric immunoglobulins, immunoglobulin chains or fragments thereof (such as Fv, Fab, Fab', F(ab')$_2$ or other antigen-binding subsequences of antibodies) that are principally comprised of the sequence of a human immunoglobulin, and contain minimal sequence derived from a non-human immunoglobulin. Humanization can be performed following the method of Winter and co-workers (Jones et al., Nature, 321:522-525 (1986); Riechmann et al., Nature, 332: 323-327 (1988); Verhoeyen et al., Science, 239:1534-1536 (1988)), by substituting rodent CDRs or CDR sequences for the corresponding sequences of a human antibody. (See also U.S. Pat. No. 5,225,539). In some instances, Fv framework residues of the human immunoglobulin are replaced by corresponding non-human residues. Humanized antibodies can also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the framework regions are those of a human immunoglobulin consensus sequence. The humanized antibody optimally also will comprise at least a portion of an immunoglobulin constant region (Fc), typically that of a human immunoglobulin (Presta, 1992, Curr. Op. Struct. Biol., 2:593-596).

Fully human antibodies essentially relate to antibody molecules in which the entire sequence of both the light chain and the heavy chain, including the CDRs, arise from human genes. Such antibodies are termed "human antibodies", or "fully human antibodies" herein. Human monoclonal antibodies can be prepared by the trioma technique; the human B-cell hybridoma technique (see Kozbor, et al., 1983 Immunol Today 4: 72) and the EBV hybridoma technique to produce human monoclonal antibodies (see Cole, et al., 1985 In: Monoclonal Antibodies And Cancer Therapy, Alan R. Liss, Inc., pp. 77-96). Human monoclonal antibodies may be utilized in the practice of the present invention and may be produced by using human hybridomas (see Cote, et al., 1983. Proc Natl Acad Sci USA 80: 2026-2030) or by transforming human B-cells with Epstein Barr Virus in vitro (see Cole, et al., 1985 In: Monoclonal Antibodies And Cancer Therapy, Alan R. Liss, Inc., pp. 77-96).

In addition, human antibodies can also be produced using additional techniques, including phage display libraries (Hoogenboom and Winter, J. Mol. Biol., 227:381 (1991); Marks et al., J. Mol. Biol., 222:581 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in Marks et al. (Bio/Technology 10, 779-783 (1992)); Lonberg et al. (Nature 368 856-859 (1994)); Morrison (Nature 368, 812-13 (1994)); Fishwild et al, (Nature Biotechnology 14, 845-51 (1996)); Neuberger (Nature Biotechnology 14, 826 (1996)); and Lonberg and Huszar (Intern. Rev. Immunol. 13:65-93 (1995)).

Human antibodies may additionally be produced using transgenic nonhuman animals which are modified so as to produce fully human antibodies rather than the animal's endogenous antibodies in response to challenge by an antigen. (See PCT publication WO94/02602). The endogenous genes encoding the heavy and light immunoglobulin chains in the nonhuman host have been incapacitated, and active loci encoding human heavy and light chain immunoglobulins are inserted into the host's genome. The human genes are incorporated, for example, using yeast artificial chromosomes containing the requisite human DNA segments. An animal which provides all the desired modifications is then obtained as progeny by crossbreeding intermediate transgenic animals containing fewer than the full complement of the modifications. The preferred embodiment of such a nonhuman animal is a mouse, and is termed the XENOMOUSE (mice), as disclosed in PCT publications WO 96/33735 and WO 96/34096. This animal produces B cells which secrete fully human immunoglobulins. The antibodies can be obtained directly from the animal after immunization with an immunogen of interest, as for example, a preparation of a polyclonal antibody, or alternatively from immortalized B cells derived from the animal, such as hybridomas producing monoclonal antibodies. Additionally, the genes encoding the immunoglobulins with human variable regions can be recovered and expressed to obtain the antibodies directly, or can be further modified to obtain analogs of antibodies such as, for example, single chain Fv molecules.

The term "expression cassette" refers to a recombinant nucleic acid construct comprising an expression control sequence operatively linked to an expressible nucleotide sequence. An expression cassette generally comprises sufficient cis-acting elements for expression; other elements for expression can be supplied by the host cell or in vitro expression system.

The invention further provides a recombinant expression vector comprising a polynucleotide construct of the invention cloned into the expression vector. The term "expression vector" refers to a vector comprising an expression cassette. Expression vectors include all those known in the art, such as cosmids, plasmids (e.g., naked or contained in liposomes) and viruses that incorporate the expression cassette. An "expression plasmid" comprises a plasmid nucleotide sequence capable of directing a molecule of interest, which is operably linked to a promoter.

As used herein the term "operably linked" wherein referring to a first nucleic acid sequence which is operably linked with a second nucleic acid sequence refers to a situation when the first nucleic acid sequence is placed in a functional relationship with the second nucleic acid sequence. For instance, a promoter is operably linked to a coding sequence if the promoter effects the transcription or expression of the coding sequence. Generally, operably linked nucleic acid sequences are contiguous and, where necessary to join two protein coding regions, the open reading frames are aligned.

A "promoter" is a minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included (see e.g., Bitter et al 1987, Methods in Enzymology 153:516-544). For example, when cloning in bacterial systems, inducible promoters such as pL of bacteriophage lambda, plac, ptrp, ptac (ptrp-lac hybrid promoter) and the like may be used. In one embodiment, when cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) can be used. Promoters produced by recombinant DNA or synthetic techniques may also be used to provide for transcription of the nucleic acid sequences.

By "host cell" is meant a cell into which (or into an ancestor of which) has been introduced, by means of recombinant DNA techniques, the expression vector of the present invention. Transformation of a host cell with recombinant DNA may be carried out by conventional techniques as are well known to those skilled in the art. Where the host is prokaryotic, such as $E.\ coli$, cells which are competent for DNA uptake can be prepared from cells harvested after exponential growth phase and subsequently treated by using procedures well known in the art. For example, host cells can be made competent for transformation by $CaCl_2$, $MgCl_2$ or $RbCl$ treatment. Alternatively, cells can be made competent for electroporation by removing all traces of salt.

The invention further provides an immunotoxin conjugate (also referred to herein as an "immunoconjugate"), by which is meant a conjugate or complex comprising a targeting moiety, typically based on antibody-antigen recognition, and a toxic moiety which renders the immunotoxin cytotoxic to the cells of interest.

The targeting moiety is any biological substance endowed with specific binding properties towards a selected target cell. In one preferred embodiment, the targeting moiety is an antibody-based moiety, including, but not limited to: monoclonal antibodies, polyclonal antibodies, chimeric antibodies, humanized antibodies and antibody fragments such as recombinant antibody fragments, single-chain antibodies (scFv), single antibody variable domains, dsFv, Fab, F(ab')$_2$, and the like as are known in the art. Single-chain antibodies are small recognition units consisting of the variable regions of the immunoglobulin heavy ($V_H$) and light ($V_L$) chains which are connected by a synthetic linker sequence. Single antibody domain proteins (dAbs) are minimized antibody fragments comprising either an individual $V_L$ domain or an individual $V_H$ domain.

In another preferred embodiment, the targeting moiety is a peptide endowed with binding specificity towards the target cell (linear, circularly constrained or cyclic) or a short peptide selected from a library of short peptide sequences that is endowed with binding specificity towards the target cell. Methods for constructing libraries and using them for screening for ligands having an affinity to a selected target molecule or cell are known in the art. The targeting moiety may be a polypeptide, a carbohydrate, a lipid, a glycolipid, a saccharide, a nucleic acid and the like, which is able to selectively bind a target molecule on a target cell. For instance, the ligand may include known ligands of cell surface receptors, or any natural or synthetic derivative thereof. The toxic moiety is the portion of an immunotoxin, which renders the immunotoxin cytotoxic to cells of interest. The toxic moiety is preferably derived from a toxin of plant or bacterial origin.

Specific, non-limiting examples of toxins include, but are not limited to, abrin, ricin, *Pseudomonas* exotoxin (PE, such as PE37, PE38, and PE40), diphtheria toxin (DT), saporin, restrictocin, or modified toxins thereof, or other toxic agents that directly or indirectly inhibit cell growth or kill cells. For example, PE and DT are highly toxic compounds that typically bring about death through liver toxicity. PE and DT, however, can be modified into a form for use as an immunotoxin by removing the native targeting component of the toxin (e.g., domain Ia of PE or the B chain of DT) and replacing it with a different targeting moiety, such as an antibody.

According to the present invention, the toxic moiety is a component of a fusion protein wherein the fusion protein comprises a first segment which is an Fc-binding domain, and a second segment which is a truncated form of *Pseudomonas* exotoxin, as described herein. According to a currently preferred embodiment, the toxic moiety is the truncated form of *Pseudomonas* exotoxin denoted as PE38 which has the amino acid sequence of SEQ ID NO:3. In one embodiment, the toxic moiety PE38 is a component of the fusion protein ZZ-PE38 (SEQ ID NO:1).

The targeting moiety is preferably an antibody molecule, fragment or other derivative or antibody complex which includes the Fc region of IgG, in particular the protein A binding site present theron. Accordingly, the fusion protein of the invention may be complexed with the targeting moiety via interaction between the Fc-binding domain of the former and the Fc region of the latter, to thus form an immunotoxin conjugate. Such a conjugate formed by combination of the two entities may be referred to as an immuno complex.

In cases where the targeting moiety does not include the Fc region of IgG, for example in the case of an antibody fragment such as F(ab')$_2$, the targeting moiety may be synthetically fused to or conjugated with an Fc region, thereby conferring on the targeting moiety the ability to form a complex with the fusion protein.

The protein A mediated non-covalent interaction between the fusion protein and the antibody may be sufficiently tight to enable use of the complex as an immunotoxin without further manipulation. In some cases however, it may be useful to introduce covalent bonds between the two entities, for example by forming a chemically conjugated complex or a cross-linked complex.

"Covalent association", "covalent bond" and associated grammatical forms, such as "covalently associated" and "covalently bound" respectively, refer interchangeably to an intermolecular association or bond which involves the sharing of electrons in the bonding orbitals of two atoms. "Non-covalent association", "non-covalent bond" and associated grammatical forms refer interchangeably to intermolecular interaction among two or more separate molecules or molecular entities which does not involve a covalent bond.

Intermolecular interaction is dependent upon a variety of factors, including, for example, the polarity of the involved molecules, and the charge (positive or negative), if any, of the involved molecules. Non-covalent associations are selected from ionic interactions, dipole-dipole interactions, van der Waal's forces, and combinations thereof.

Methods for chemical conjugation and cross-linking are known in the art. A number of reagents capable of cross-linking molecules such as peptides are known in the art, including for example, azidobenzoyl hydrazide, N-[4-(p-azidosalicylamino)butyl]-3'-[2'-pyridyldithio]propionamide), bis-sulfosuccinimidyl suberate, dimethyladipimidate, disuccinimidyltartrate, N-.gamma.-maleimidobutyryloxysuccinimide ester, N-hydroxy sulfosuccinimidyl-4-azidobenzoate, N-succinimidyl [4-azidophenyl]-1,3'-dithiopropionate, N-succinimidyl [4-iodoacetyl]aminobenzoate, glutaraldehyde, formaldehyde and succinimidyl 4-[N-maleimidomethyl]cyclohexane-1-carboxylate.

According to one embodiment, an immunotoxin comprises a complex of the fusion protein of the invention and an antibody, wherein the antibody is capable of specifically binding an antigen expressed on the surface of a target cell. In a preferred embodiment, the antibody is capable of being internalized into the target cell.

The target cell may be a cancer cell or a pathogen infected cell. The pathogen may be a parasite or a virus.

The antigen targeted by the targeting antibody may be a tumor-associated antigen, a pathogen-associated antigen, a parasite-associated antigen or a virus-associated antigen. Examples of tumor-associated antigens include without limitation MUC1 and ErbB2. The cancer cell may be that of a cancer at a site selected from the group consisting of lung, colon, rectum, breast, ovary, prostate gland, head, neck, bone, kidney, liver, skin and the immune system.

It is intended that the immunotoxin delivers a toxic moiety to the target cells, and not to cells which are healthy and or found in other sites of an organism. Accordingly, the desired toxicity is in relation to a specific tissue or cell set. In contrast, the terms "excessive toxicity", "undesired toxicity" and the like refer to toxicity against non-target cells.

The invention further provides a method for selectively killing a target cell in a subject in need thereof, involving use of the recombinant fusion protein described herein. Various methods, such as library screening, are known in the art for obtaining antibodies having specificity for antigens of interest. Various candidate antibodies may be obtained by such methods. The ability of one or more candidate antibodies to be internalized into a target cell may then be assessed to determine if any particular antibody may be used as the targeting component of a potential immunotoxin. Once such an internalizing antibody has been selected, it may be combined with the fusion protein described herein so as to form an immunotoxin complex. The immunotoxin complex may be formulated into a pharmaceutical composition for administering to cells of the subject (either in vivo or ex vivo), thereby selectively killing the target cell in the subject.

The subject may be a mammal, in particular a human.

In one embodiment, the target cell is a cancer cell. In one embodiment, the cancer cell is from a site selected from the group consisting of lung, colon, rectum, breast, ovary, prostate gland, head, neck, bone, kidney, liver, skin and the immune system. In one embodiment, the cancer cell is a breast cancer cell.

Exposure of the target cells to the immunotoxin complex may be carried out by any of a number of routes, including without limitation, intravenous, intraperitoneal, subcutaneous, intramuscular and intralymphatic. As described herein, the complex may be one in which the antibody and the fusion protein are covalently associated.

The conjugates and complexes provided herein are useful in the treatment and prevention of various diseases, syndromes and disorders, including, but not limited to: tumors, such as melanoma, ovarian cancer, neuroblastoma, pterygii, secondary lens clouding and the like and autoimmune diseases.

As used herein, the term "tumor-associated antigen" refers to an antigen which is found on or expressed by a tumor cell, but which also may be found on or expressed by other non-cancerous cells, for example, at over-expressed or developmentally untimely levels. A tumor-associated antigen encompasses those associated with solid tumors and fluid tumors such as ascites fluid produced by ovarian cancer, pleural effusion produced by lung carcinomas, and nonsolid hematologic tumors. The term "tissue-specific" refers to an antigen which is found mainly on a particular tissue type.

The term "effective amount" as used herein means that amount of a pharmaceutical agent or composition necessary to achieve the desired specific effect, for example against a target cell and/or in amelioration of a specific disease state.

As used herein, "treatment" means any manner in which the symptoms of a condition, disorder or disease are ameliorated or otherwise beneficially altered. Treatment also encompasses any pharmaceutical use of the compositions herein. As used herein, "amelioration" of the symptoms of a particular disease or disorder refers to any lessening, whether permanent or temporary, lasting or transient, that can be attributed to or associated with administration of the composition.

In one embodiment, the immunoconjugates comprising the polynucleotide construct of the present invention may be used to treat tumors. In these diseases, cell growth is excessive or uncontrolled. Tumors suitable for treatment within the context of this invention include, but are not limited to, breast tumors, gliomas, melanomas, prostate cancer, hepatomas, sarcomas, lymphomas, leukemias, ovarian tumors, thymomas, nephromas, pancreatic cancer, colon cancer, head and neck cancer, stomach cancer, lung cancer, mesotheliomas, myeloma, neuroblastoma, retinoblastoma, cervical cancer, uterine cancer, and squamous cell carcinoma of skin. For such treatments, ligands can be chosen to bind to cell surface receptors that are generally preferentially expressed in tumors (e.g. MUC-1 and ErbB2). Through delivery of the compositions of the present invention, unwanted growth of cells may be slowed or halted, thus ameliorating the disease. The methods utilized herein specifically target and kill or halt proliferation of tumor cells having receptors for the ligand on their surfaces.

The immunoconjugate can be administered to a subject in any form or mode which makes the compound bioavailable in effective amounts, including oral and parenteral routes. For example, immunoconjugates can be administered orally, parenterally, subcutaneously, intravenously, intramuscularly, transdermally, intraperitoneally, intralesionally, nasally, rectally and the like. One skilled in the art of preparing formulations can readily select the proper form and mode of administration depending upon the particular characteristics of the compound selected, the disease state to be treated, the stage of the disease, and other relevant circumstances.

The immunoconjugate can be administered alone or in the form of a pharmaceutical composition in combination with pharmaceutically acceptable carriers or excipients, the proportion and nature of which are determined by the solubility and chemical properties of the compound selected, the chosen route of administration, and standard pharmaceutical practice. The compounds of the invention, while effective themselves, may be formulated and administered in the form of their pharmaceutically acceptable acid addition salts for purposes of stability, convenience of crystallization, increased solubility and the like.

The pharmaceutical compositions comprising the immunoconjugate are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral or parenteral use and may be administered to the subject in the form of tablets, capsules, suppositories, solution, suspensions, or the like.

The pharmaceutical compositions comprising the immunoconjugate may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 1% of the compound of the invention, the active ingredient, but may be varied depending upon the particular form and may conveniently be between 1% to about 70% of the weight of the unit. The amount of the compound present in compositions is such that a suitable dosage will be obtained. Preferred compositions and preparations according to the present invention are prepared so that an oral dosage unit form contains between 1.0-300 milligrams of the immunoconjugate.

The tablets, pills, capsules, troches and the like may also contain one or more of the following constituents: binders such as microcrystalline cellulose, gum tragacanth or gelatin; excipients such as starch or lactose; disintegrating agents such as alginic acid, PRIMOGEL, corn starch and the like; lubricants such as magnesium stearate; glidants such as colloidal silicon dioxide; sweetening agents such as sucrose or saccharin; flavoring agents such as peppermint, methyl salicylate or orange flavoring. When the dosage unit form is a capsule, it may contain, in addition to materials of the above type, a liquid carrier such as polyethylene glycol or fatty oil. Other dosage unit forms may contain other various materials which modify the physical form of the dosage unit, for example, as coatings. Thus, tablets or pills may be coated with sugar, shellac, or other enteric coating agents. Syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the immunoconjugate of the present invention may be incorporated into a solution or suspension. These preparations should contain at least 0.1% of the immunotoxin of the invention, but may be varied to be between 0.1 and about 50% of the weight thereof. The amount of the immunotoxin present in such compositions is such that a suitable dosage will be obtained. Preferred compositions and preparations according to the present invention are prepared so that a parenteral dosage unit contains between 1.0 to 100 milligrams of the immunotoxin.

The solutions or suspensions may also include the one or more of the following constituents: sterile diluents such as water for injection, saline solution, fixed oils, polyethylene glycols, glycerin, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates; and agents for the adjustment of tonicity such as sodium chloride or dextrose. The parenteral preparation can be enclosed in ampules, disposable syringes or multiple dose vials made of glass or plastic.

According to yet another aspect, the invention provides a method for assessing whether an antibody specific for a cell surface antigen is internalized into target cells expressing the antigen, the assay comprising:
a. providing a recombinant fusion protein, wherein the fusion protein comprises a first segment which is the ZZ Fc-binding domain derived from *S. aureus* protein A and a second segment which is PE38 derived from *Pseudomonas* exotoxin;
b. selecting at least one antibody specific for the cell surface antigen present on the target cells;
c. combining the antibody from (b) with the ZZ-PE38 fusion protein from (a) to form a complex; and
d. exposing the target cells to the complex of (c); and
e. assessing whether the complex is internalized into the target cells.

In this method, the fusion protein may be linked to a detectable moiety, such as a chromophore, a fluorescent label or a radiolabel, as is known in the art, in order to facilitate detection of internalization. This method employs the fusion protein as a "general purpose" reagent for large scale screening of candidate antibodies for their potential use as components of immunotoxins for targeted cell killing.

EXAMPLES

Materials and Methods

All chemicals used were of analytical grade and were purchased from Sigma (Israel). Unless stated otherwise, reactions were carried out at room temperature (about 25° C.). Unless stated otherwise, all the secondary antibodies (HRP or fluorescently-labeled) used were from Jackson Immunoresearch Laboratories, USA.

Construction of Mammalian IgH and IgL Expression Vectors and Cloning of Immunoglobulin H23 and FRP5 V Genes to be Expressed as Chimeric IgG1 Derivatives The heavy chain expression vector pMAZ-IgH was constructed on the backbone of pCMV/myc/ER/Neo (Invitrogen, USA). The human gamma 1 constant heavy chain region (CH1-CH3) was recovered by PCR from human lymphoid cDNA (Azriel-Rosenfeld et al 2004, J Mol Biol 335, 177-92)), using primers Hum-CH1-NheI-BACK (SEQ ID NO: 11) and Hum-CH3-Stop-XbaI-FOR (SEQ ID NO: 12; Table 1). After sequence validation, the human constant fragment was inserted via NheI/XbaI restriction sites into plasmid pCMV/myc/ER that had been linearized by the same enzymes, resulting in the removal of the myc-tag and the ER retention signal of pCMV/myc/ER leaving only the intrinsic signal peptide sequence. The murine H23 VH domain, derived from the anti MUC1 recombinant scFv form was amplified from plasmid pMAZ1-MuH23 (Mazor et al 2005, Mol Immunol 42, 55-69) using primers H23-VH-BssHII-BACK (SEQ ID NO: 13) and H23-VH-NheI-FOR (SEQ ID NO:14; Table 1). The PCR product was digested and introduced into the heavy chain vector as a BssHII/NheI fragment, the resulting vector was named pMAZ-IgH-H23 (SEQ ID NO:7).

TABLE 1

Primers

| Oligonucleotide | Sequence |
| --- | --- |
| Hum-CH1-NheI-BACK | 5'-CCACAGGCGCGCACTCCGAGGTC<br>CAACTGCAGGCTAGCACCAAGGGCCC<br>ATCGGTC-3'<br>SEQ ID NO: 11 |
| Hum-CH3-Stop-XbaI-FOR | 5'-TGTGTGTCTAGATTATTTACCCG<br>GGGACAGGG-3'<br>SEQ ID NO: 12 |
| H23-VH-BssHII-BACK | 5'-CCACAGGCGCGCACTCCGAAGTG<br>AAGCTTGAGGAGTCTGG-3'<br>SEQ ID NO: 13 |
| H23-VH-NheI-FOR | 5'-CTTGGTGCTAGCCGAAGAGACAG<br>TGACCAGAGT-3'<br>SEQ ID NO: 14 |
| H23-VK-BssHII-BAC | 5'-CCACAGGCGCGCACTCCCAGCTC<br>CAGATGACCCAGTC-3'<br>SEQ ID NO: 15 |
| H23-CL-STOP-XbaI-FOR | 5'-TCTCTCTCTAGATTAACACTCTC<br>CCCTGTTGAAGC-3'<br>SEQ ID NO: 16 |
| FRP5-VH-BACK | 5'-CCACAGGCGCGCACTCCCAGGTA<br>CAACTGCAGCAGTCTGG-3'<br>SEQ ID NO: 17 |
| FRP5-VH-FOR | 5'-CTTGGTGCTAGCAGAGGAAACGG<br>TGACCGTGGTCC-3'<br>SEQ ID NO: 18 |
| FRP5-VK-BACK | 5'-CCACAGGCGCGCACTCCCGACAT<br>CCAGCTGCCCAGTC-3'<br>SEQ ID NO: 19 |
| FRP5-VK-FOR | 5'-AGCCACCGTACGTTTGATCTCCA<br>ATTTTGTCCCCCGAGC-3'<br>SEQ ID NO: 20 |
| ZZ-Nco-FOR | 5'-CCGCTTCCATGGTAGACAACAAA<br>TTCAACAAAG-3'<br>SEQ ID NO: 21 |
| ZZ-Not-REV | 5'-GGGTTTAGCGGCCGCTTTCGGCG<br>CCTGAGCATCATTTAG-3'<br>SEQ ID NO: 22 |

The light chain expression vector pMAZ-IgL was constructed on the backbone of pcDNA3.1/Hygro (Invitrogen, USA). The plasmid DNA sequence between SspI and XbaI sites was replaced by an SspI/XbaI fragment recovered from plasmid pCMV/myc/ER introducing the latter multiple cloning site containing recognition for BssHII and BsiWI restriction enzymes to the resulting plasmid. Murine H23 light chain, derived from the anti MUC1 recombinant scFv form was amplified from plasmid pMAZ1-MuH23 (Mazor et al., 2005) using primers H23-VK-BssHII-BACK (SEQ ID NO: 15) and H23-CL-STOP-XbaI-FOR (SEQ ID NO: 16; Table 1) and introduced into the light chain vector as BssHII/XbaI fragment, the resulting vector was named pMAZ-IgL-H23 (SEQ ID NO:8).

All constructs were validated by DNA sequencing. The anti-ErbB2 FRP5 $V_H$ and $V_L$ domain were cloned into mammalian expression vectors as followed, DNA of plasmid pHEN1-FRP5(Fv) (Benhar et al., 2000) served as template in two PCR reactions. The $V_H$ region was amplified using primers FRP5-VH-BACK (SEQ ID NO: 17) and FRP5-VH-BACK FOR (SEQ ID NO:18; Table 1) with the former introducing BssHII site and the later NheI restriction site. The PCR product was inserted into plasmid pMAZ-IgH via BssHII/NheI sites. The resulting plasmid was named pMAZ-IgH-FRP5 (SEQ ID NO:9).

The FRP5 $V_K$ region was amplified using pHEN1-FRP5 (Fv) (Benhar et al., 2000) as template with primers FRP5-VK-BACK/FOR ((SEQ ID NOS: 19 and 20 respectively), introducing restriction sites BssHII at the 5' end and BsiWI at the 3' end, respectively. The PCR product was digested with restriction enzymes BssHII and BsiWI and cloned into plasmid pMAZ-IgL that had been linearized by the same enzymes. The resulting plasmid was named pMAZ-IgL-FRP5 (SEQ ID NO:10).

Cell Lines

Cell lines used were the human breast adenocarcinoma SKBR3 cell line, the human epidermoid carcinoma A431 cell line, the human breast carcinoma T47D and MCF7 cell lines, the human mammary carcinoma MDA-MB231 cell line and the human kidney HEK293 cell line. All cell lines were maintained in Dulbecco's modified Eagle medium (DMEM) containing 10% fetal calf serum (FCS), 2 µg/ml blasticidin (Invitrogen), penicillin, and streptomycin, unless specified otherwise.

Transfection of HEK293 Cells with Mammalian pMAZ-IgH and pMAZ-IgL Expression Vectors and Screening of Cell Culture Supernatants of Stable Clones Expressing Chimeric IgG1 Derivatives Using Dot-Blot Analysis Co-transfections of HEK293 cells with pMAZ-IgH and pMAZ-IgL expression vectors (for either chimeric H23 IgG, chH23, or for chimeric FRP5 IgG, chFRP5) were performed using FUGENE 6 nonliposomal transfection reagent (Roche, Brussels, Belgium) according to the manufacturer's instructions. Briefly, $10^6$ cells were seeded into 6 well plates and 24 hours after transfection, limiting dilutions were performed into 96-well plates medium containing 1.2 mg/ml of G418 and 200 µg/ml of hygromicin at a ratio of 1000 cells/well. Supernatants of single colonies were grown to near confluence on medium containing selection markers were tested for IgG1 secretion by dot-blot analysis and analyzed in ELISA for antibody binding to the corresponding antigen (MUC1 or ErbB2). To screen for IgG producing cells, 100 µl supernatants of stable clones were applied via a vacuum manifold onto a nitrocellulose filter using a dot-blot apparatus (Schleicher & Schuell. USA). After blocking the membrane with 5% (v/v) non-fat milk in Tris Buffered Saline (TBS) for 1 h at room temperature, the membrane was washed briefly with TBS and incubated with HRP conjugated goat anti human antibodies (×10,000 dilution in TBS/2% milk) for 1 h at room temperature. The membrane was developed using the RENAISSANCE Western blot Chemiluminescence Reagent (NEN, USA) according to the supplier's instructions. To determine the amount of chimeric IgG secreted from positive clones, 100 µl supernatants were applied in a two-fold dilution series via a vacuum manifold onto a nitrocellulose filter using a dot-blot apparatus alongside a two-fold dilution series of commercial humane IgG standard (Jackson ImmunoResearch Laboratories, USA), starting with a concentration of 1000 ng/ml. After blocking the membrane with 5% (v/v) non-fat milk in TBS for 1 h at room temperature, the membrane was washed briefly with TBS and incubated with HRP-conjugated goat anti human antibodies (×10,000 dilution in TBS/2% milk) for 1 h at room temperature. The membrane was developed as described above.

Evaluation of IgG Producing Clones for MUC1-Binding by ELISA

IgG producing clones were tested for MUC1-binding as follows: ELISA plates were coated with a 10-fold dilution of conditioned medium of mouse DA3 cells transfected with a secreted isoform of MUC1 diluted in 50 mM NaHCO$_3$ buffer (pH 9.6) at 4° C. for 20 h and blocked with 2% (v/v) non-fat milk in PBS for 2 h at 37° C. essentially as described (Mazor et al 2005, Mol Immunol 42, 55-69). All subsequent steps were done at room temperature. 100 µl supernatants of IgG1 producing clones were applied onto the plates and incubated for 1.5 h (diluted 1:2 in 2% (v/v) non-fat milk/PBS). Following incubation the plates were washed ×3 with PBST. Bound IgG was detected with HRP-conjugated goat anti human antibodies (×10,000 dilution in PBST). The ELISA was developed using the chromogenic HRP substrate TMB (Sigma, Israel) and color development was terminated with 1 M H$_2$SO$_4$. The plates were read at 450 nm.

Production and Purification of Chimeric H23 IgG1 from Culture Media of Stable Transfected HEK293 Cells Approximately 3×10$^6$-transfected HEK293 cells (chH23 clone B2 or chFRP5 clone G1) were cultured in 75 cm$^2$ flasks containing DMEM medium (Beit Haemek, Israel), supplemented with 10% fetal calf serum, 1.2 mg/ml G418 and 200 µg/ml hygromycin, at 37° C., 5% CO$_2$, in a humidified incubator. The culture was allowed to grow to 80% confluence followed by a gradual starvation of the cells to fetal calf sera (FCS), in a two-fold dilution series (reduction in serum concentration) for a period of 24 h of each dilution. The cells were totally deprived of FCS 72 h prior to harvesting. Chimeric IgGs were purified using protein A-SEPHAROSE (Amersham Biosciences, Sweden) chromatography. Briefly, 250 ml of culture supernatant was diluted 1:1 with loading buffer (20 mM Na$_2$HPO$_4$, 2 Mm NaH$_2$PO$_4$) and loaded onto a 5-ml protein A column at a flow rate of 2 ml/min. The column was extensively washed with loading buffer. Bound chimeric IgG was eluted with 0.1 M of citric acid (pH 3) and neutralized with 1 M Tris/HCl (pH 9). Protein-containing fractions were combined, dialyzed against 5 liter PBS (16 h, 4° C.), sterile filtered and stored at 4° C. Purified chimeric IgGs were analyzed by 12%/SDS polyacrylamide gel electrophoresis under reducing conditions and stained with GELCODE BLUE® dye. (Pierce, USA). For Western blot, purified IgGs were separated by 12%/SDS polyacrylamide gel electrophoresis under reducing conditions and electro-transferred onto nitrocellulose membrane. Chimeric IgGs were detected with HRP-conjugated goat anti human antibodies. The membrane was developed using the RENAISSANCE Western blot Chemiluminescence Reagent (NEN, USA) according to the supplier's instructions.

Construction of pET22b-ZZ-PE Expression Vector

Plasmid pET22b-ZZ-PE38 was designed to allow the expression of soluble ZZ-*Pseudomonas* exotoxin A (PE38) fusion protein secreted to the periplasm of BL-21 (DE3) *E. coli* cells.

Plasmid pB1(Fv)-PE38 (Benhar and Pastan 1995, Clin Cancer Res 1, 1023-1029) carries the scFv of anti Le$^Y$ monoclonal antibody B1 fused to a truncated fragment of *Pseudomonas* exotoxin A. As all members of that vector series (Brinkmann et al., 1991), the single-chain Fv fragment (scFv) is cloned between NdeI and HindIII sites. These sites were changed to NcoI and NotI sites, respectively, using site-directed mutagenesis essentially as described (Benhar et al 1994, J Biol Chem 269, 13398-404). The resulting plasmid was named pIB98-NN-B1(Fv)-PE38. The scFv-PE38 coding DNA fragment was recovered from pIB98-NN-B1(Fv)-PE38 by digestion with NcoI and EcoRI and ligated into a vector fragment isolated from pET22b (Novagen, USA) by digestion with the same enzymes. The resulting plasmid was named pET22b-NN-B1(Fv)-PE38.

Next, the scFv cloned in pET22b-NN-B1(Fv)-PE38 was replaced by an NcoI-NotI fragment of the ZZ domain that was isolated using pDS-ZZ plasmid DNA as template in a PCR reaction with primers ZZ-Nco-FOR (SEQ ID NO: 21) and ZZ-Not-BACK (SEQ ID NO: 22; Table 1). In the resulting plasmid, pET22b-ZZ-PE38, a T7 promoter controls the expression of a cassette comprising a pelB leader for secretion followed by the ZZ-domain-PE38 fusion.

Expression and Purification of ZZ-PE38 Fusion Protein

Periplasmic production of soluble ZZ-PE38 fusion protein was performed on a 1 liter scale. *E. coli* BL21 (DE3) cells transformed with pET22b-ZZ-PE38 expression vector were grown in 1 liter of SB medium supplemented with 100 µg/ml ampicillin, 0.5% (w/v) glucose and 0.4 gr/l MgSO$_4$ at 37° C. When the cells reached A$_{600}$ of 2.5 they were induced for protein overexpression with 1 mM IPTG at 30° C. for 3 h. Followed induction, the cells were collected by centrifugation (15 min, 4000 rpm at 4° C., Beckman GS3 rotor) and the periplasmic fractions were prepared by gently resuspending the cell pellet using glass beads in 200 ml of ice-cold 20% sucrose, 30 mM Tris-HCl (pH 7.4), 1 mM EDTA and left on ice for 15 min. Next, cells were collected by centrifugation as described above, the sup was discarded off and the culture was gently re-suspended in 200 ml of ice cold sterile water and left on ice for 15 min. Following incubation on ice, the periplasmic fraction was obtained by collecting the cells by centrifugation (15 min, 7000 rpm at 4° C., Beckman rotor GSA) and collecting the supernatant. The resulting supernatant (periplasmic fraction) was adjusted to 20 mM Tris-HCl (pH 7.4), 1 mM EDTA and the ZZ-PE38 fusion protein was purified from the periplasmic extract in two sequential chromatography steps of Q-SEPHAROSE and MONO-Q anion exchange columns (Pharmacia LKB) using fast protein liquid chromatography (FPLC), (Pharmacia, Sweden).

Preparation of chIgG-ZZ-PE38 Immunoconjugates

Conjugation of chimeric IgG1 antibodies with the ZZ-PE38 fusion protein was performed as follows, 0.5 ml of 4.5 mg/ml chH23 or chFRP5 in PBS were mixed with 0.5 ml of 4.5 mg/ml ZZ-PE38 fusion protein in PBS (3 fold molar excess of ZZ-PE38 over chimeric IgG) in an Eppendorf tube head-over-head for 16 h at 4° C. Separation of excess ZZ-PE38 from chIgG-ZZ-PE38 complex was performed by applying the sample to a SUPERDEX 75 size-exclusion column (Pharmacia LKB) using fast protein liquid chromatography (FPLC), (Pharmacia, Sweden). The proteins were separated in PBS at a flow rate of 1 ml/min. 1 ml fractions were collected.

Crosslinking of chFRP5-ZZ-PE38 immunoconjugate using the BS$^3$ reagent (Pierce, USA) was performed according to the supplier's recommendations. Briefly, 100 µl of 3 mg/ml chFRP5-ZZ-P38 in PBS were mixed with a 20-fold molar excess of BS$^3$ solution (dissolved in PBS). The preparation was incubate for 2 h at 4° C. Excess of non-reacting BS$^3$ reagent was removed by dialysis against 1 liter of PBS buffer using SLIDE-A-LYZER® Dialysis cassette with 3,500 MW cutoff at 4° C. for 16 hr with gentle stirring. Crosslinked-chFRP5-ZZ-PE38 in PBS buffer was sterile filtered and stored at 4° C.

Evaluation of Antigen Binding by ELISA

Analysis of binding to MUC1 by H23 was done as follows, ELISA plates were coated with a 10-fold dilution of MUC1 transfected DA3 cells conditioned medium diluted in 50 mM NaHCO$_3$ buffer (pH 9.6) at 4° C. for 20 h and blocked with 2% (v/v) non-fat milk in PBS for 2 h at 37° C., essentially as described (Mazor et al 2005, supra). All subsequent steps were done at room temperature. 2 µg/ml of purified chimeric H23 (chH23) and murine H23 Mab were applied onto the plates in a two-fold dilution series. Following incubation the plates were washed ×3 with PBST. HRP-conjugated goat anti human and HRP-conjugated goat anti-mouse antibodies were used as secondary antibodies (×10,000 dilution in PBST). The ELISA was developed using the chromogenic HRP substrate TMB (Sigma, Israel) and color development was terminated with 1 M $H_2SO_4$. The results were plotted as absorbance at 450 nm and the apparent binding-affinity was estimated as the IgG concentration that generates 50% of the maximal binding signal.

Evaluation of Binding-Affinity by Whole-Cell ELISA

Cellular MUC1 binding with chH23 IgG and murine H23 mAb was tested by whole-cell ELISA as follows; cell MUC1 positive cells were the human breast carcinoma T47D cell line. Following trypsinization, cells were washed once with 2% fetal calf serum, 0.05% $NaN_3$ in PBS (incubation buffer). In each experiment approximately $10^6$ cells were divided into individual immunotubes (Nunc, Sweden). To confirm the specificity, antibodies (1 µg/ml) were incubated with or without an excess of MUC1 protein from DA3-MUC1-transected cell line, for 1 h at room temperature prior to incubation with the cells and then were added to the cell tubes for 1.5 h at 4° C. After washing ×2 with incubation buffer, HRP-conjugated goat anti human and HRP-conjugated goat anti mouse (×2000) were added to the appropriate tubes for 1 h at 4° C. Detection of cell bound antibodies was performed by addition of 0.5 ml of the chromogenic HRP substrate TMB (Sigma, Israel) to each tube and color development was terminated with 0.25 ml of 1 M $H_2SO_4$. Finally, the tubes were centrifuged for 10 min at 4000 rpm and color intensity of supernatants was measured at 450 nm. The apparent binding-affinity was estimated as the IgG concentration that generates 50% of the maximal binding signal.

Cellular ErbB2-binding of chFRP5 IgG was evaluated by whole-cell ELISA performed as described above using the breast cancer cell line SKBR3 as ErbB2 positive.

Evaluation of cellular MUC1 binding activity of chH23-ZZ-PE38 or chFRP5-ZZ-PE38 immunotoxin by whole-cell ELISA was performed essentially as described above. Rabbit anti-PE sera (×200 dilution; Kindly provided by Dr. Ira Pastan, NCI, NIH) mixed with HRP-conjugated goat anti-rabbit (×1500 dilution) were used for the detection of bound chH23-ZZ-PE38 or chFRP5-ZZ-PE38 immunotoxins.

Flow Cytometry

Cellular MUC1 binding with chH23 IgG and murine H23 mAb was tested by flow cytometry. Cell lines used were the mouse cell line DA3, the MUC1-transfected cell line DA3-MUC1 (Baruch et al 1999, Cancer Res 59, 1552-61) the breast carcinoma lines T47D and MCF7 and the human kidney cell line HEK293. Approximately $5 \times 10^5$ cells were used in each experiment. After trypsinization, cells were washed once in 2% fetal calf serum, 0.05% $NaN_3$ in PBS (FACS buffer). To confirm the specificity, antibodies (10 µg/ml) were incubated with or without an excess of MUC1 protein from DA3-MUC1-transected cell line, for 1 h at room temperature prior to incubation with the cells and then were added to the cell tubes for 1 h at 4° C. After washing ×2 with FACS buffer, FITC-labeled goat anti human and FITC-labeled goat anti mouse (×50 dilution) was added to the appropriate tubes for 45 min at 4° C. Detection of bound antibodies was performed by means of flow cytometry on a FACS-CALIBUR (Becton Dickinson, CA) and results were analyzed with the CELLQUEST program (Becton Dickinson).

Evaluation of cellular MUC1 binding activity of chH23-ZZ-PE38 immunotoxin was tested by flow cytometry essentially as described above. To confirm specificity, chH23-ZZ-PE38 immunoconjugate was incubated in the presence or absence of 10-fold excess of un-conjugated chH23 IgG1 prior to incubation with the cells. Rabbit anti-PE sera (×50 dilution) mixed with FITC-labeled goat anti-rabbit (×50 dilution) were used for the detection of bound chH23-ZZ-PE38 immunotoxin.

Evaluation of cellular ErbB2-binding by chFRP5 IgG was performed as described above. Cells expression various levels of ErbB2 on their surface were tested.

Immunohistochemistry

A large set of paraffin-embedded normal and tumor tissue sections were used to compare immunohistochemical staining obtained by the purified chH23 IgG and the murine H23 mAb. Five-micrometer sections of paraffin-embedded tissues were deparafinized with xylene and ethanol and rehydrated with hyaluronidase (Fiorentini et al 1997, Immunotechnology 3, 45-59). Endogenous peroxidase was blocked with 0.3% $H_2O_2$ in methanol and slides were preincubated with 10% goat serum in PBS for 30 min. Antibodies were diluted to a concentration of 20 µg/ml in PBS containing 10% goat serum and incubated with slides overnight at 4° C. After rinsing with PBS, HRP-conjugated goat anti human and HRP-conjugated goat anti mouse (1/50 dilution) was added to the appropriate slides for 30 min at room temperature. After each incubation step, slides were washed for 10 min with PBS. Staining was developed using the HRP chromogenic substrate 3,3'-diaminobenzidine (Sigma, Israel), followed by counterstaining with hematoxylin.

A large set of adjacent Paraffin-embedded tumor tissue sections were used to compare immunohistochemical staining obtained by the purified chFRP5 IgG and of the two positive anti-ErbB2 Mab; Herceptin® and a commercial mouse anti-ErbB2 Mab. The sections were processed and developed as described above.

Analysis of IgG Internalization Using Confocal Microscopy

Internalization of chH23 IgG1 and of chFRP5 IgG was evaluated using confocal microscopy. The human breast carcinoma T47D cell line was used to evaluate the internalization capabilities of chH23 at 4° C. and 37° C. The human breast carcinoma SKBR3 cell line was used to evaluate the internalization capabilities of chFRP5 at 4° C. and 37° C. Sterile 24 mm cover slips were placed in a 6 well plate and incubated for 1 hr at room temperature with 800 µl of 10 µg/ml poly-L-lysine followed by two washes with 1 ml PBS each. Approximately $4 \times 10^5$ cells were seeded on the cover slips in each well and grown to 40%-50% confluence in DMEM supplemented with 10% FCS (complete medium). Cells tested for chH23 internalization at 4° C. were preincubated with complete medium supplemented with 0.5% $NaN_3$ for 2 h in 4° C. prior to the addition of the antibody (5 µg/ml) and incubation of 1 h in 4° C. Cells tested for chH23 internalization at 37° C. were incubated with 5 µg/ml of the antibody in complete medium for 1 h at 37° C. in a humidified atmosphere of 95% air and 5% $CO_2$. Subsequent the incubation with the antibody, the cells were gently washed twice with PBS to remove excess mAb and incubated for 2 h under the same conditions of the previous step. Next, the cells were gently washed twice with PBS and fixed in two sequential steps of incubation for 10 min with ice cold methanol followed by 10 min incubation with ice cold acetone. Following the fixation step, the cells were gently washed with PBS and blocked with 10% normal goat serum (NGS) in PBS for 25 min at RT. The blocking solution was aspirated and FITC-labeled goat anti human (×150 dilution) was added cells were incubated with ×150 dilution of FITC conjugation anti human antibodies for 2 hr at RT. Finally, the cells were gently washed ×3 with PBS and staining pattern (membranous or intracellular) images were acquired using a LSM 510 laser scanning confocal microscope (Vontz 3403B).

Cell-Viability Assay

The cell-killing activity of immunotoxins was measured by MTT assay. Target and control cells were seeded in 96-well plates at a density of $10^4$ cells/well in DMEM supplemented with 10% FCS. Various concentration of chH23-ZZ-PE38 and relevant control proteins were added in triplicate and the cells were incubated for 48 hr at 37° C. in 5% $CO_2$ atmosphere. After treatment, the media was replaced by immunotoxin-free media (125 µl per well) containing 5 mg/ml MTT reagent (Thiazolyl Blue Tetrazoliam Bromide, Sigma, Israel, dissolved in PBS) and the cells were incubated for another 4 h. MTT-formazan crystals were dissolved by the addition of 20% SDS, 50% DMF, pH 4.7 (100 µl per well) and incubation for 16 h at 37° C. in 5% $CO_2$ atmosphere. Absorbance at 570 nm was recorded on an automatized microtiter plate reader. It was established that optical density was directly proportional to the cell number up to the density reached by the end of the assay. Identical concentrations and combinations were tested in three separate wells per assay and the assay was performed at least three times. The results were expressed as percentage of living cells in comparison to the untreated controls that were processed simultaneously using the following equation: ($A_{570}$ of treated sample/$A_{570}$ of untreated sample)×100. The $IC_{50}$ values were defined as the immunotoxin concentrations inhibiting cell growth by 50%.

Functional Stability Analysis

The functional stability of chFRP5-ZZ-PE38 immunoconjugate and the crosslinked-chFRP5-ZZ-PE38 derivative was determined by incubation of the purified proteins at 37° C. for varying periods under three conditions; diluted in PBS, diluted in PBS containing a 10-fold molar excess of commercial protein-A purified human IgG antibodies, and diluted in 100% human serum. These incubations were followed by analysis of cellular ErbB2 binding of SKBR3 cells by whole-cell ELISA and in cell-killing of A431 cells using MTT assay. At each time-point, an aliquot was removed and spun for 10 min at 20,000 g to remove precipitated protein before being analyzed for cellular ErbB2 binding and cell-killing of A431 cells.

Pharmacokinetics of chFRP5-ZZ-PE38 and scFv(FRP5)-ETA in Mice Serum

The recombinant immunotoxin scFv(FRP5)-ETA was kindly provided by Prof. Winfried Wels, Georg Speyer Haus, Frankfurt am Main, Germany. This is a recombinant immunotoxin comprising the scFv derivative of FRP5 linked to a truncated *Pseudomonas* exotoxin (Wels et al 1992, Cancer Res 52, 6310-7). The relevant toxin fragment is known in the US as PE40 (from which PE38 was derived by deletion of a short segment of domain Ib) Brinkman et al 1991, Proc Natl Acad Sci USA 88, 8616-20) and in Europe it is referred to as ETA. To evaluate and compare the blood pharmacokinetics of chFRP5-ZZ-PE38 and scFv(FRP5)-ETA, female BALB/c mice (6-8 weeks old, ~20 g) were given a single i.v. dose of 15 µg chFRP5-ZZ-PE38 or 5 µg scFv(FRP5)-ETA diluted in 200 µl PBS by injection into the tail vein. Blood samples were collected from the orbital vein of mice injected with scFv (FRP5)-ETA at 2, 5, 10, 20, 30, 60, 120 and 240 min after injection and at 2, 5, 10, 20, 30, 60, 120, 240, 480 and 1440 min for mice injected with chFRP5-ZZ-PE38. Each mouse was bled two or three times, so different mice were used to collect data for the various time points. Each time point represents the mean of results obtained from two mice. After clotting the blood samples on ice the serum concentration of chFRP5-ZZ-PE38 and scFv(FRP5)-ETA was determined by dot-blot analysis and the concentration of remaining active immunotoxin was determined by incubating dilutions of the serum with A431 cells and measuring cell-viability by MTT assay. Determination of immunotoxins serum concentration by dot-blot analysis was performed as follows, 100 µl of serum diluted 1:100 in PBS of each mouse at a time group was applied in a two-fold dilution series via a vacuum manifold onto a nitrocellulose filter using a dot-blot apparatus (Schleicher & Schuell. USA), alongside a two-fold dilution series of 100 ng/ml of chFRP5-ZZ-PE38 or scFv(FRP5)-ETA that were used to determine the immunotoxin concentration in each serum sample. Rabbit anti-PE sera (×2500 dilution) mixed with HRP-conjugated goat anti-rabbit antibodies (×5000 dilution) were used for the detection of the immunotoxins. The membrane was developed using the RENAISSANCE Western blot Chemiluminescence Reagent (NEN, USA) according to the supplier's instructions. Determination of remaining active immunotoxin concentration in serum sample by MTT assay was performed as follows, 100 µl of serum diluted 1:100 in DMEM medium supplemented with 10% FCS of each mouse at a time group were added in a 10-fold dilution series to A431 cells seeded in 96-well plates at a density of $10^4$ cells/well. A standard curve, obtained by incubating A431 cells alongside a serial dilutions of chFRP5-ZZ-PE38 or scFv(FRP5)-ETA was used to determine the immunotoxin concentration in each serum sample. The MTT cell-viability assay was performed essentially as described above.

Toxicity Assays of ZZ-PE38 and ZZ-PE38 Immunoconjugates in Mice

The single-dose mouse $LD_{50}$ of ZZ-PE38 fusion protein and three immunoconjugates; chFRP5-ZZ-PE38, crosslinked-chFRP5-ZZ-PE38 and hIgG-ZZ-PE38 was tested using female BALB/c mice (6-8 weeks old, ~20 g), that were given a single i.v. injection with different doses of each protein diluted in 200 µl PBS. Mice were monitored for weight loss or death for 2 weeks after injection.

Antitumor Activity of chFRP5-ZZ-PE38 and scFv(FRP5)-ETA

To establish xenografts, female BALB/c athymic nude mice (6-8 weeks old, ~20 g) 3-5 mice per group were injected i.v. with $1.5 \times 10^6$ A431 cells suspended in 0.2 ml PBS. By day 9 post injection, tumors of about 30-40 $mm^3$ had formed. Mice were treated on days 9, 12, 15, 18 and 21 by i.v. injections of different doses of the two immunotoxins diluted in PBS. Tumors were measured with a caliper at 3-day intervals, and the tumor volumes were calculated according to the formula: volume=(length)×(width)×(0.4). Animals were sacrificed when tumors reached 2 cm in diameter or when animals appeared to be in distress.

Example 1

Construction of Mammalian Expression Vectors for Human IgG1 Derivatives

Figure 1:
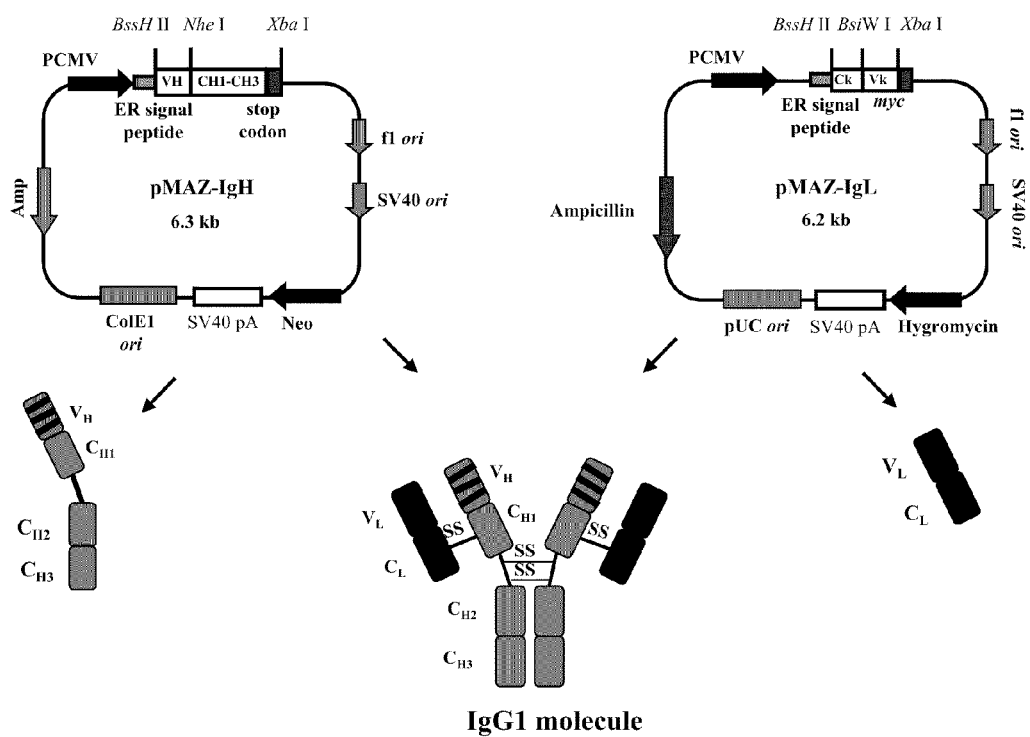
FIG. 1: Schematic representation of mammalian pMAZ-IgH and pMAZ-IgL expression vectors.
Represented are maps of plasmids pMAZ-IgH for human γ1 heavy chain expression and pMAZ-IgL for human κ light chain expression carrying desired V genes for the production of human IgG1 antibodies in mammalian cell culture.

Mammalian vector pMAZ-IgH for human γ1 heavy chain expression and pMAZ-IgL for human κ light chain expression were designed for production of human IgG1 antibodies in mammalian cell culture (FIG. 1). Each vector carries the germline sequence of the respective heavy or light chain gene including its polyadenylation site located downstream of the translation termination codon. VH domains are introduced into the IgH expression vector via the BssHII and NheI restriction sites, whereas, VL domains are cloned into the IgL expression vector as BssHII and BsiWI fragments. The IgH plasmid carries a neomycine expression cassette for geneticin (G418) selection, while the IgL plasmid carries a hygromycin B resistance cassette for the isolation of stable transfectants.

The strong human cytomegalovirus early promoter drives both the heavy and light chain genes. In addition, both vectors contain an ampicillin selectable marker and SV40, ColE1 and f1 origin of replication.

Figure 2:
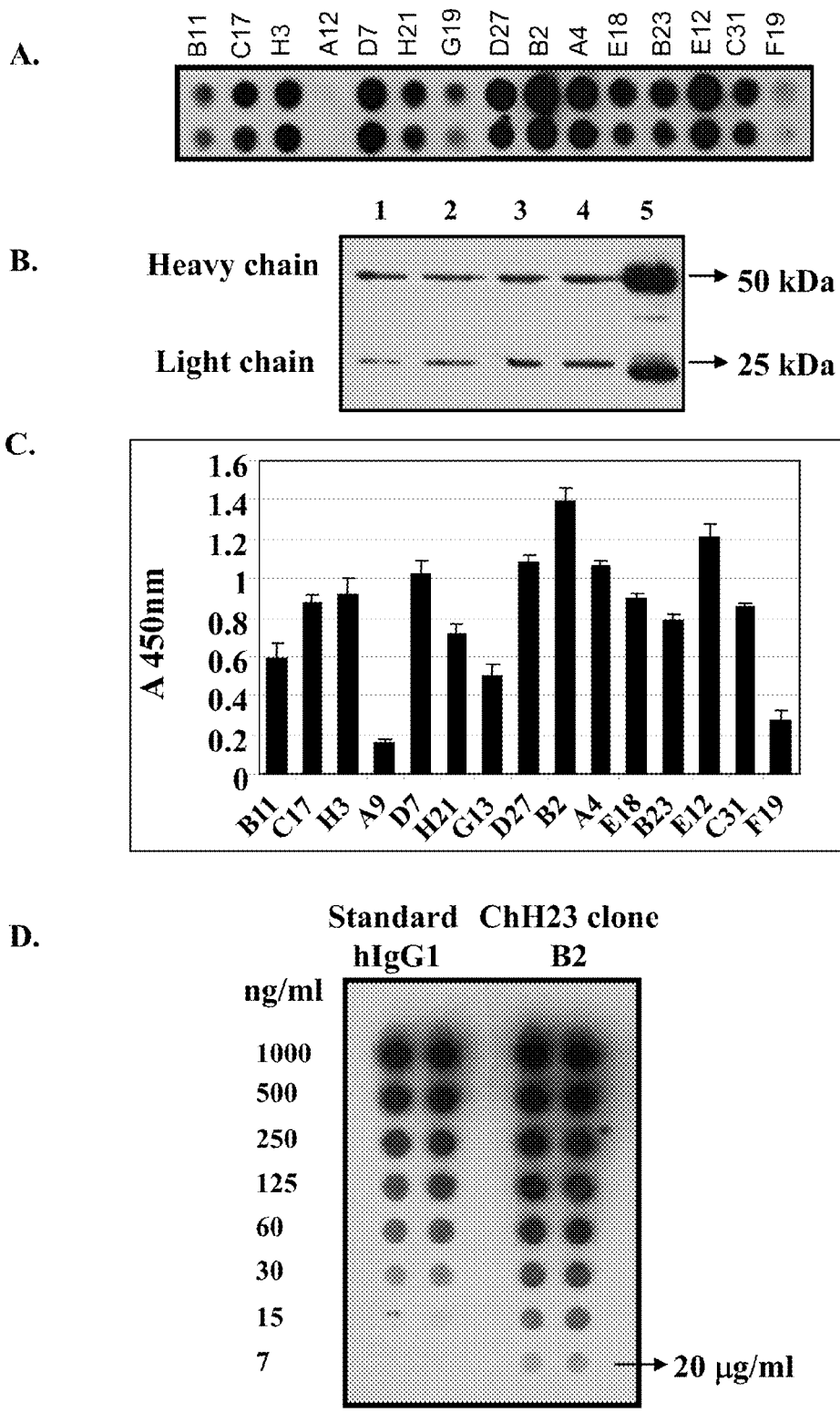
FIGS. 2A, B, C and D: Analysis of stable clones expressing chimeric H23 IgG and evaluation of antigen binding.
A. Dot-blot analysis of stable clones expressing chimeric IgG. Supernatants (100 μl) of individual clones were applied in duplicate onto a nitrocellulose filter. ChH23 IgG antibodies were detected using HRP-conjugated goat anti-human IgG as secondary antibody. The membrane was developed using ECL reagents and exposure to X-ray film.
B. Immunoblot of spent culture medium of positive clones for determination of heavy and light chain production. Lanes 1-4, candidate clones; lane 5, commercial human IgG (0.5 μg/ml).
C. Analysis of MUC1 binding by individual clones by ELISA. Microtiter plates were coated with MUC1-containing spent culture medium (100 μl/well). HRP-conjugated goat anti-human IgG was used as secondary antibody. The ELISA was developed using the chromogenic HRP substrate TMB. The error bars represent standard deviations of three independent experiments.
D. Determination of chH23 secretion levels. Supernatants (100 μl) of stable clone B2 were applied in a two-fold dilution series onto a nitrocellulose filter alongside a two-fold dilution series of commercial human IgG standard at the indicated concentrations. HRP-conjugated goat anti-human IgG was used as secondary antibody.

The variable region genes encoding the murine anti-MUC1 H23 mAb were cloned for expression as chimeric γ1/kappa antibody into the mammalian pMAZ-IgH and pMAZ-IgL expression vectors (SEQ ID NOS: 7 and 8, respectively) as described in Materials and Methods. After co-transfection of HEK293 cells with the two heavy and light chain gene-containing plasmids, cells were grown on selective media as indicated in material and methods. Approximately 40% of the wells showed cell growth after 10 days in culture. Supernatants of clones growing on medium containing selection markers were tested for IgG secretion by Dot-Blot (FIG. 2A), and determination of heavy and light chain production using Western-Blot (FIG. 2B). Approximately 90% of the wells with selected cells were positive for IgG production, with secretion levels of chimeric IgG between 0.1-20 μg/ml. IgG producing clones were analyzed in ELISA for antibody binding to MUC1 (FIG. 2C), showing a significant correlation between antibody secretion level and the intensity of MUC1 binding. Positive clone B2 that secreted at 20 μg/ml (FIG. 2D) was selected for further evaluation of chimeric H23 IgG.

A similar procedure was carried out to obtain chFRP5 IgG, where the clone chosen was G1.

Example 2

Expression and Purification of Chimeric IgG1 Derivatives

Figure 3:
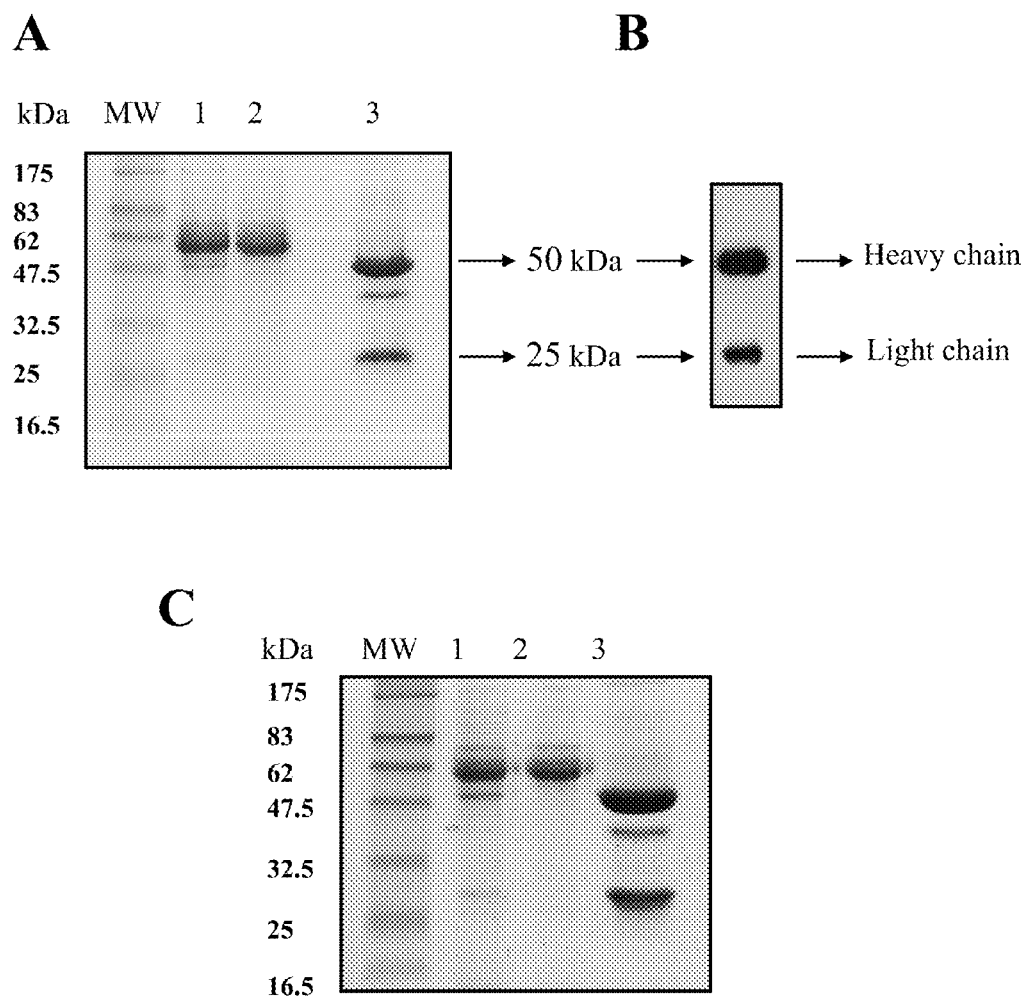
FIGS. 3A, B and C: Purification of chH23 and chFRP5 IgG1 from culture media of HEK293 cells.
A. Purification of soluble chH23 IgG1 using protein A column chromatography. Lane 1, total culture media cell extract; lane 2, protein A column flow-through; lane 3, purified chH23 IgG1 clone B2 antibody. Proteins were separated on a 12%/SDS polyacrylamide gel under reducing conditions and visualized by staining with GEL-CODE BLUE (stain reagent). Arrows mark the size and position of human IgG1 heavy and light chains.
B. Western-Blot analysis of purified chH23 IgG1 clone B2 antibody using HRP-conjugated goat anti-human IgG.
C. Purification of soluble chFRP5 IgG1 using protein A column chromatography. Lane 1, total culture media cell extract; lane 2, protein A column flow-through; lane 3, purified chFRP5 IgG1 clone G1 antibody. Proteins were separated on a 12%/SDS polyacrylamide gel under reducing conditions and visualized by staining with GEL-CODE BLUE (stain reagent).

Chimeric H23 and FRP5 IgG antibodies were purified from stable 293 cell lines B2 and G1, respectively, grown in FCS stepwise starvation media as described in Materials and Methods. Stepwise starvation of the cells to FCS not only minimized the contamination with bovine IgG upon purification on protein A column, but also increased the amount of antibody secreted to the medium by the FCS deprived cells. Under these conditions, more than 95% pure chimeric IgG1 protein was obtained based upon separation on 12%/SDS-PAGE under reducing conditions and verification of human Ig heavy and light chain production by Western-Blot (FIG. 3). Anti-MUC1 chH23 and anti ErbB2 chFRP5 IgG1 antibodies were purified at a total yield of 20 mg per liter of culture.

Example 3

Analysis of chH23 IgG1 Apparent Binding Affinity to MUC1

Figure 4:
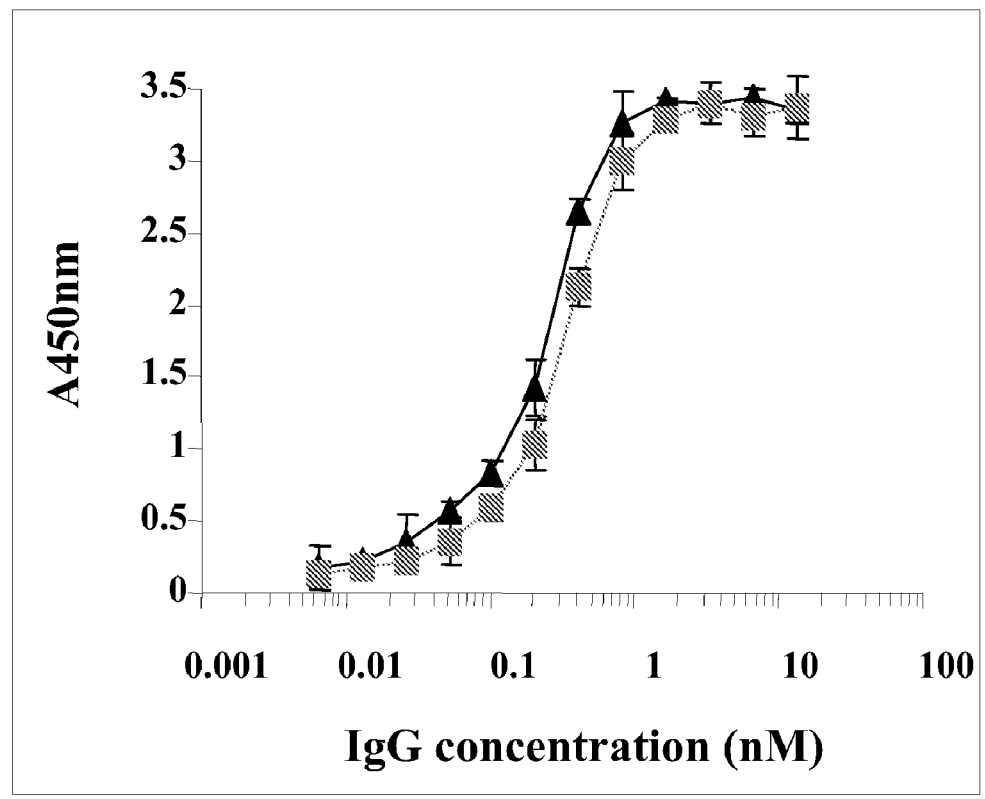
FIG. 4: Evaluation of MUC1 binding-affinity by H23 Mab and chH23 IgG1 in ELISA.
Comparative analysis of MUC1 binding-affinity by chH23 IgG1 (filled squares) and murine H23 mAb (filled triangles) by half-maximal binding assay using standard ELISA. Microtiter plates were coated with MUC1-containing spent culture medium in 50 mM NaHCO$_3$ (pH 9.6) buffer in a volume of 100 μl. MUC1 binding assays were performed with 2 μg/ml of purified antibodies in two-fold dilution series. HRP-labeled goat anti-human and HRP-labeled goat anti-mouse were used as secondary antibodies. The ELISA was developed using the chromogenic HRP substrate TMB. The error bars represent standard deviations of three independent experiments. The binding-affinity was estimated as the IgG concentration that generates 50% of the maximal signal.

To compare the binding affinities of chH23 IgG1 with that of H23 mAb, we performed a comparative half-maximal binding assay using ELISA. The results indicated that purified chH23 IgG1 binds MUC1 similarly to the parental mAb. Determination of the apparent binding affinities $K_D$ of the two antibodies from the half-maximal binding signal revealed that both antibodies bind MUC1 with similar apparent affinities, 0.2 nM for the murine mAb and 0.3 nM for chH23 (FIG. 4). These results suggest that indeed conversion of the antibody from a monovalent format (Mazor et al., 2005 supra) to a bivalent format as the chimeric H23 is, increased the antibody's apparent binding affinity more then a hundred-fold, to a level roughly equal to that of the parental H23 mAb. This is not surprising, considering the repetitive nature of the MUC1 antigen that allows for avidity of the bivalent IgG that are directed to the VNTR region to be manifested (Hendrikx et al 2002, Am J Pathol 160, 1597-608).

Figure 5:
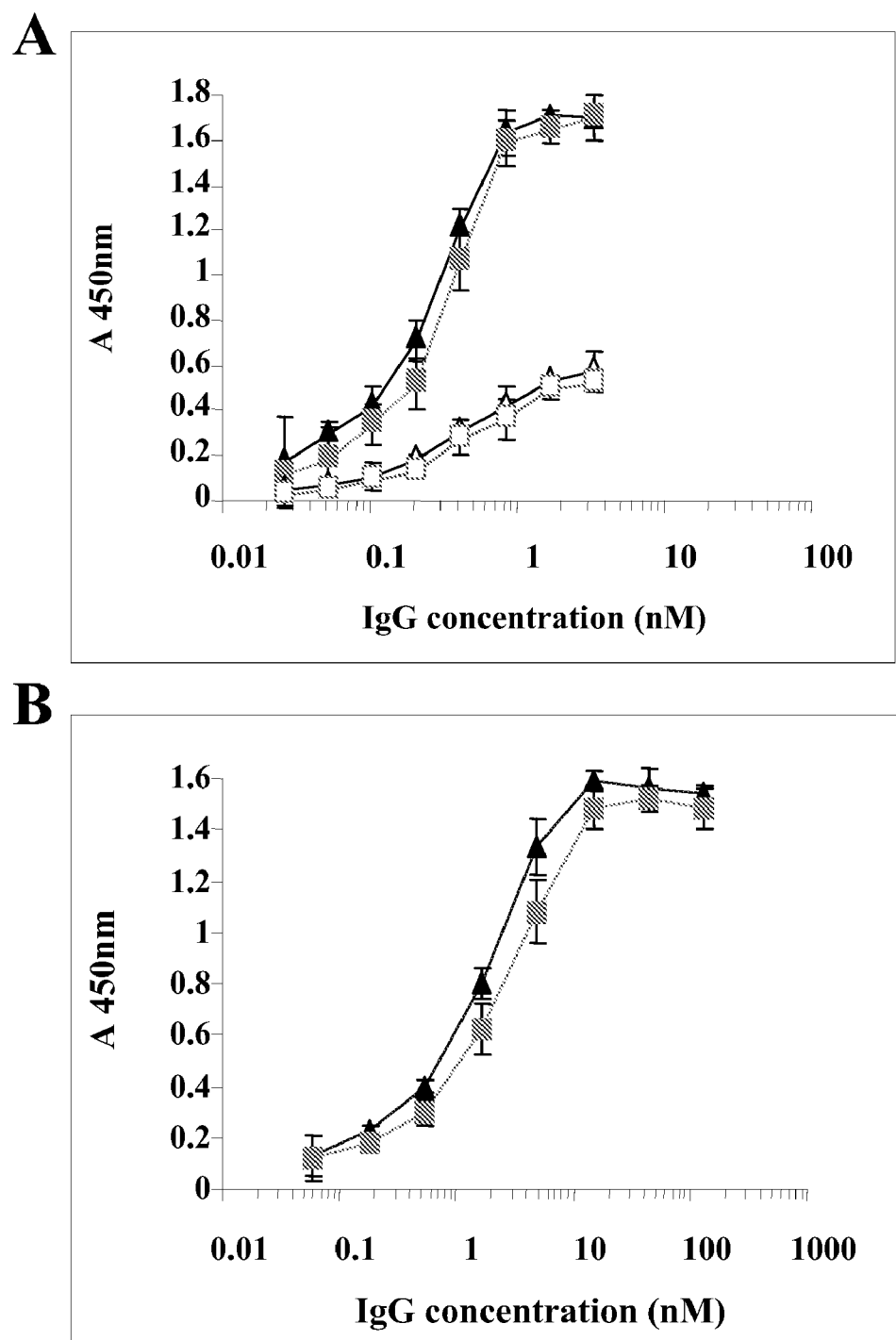
FIGS. 5A and B: Evaluation of MUC1 and ErbB2 binding-affinities by whole-cell ELISA.
A. Comparative cellular MUC1 binding-affinity by chH23 IgG1 (square symbols) and murine H23 mAb (triangle symbols) was assessed by whole-cell ELISA. The human breast carcinoma T47D cell line was used as MUC1 expressing cells. To confirm specificity, antibodies (1 μg/ml) were incubated in the presence (empty symbols) or absence (filled symbols) of MUC1 protein prior to incubation with the cells.

To further compare the binding affinities between chH23 and murine H23 mAb we tested cellular MUC1 binding by whole-cell ELISA. Cells used in this assay were the human breast carcinoma T47D cell line. As with the standard ELISA results, the results of this assay showed that both antibodies bind the MUC1 positive tumor cells with similar affinity, 0.25 nM for the murine mAb and 0.3 nM for chH23 (FIG. 5A). Furthermore, this study demonstrate the specificity of the two antibodies to cellular MUC1, as binding of the MUC1-specific antibodies to the cells could be competed off with an excess of soluble MUC1 protein.

When evaluated for specific cellular-ErbB2 binding, chFRP5 IgG1 exhibited similar binding characteristics as the commercial FDA-approved anti-ErbB2 Mab HERCEPTIN (Trastuzumab) (FIG. 5B). Estimation of the apparent binding affinities of the two anti-ErbB2 antibodies from the half-maximal binding signal of this whole-cell ELISA on SKBR3 cells revealed that both antibodies bind ErbB2 receptor with similar apparent affinities, 1.7 nM for chFRP5 IgG1 and 2.4 nM for HERCEPTIN (trastuzumab).

Example 4

Comparative Flow Cytometry Analysis

We further evaluated the binding capabilities of the chimeric and murine H23 antibodies by testing cellular MUC1 binding using flow cytometry. Cell lines used in this assay were the human breast carcinoma lines T47D and MCF-7, the mouse cell line DA3, the MUC1-transfected cell line DA3-MUC1 (Baruch et al., 1999), and the control human kidney cell line HEK293. FIG. 6A) indicates that chH23 stains the breast cancer cell lines and the MUC1 transfected cells with substantially the same pattern as the murine H23 mAb. T47D cells express higher levels of MUC1 compared to MCF-7 cells and with a heterogeneous population of MUC1 displaying cells in comparison to the homogeneous MUC1-DA3 cells, whereas no binding was seen with the control DA3 and HEK293 cell lines. Furthermore, we demonstrated the specificity of the two antibodies to cellular MUC1 was demonstrated, as binding of the both antibodies to MUC1 positive cells was competed off following incubation of the antibodies with an excess of MUC1 conditioned medium prior to incubation with the cells.

Comprehensive flow cytometry analysis on a large set of tumor cells expressing varying levels of ErbB2 antigen revealed that chFRP5 recognized cellular ErbB2 and stains the tumor cell lines with substantially the same pattern as does the anti-ErbB2 HERCEPTIN (trastuzumab) Mab (FIG. 6B). The differences in staining intensities between the various tumor cells usually corresponded to the ErbB2 expression level among the individual tumor cell lines.

Example 5

Expression and Purification of ZZ-PE38 Fusion Protein

Periplasmic production of soluble ZZ-PE38 fusion was performed as described in Materials and Methods. Periplasmic fractions were prepared and ZZ-PE38 fusion protein was purified by two sequential chromatography steps of Q-SEPHAROSE and MONO-Q anion exchange columns using fast protein liquid chromatography (FPLC) until >90% purification was achieved as seen in FIG. 8A.

Example 6

Preparation of chH23-ZZ-PE38 Immunoconjugate

Conjugation of purified chH23 IgG1 antibody with ZZ-PE38 fusion protein was performed as described in Materials and Methods. Separation of excess ZZ-PE38 and unconjugated mAb from the chH23-ZZ-PE38 complex was performed by applying the sample to a SUPERDEX 75 size-exclusion column using fast protein liquid chromatography (FPLC). Purified chH23-ZZ-PE38 immunoconjugate was indicated by 12%/SDS-PAGE under reducing conditions (FIG. 8B).

Example 7

Binding Properties of the chH23-ZZ-PE38 Immunoconjugate

Whole-Cell ELISA

To evaluate the binding capabilities of chH23-ZZ-PE38 immunotoxin we performed cellular MUC1 binding assay by whole-cell ELISA using the human breast carcinoma T47D cell line. Rabbit anti-PE sera mixed with HRP-conjugated goat anti-rabbit were used for the detection of bound chH23-ZZ-PE38 immunotoxin. The results of this assay showed that the affinity tagging of the ZZ-PE38 fusion protein to chH23 Fc domain was stable, furthermore, the conjugation process did not undermine chH23 antigen recognition as the immunoconjugate retained its binding capabilities to MUC1 positive tumor cells with comparable affinity to the un-conjugated chH23 IgG1 (FIG. 9A).

Flow Cytometry Analysis

The binding capabilities of the chH23-ZZ-PE38 immunoconjugate by testing cellular MUC1 binding was further evaluated using flow cytometry. FIG. 9B indicates that chH23-ZZ-PE38 stains the MUC1 positive human breast carcinoma T47D cells while the control human IgG-ZZ-PE38 immunoconjugate prepared and purified in the same way showed no binding to the tumor cells. Furthermore, the specificity of chH23-ZZ-PE38 immunoconjugate to cellular MUC1 was demonstrated, as binding of the anti-MUC1 immunotoxin to the tumor cells was competed off with the addition of 10-fold excess of un-conjugated chH23 IgG1.

Example 8

Cytotoxic Activity of chH23-ZZ-PE38

To evaluate the cytotoxic activity of chH23-ZZ-PE38 immunotoxin, in vitro cell-killing experiments were performed. T47D and MCF7 human breast carcinoma cell lines were incubated for 48 hr with varying concentrations of chH23-ZZ-PE38 and of the control proteins. The relative number of viable cells in comparison with cells grown in the absence of toxin was determined using an enzymatic MTT assay. The results of the MTT assay (FIG. 10) show that both the highly MUC1-expressing T47D cells (panel A) and the moderate MUC1-expressing MCF7 cells (panel B) showed almost no sensitivity to chH23-ZZ-PE38 immunconjugate-mediated killing, with an $IC_{50}$ of ~5 µg/ml for T47D cells and undetectable sensitivity for MCF7 cells to the concentrations of chH23-ZZ-PE38 used in this assay. Comparable results were obtained with the negative control hIgG-ZZ-PE38 onjugate. These results indicate that chH23-ZZ-PE38 was not cytotoxic to the tested MUC1-expressing tumor cells; since sensitivity of reported immunotoxin-targeted cells represented $IC_{50}$ values at the range of 0.1-10 ng/ml (Pai et al 1991, Proc Natl Acad Sci USA 88, 3358-62). These results suggest that chH23 may not be suitable for delivering a therapeutic cargo into particular target cells i.e. those into which chH23 does not internalize.

Example 9

Preparation of chFRP5-ZZ-PE38 Immunoconjugate

The ZZ-PE38 fusion protein was prepared as described in Materials and Methods. Conjugation of purified chFRP5 IgG1 antibody with the ZZ-PE38 fusion protein was performed as described for chH23 above. Separation of excess ZZ-PE38 and unlabeled mAb from chFRP5-ZZ-PE38 complex was performed by applying the sample on a SUPERDEX 75 size-exclusion column using FPLC. The chFRP5-ZZ-PE38 immunoconjugate was obtained as a highly pure immunoconjugate as evident from the SDS-PAGE analysis (FIG. 8C).

Example 10

Binding Analysis of chFRP5-ZZ-PE38 Immunoconjugate

To evaluate the binding capabilities of chFRP5-ZZ-PE38 immunotoxin, cellular ErbB2 binding assay by whole-cell ELISA was performed. The binding reactivity of the bivalent chFRP5-ZZ-PE38 immunoconjugate was compared with that of a recombinant scFv(FRP5)-ETA monovalent derivative (Wels et al., 1995 supra). FIG. 11 shows that chFRP5-ZZ-PE38 retained its binding activity to cellular ErbB2-expressing SKBR3 tumor cells with similar apparent affinity as the un-conjugated form of chFRP5 IgG1. This indicated that the affinity tagging of the ZZ-PE38 fusion protein to chFRP5 Fc domain did not undermine chFRP5 antigen recognition. However, comparison of the apparent binding affinities of chFRP5-ZZ-PE38 with that of the recombinant scFv(FRP5)-ETA by determining the concentration of immunotoxin that produces half maximal specific binding signal revealed that the bivalent immunotoxin had an apparent affinity of 1.7 nM, whereas the monovalent immunotoxin exhibited a 20-fold lower apparent affinity of 30 nM. This result is in agreement with the affinities values reported for scFv(FRP5)-ETA and the parental FRP5 Mab (Wels et al., 1992 supra). The binding activities of both forms of FRP5 immunotoxins were further compared by flow cytometry analysis using equal molar concentration of the two immunotoxins against a large set of tumor cells expressing varying levels of ErbB2 antigen. The results (FIG. 12) show that with all tumors cell lines tested, the bivalent chFRP5-ZZ-PE38 (A) produced more intense staining then the counterpart recombinant scFv(FRP5)-ETA monovalent derivative (B) as shown by the overlapping staining intensities results obtained by both immunotoxins (C). These results correlate with the binding affinities obtained for the two immunotoxins by whole-cell ELISA and emphasize the potential superiority of a bivalent antibody over its monovalent scFv derivative. Furthermore, the specificity of chFRP5-ZZ-PE38 immunoconjugate binding to cellular ErbB2 was demonstrated, as binding of the bivalent immunotoxin to the SKBR3 tumor cells could be competed off with the addition of 10-fold excess of un-conjugated chFRP5 IgG1 (FIG. 13A). The control human IgG-ZZ-PE38 immunoconjugate prepared and purified in the same way showed no binding to the SKBR3 tumor cells (FIG. 13B).

Example 11

Cell-Killing Activities of chFRP5-ZZ-PE38

To evaluate the cytotoxic activity of chFRP5-ZZ-PE38 immunoconjugate, we performed cell-killing experiments on a large set of human tumor cell lines expressing varying levels of ErbB2 receptors as shown in Table 2. Cells were incubated for 48 hr with various concentrations of chFRP5-ZZ-PE38 and the corresponding control proteins and the relative number of viable cells was determined using an enzymatic MTT assay. The results are shown in FIG. 14 and the $IC_{50}$ values are summarized in Table 2. The results indicated that chFRP5-ZZ-P38 was cytotoxic for all five cell lines tested with $IC_{50}$ values that in most cases correlate with the levels of ErbB2 expression among the different cells. SKBR3 and A431 tumor cells were most sensitive to the immunoconjugate with $IC_{50}$ values of 3.5 ng/ml and 1.8 ng/ml respectively. T47D and MCF7 cells were moderately sensitive to chFRP5-ZZ-PE38 while MDA-MB231 cells showed very low sensitivity which in some cases reflects a lower level of ErbB2 expression of approximately $10^3$ or less receptors per cell. Taken together, the cell killing activities achieved with chFRP5-ZZ-PE38 are a consequence of specific targeting and internalization of the immunoconjugate into the tumor cells, since none of the separable components alone nor the negative control hIgG-ZZ-PE38 were significantly toxic towards any of the tumor cells. The cytotoxic activities of the chFRP5-ZZ-PE38 immunoconjugate toward A431 cells correlated to the $IC_{50}$ values reported for the anti-mucin B1 mAb conjugated chemically to a truncated LysPE40 derivative of *Pseudomonas* exotoxin A (Pai et al 1991, Proc Natl Acad Sci USA 88, 3358-62) and exceeded the results reported for the anti-mesothelin K1 mAb conjugated chemically to a truncated LysPE38QQR derivative of *Pseudomonas* exotoxin A (Hassan et al 2000, J Immunother 23, 473-9).

TABLE 2

In vitro cell-killing activity

| Cell line | Number of ErbB2 receptors | ChFRP5-ZZ-PE38 | $IC_{50}$ (ng/ml) hIgG-ZZ-PE38 | ZZ-PE38 | ChFRP5 |
|---|---|---|---|---|---|
| SKBR3 | $1.5 \times 10^6$ | 3.5 | >10000 | >10000 | >10000 |
| A431 | $2 \times 10^4$ | 1.8 | 3500 | >10000 | >10000 |
| T47D | ~$10^4$ | 1000 | >10000 | >10000 | >10000 |
| MCF7 | <1000 | 600 | >10000 | >10000 | >10000 |
| MDA-MB231 | <1000 | >10000 | >10000 | >10000 | >10000 |

Comparison of the cytotoxic activities of the bivalent chFRP5-ZZ-PE38 with that of the monovalent scFv(FRP5)-ETA using equal molar concentration of each immunotoxin showed that the former was much more potent than the latter, with $IC_{50}$ values of 30 pM vs 1000 pM respectively (in SKBR3 cells), and 10 pM vs 52 pM respectively (in A431 cells; see FIG. 15 and Table 3). Moreover, while the low ErbB2-expressing MCF7 and MDA-MB231 cells showed moderate sensitivity to chFRP5-ZZ-PE38, these cells were totally unaffected by equimolar concentrations of the monovalent scFv(FRP5)-ETA. The specificity of the two immunotoxins in targeting and killing ErbB2-expressing tumor cells was demonstrated, since the cytotoxic activity of both immunotoxins was competed off in the presence of excess chFRP5 IgG1. Our experimental $IC_{50}$ values achieved for the monovalent scFv(FRP5)-ETA are in full agreement with the results obtained with this immunotoxin by (Wels et al 1992, supra; Wels et al 1995, supra). We undoubtedly demonstrated that reformatting the monovalent scFv immunotoxin into a bivalent IgG improved dramatically the cytotoxic activities of this anti-ErbB2 immunotoxin. Taken together, the cytotoxic activity of both immunotoxins correlates with the binding affinities obtained for the two immunotoxins by the whole-cell ELISA (FIG. 11) and matches the cellular ErbB2 binding activities obtained by flow cytometry (FIG. 12) against the same set of tumor cell lines. This further emphasizes the superiority of the bivalent chFRP5 IgG1 antibody over its monovalent scFv derivative. This superiority is mainly important when evaluating an immunotoxin for therapeutic application as the affinity of the antibody counterpart is a major determining factor in establishing how fast it will bind to a tumor cell and how quickly it will released from the antigen-bearing tumor cell (Henderikx et al 2002, supra). Since the residence time once within the tumor mass is suggested to be controlled by affinity and avidity (Milenic et al 1991, Cancer Res 51 (23 Pt 1:6363-71) bivalent antibodies may be advantageous.

TABLE 3

In vitro cell-killing activity of chFRP5-ZZ-PE38 and scFv(FRP5)-ETA

| Cell line | Number of ErbB2 receptors | ChFRP5-ZZ-PE38 | $IC_{50}$ (PM) scFv(FRP5)-ETA | ChFRP5-ZZ-PE38 + chFRP5 | scFv(FRP5)-ETA + chFRP5 |
|---|---|---|---|---|---|
| SKBR3 | $1.5 \times 10^6$ | 30 | 1000 | 10000 | >100000 |
| A431 | $2 \times 10^4$ | 10 | 52 | 10000 | >100000 |
| MCF7 | <1000 | 300 | >10000 | >100000 | >100000 |
| MDA-MB231 | <1000 | 30000 | >100000 | >100000 | >100000 |

Example 12

Functional Stability Analysis of chFRP5-ZZ-PE38 Immunoconjugate Complex

In order to estimate the stability of the ZZ-Fc affinity connection within the chFRP5-ZZ-PE38 complex we incubated the purified immunoconjugate at 37° C. for varying periods in the presence of 10-fold molar excess of protein-A purified human IgG as competitor before it was tested for cellular-ErbB2 binding of SKBR3 cells by whole-cell ELISA. The results (FIG. 17A) show that when incubated in the presence of human IgG competitors, chFRP5-ZZ-PE38 immunoconjugate lost more then 80% of its binding activities after 24 hr as compared to untreated chFRP5-ZZ-PE38 that retain full binding activities even after 7 days at 37° C. However, since commercial protein-A purified human IgG antibodies do not represent an accurate state of protein A-binding immunoglobulins present in human serum, we also estimated the functional stability of the immunoconjugate complex subsequent to incubation at 37° C. for 72 h in 100% human serum from three individual healthy donors before tested for cellular-ErbB2 binding of SKBR3 cells. The results (FIG. 17B) show that with all three human sera tested; chFRP5-ZZ-PE38 immunoconjugate lost only 10-30% of its binding activities as compared to the immunoconjugate complex that was incubated in PBS. The modest loss of activity obtained in this assay compared with the drastic loss of activity seen after pre-incubation of the immunoconjugate in the presence of protein-A purified human IgG antibodies, represents a more genuine condition in which the functional stability of chFRP5-ZZ-PE38 immunoconjugate should be tested since it is mimicking the conditions in which the functional stability of the chFRP5-ZZ-PE38 immunoconjugate will encounter in a live animal model. In particular, not all human serum immunoglobulins have the capability of affinity binding to ZZ domain, while commercial human IgG antibodies as used for the competition assay are routinely all protein-A purified, and thus represent an enriched population of high-affinity ZZ domain binders.

Example 13

Construction of Crosslinked chFRP5-ZZ-PE38 Immunoconjugate

To circumvent the undesirable event in which the affinity-interaction between chFRP5 Fc domain and the ZZ-PE38 component could be competed off post-formation by protein-A-binding immunoglobulin or immunoglobulin-like competitors, a crosslinked derivative of the chFRP5-ZZ-PE38 immunoconjugate complex was prepared using the crosslinking reagent BS$^3$ (Pierce, USA). Following the crosslinking reaction, more then 80% of the immunoconjugate was covalently crosslinked as indicated by SDS-PAGE analysis (FIG. 18A). The crosslinked derivative had a total size of about 200 kDa consisting of covalently linked heavy and light chains of chFRP5 IgG1 (150 kDa) together with the 50 kDa ZZ-PE38 component. When evaluated for antigen binding, the crosslinked-chFRP5-ZZ-PE38 retained the same apparent affinities to cellular-ErbB2 of human SKBR3 tumor cells as the non-crosslinked derivative (FIG. 18B). This confirmed that the crosslinking process did not undermine the binding activity of the immunoconjugate. When tested for functional stability followed incubation for 24 h at 37° C. in the presence of 10-fold molar excess of the ZZ-binding human IgG1 antibody as competitor, the un-conjugated chFRP5-ZZ-PE38 lost more then 80% of its binding activity, while the crosslinked derivative lost only 21% of its binding capability (FIG. 18B). This loss of activity probably corresponds to the fraction of chFRP5-ZZ-PE38 that was not covalently-linked during the crosslinking process i.e. about 80% efficiency in crosslinking was observed. Furthermore, incubation of the crosslinked-immunoconjugate in 100% human serum did not result in any loss of binding activity compared with a decrease of about 17% for the non-crosslinked derivative.

We further evaluated the functional stability and cytotoxic activities of the crosslinked-chFRP5-ZZ-PE38 complex by analyzing cell-killing activities of the modified immunoconjugate following 24 h incubation at 37° C. with protein-A purified human IgG antibodies (FIG. 19A) or in the presence of 100% human sera (FIG. 19B). While the crosslinking process did not undermine the binding affinity of the covalent-linked immunoconjugate, the cell-killing assays demonstrated that there was some reduction of in the cytotoxic activity of the crosslinked-chFRP5-ZZ-PE38 as indicated by $IC_{50}$ values of 1.8 ng/ml vs 6 ng/ml (Table 4). However, while the non-crosslinked derivative was totally non-toxic to A431 cells following incubation with human IgG1 competitors ($IC_{50}$ of >1000 ng/ml), the crosslinked-immunoconjugate on the other hand retained most of its cytotoxic activity with $IC_{50}$ values of 11 ng/ml. As with the whole-cell ELISA results (FIG. 19B), incubation of the crosslinked-immunoconjugate in 100% human serum did not result in any loss of cytotoxic activity while moderate reduction in cell-killing activities was observed for the non-crosslinked derivative with $IC_{50}$ values of 2.7 ng/ml. Taken together, the results show that crosslinking of chFRP5-ZZ-PE38 does not affect its binding affinities and further significantly improves its functional stability as compared to the non-crosslinked derivative. However crosslinking may lead to a reduction in the cytotoxic activity of the immunoconjugate, suggesting that "fine tuning" of the crosslinking conditions is required to fully maintain the cytotoxic activity. The observed loss in cytotoxicity may result to damage to the toxin moiety. A derivative of PE38, namely PE38-QQR has been reported to be resistant to chemical-conjugation induced damage (Debinski and Pastan 1994, Bioconjug Chem 5, 40-6).

TABLE 4

In vitro cell killing activities of crosslinked-chFRP5-ZZ-PE38

| Cell line | Number of ErbB2 receptors | $IC_{50}$ (ng/ml) | | | | | |
|---|---|---|---|---|---|---|---|
| | | ChFRP5-ZZ-PE38 | ChFRP5-ZZ-PE38 + Commercial hIgG1 | ChFRP5-ZZ-PE38 + Human serum | Crosslinked chFRP5-ZZ-PE38 | Crosslinked chFRP5-ZZ-PE38 + Commercial hIgG1 | Crosslinked chFRP5-ZZ-PE38 + Human serum |
| A431 | $2 \times 10^4$ | 1.8 | >1000 | 2.7 | 6 | 11 | 6 |

Example 14

In Vivo Characterization of chFRP5-ZZ-PE38 in Animal Models

To evaluate the in vivo behavior of the chFRP5-ZZ-PE38 immunoconjugate and also evaluated its potential to serve as a therapeutic agent for specific targeting and killing of human tumor cells expressing high level of ErbB2 receptors, a series of in vivo assays was conducted to analyze its toxicity and its pharmacokinetic behavior in BALB/c mice. We further evaluated the anti tumor activity of chFRP5-ZZ-PE38 in specific targeting and killing of tumor xenografts in female BALB/c athymic nude mice. In these studies we compared chFRP5-ZZ-PE38 to the monovalent scFv(FRP5)-ETA immunotoxin.

Example 15

Comparative Pharmacokinetics of chFRP5-ZZ-PE38 and scFv(FRP5)-ETA in Mouse Serum The pharmacokinetic behavior of chFRP5-ZZ-PE38 and scFv(FRP5)-ETA in BALB/c mice was determined by measuring the immunotoxin levels in blood samples drawn from the mice at various time points following i.v. injection of each immunotoxin. Briefly, female BALB/c mice were given a single i.v. dose of 15 μg chFRP5-ZZ-PE38 or 5 μg scFv(FRP5)-ETA (equimolar dose) by injection into the tail vein.

Blood samples were drawn from the orbital vein of mice injected with scFv(FRP5)-ETA at 2, 5, 10, 20, 30, 60, 120 and 240 min after injection and at 2, 5, 10, 20, 30, 60, 120, 240, 480 and 1440 min for mice injected with chFRP5-ZZ-PE38. The immunotoxin levels in the samples was estimated by dot-blot analysis of serum dilutions alongside a two-fold dilution series of chFRP5-ZZ-PE38 (FIG. 20A) or scFv (FRP5)-ETA (FIG. 20B) standards, the concentration of remaining active immunotoxin was determined by incubating dilutions of the serum with A431 cells and measuring cell-killing activity by MTT assay. The pharmacokinetics curves of chFRP5-ZZ-PE38 and scFv(FRP5)-ETA were determined by calculating the results of both the dot-blot and MTT assays and are presented in FIG. 21. The results obtained show that while the chFRP5-ZZ-PE38 immunoconjugate has a serum half-life of 240 min that correlated to the t½ of different IgG-*Pseudomonas* exotoxin A immunoconjugates (Pai et al 1991, Proc Natl Acad Sci USA 88, 3358-62), the recombinant scFv(FRP5)-ETA immunotoxin half-life of only 18 min, similar to previous results obtained for this immunotoxin (Wels et al 1992, Cancer Res 52, 6310-7) and was in agreement to the t½ of other Fv immunotoxins of similar size (Reiter et al 1994, Biochemistry 33, 5451-9; Benhar and Pastan 1995, Clin Cancer Res 1, 1023-1029).

In vitro experiments show that once distributed into the readily accessible extracellular space, the anti tumor efficacy of an immunotoxin is a function of its affinity for the tumor cells and its ability to penetrate into the tumor (Benhar and Pastan, 1995, supra), thus the antibody fragment must stay in the circulation long enough to diffuse from the blood stream to the tumor without being cleared by the kidneys. It was calculated that it should take about 5-6 h for an immunotoxin to equilibrate within the tumors (Benhar and Pastan, 1995 supra). Our pharmacokinetic results predict a considerable advantage for chFRP5-ZZ-PE38 in its anti tumor activity over the scFv(FRP5)-ETA derivative, since the t½ of the latter is only 18 min, there should be significant clearance of scFv (FRP5)-ETA immunotoxin molecules during this period, whereas very small fraction of chFRP5-ZZ-PE38 immunoconjugate would be cleared at the same period of time.

Example 16

Toxicity of ZZ-PE38 and ZZ-PE38 Immunoconjugates in Mice

The single-dose mouse $LD_{50}$ of ZZ-PE38 fusion protein and three immunoconjugates; chFRP5-ZZ-PE38, crosslinked-chFRP5-ZZ-PE38 and hIgG-ZZ-PE38 was evaluated in female BALB/c mice that were given a single i.v. injection with different doses of each protein. All mice were monitored for weight loss or death for 14 days postinjection. The results of the toxicity assay (Table 5) show that there is a significant difference in toxicity between the chFRP5-ZZ-PE38 and human IgG-ZZ-PE38 immunoconjugates as indicated by $LD_{50}$ of 0.75-1 mg/kg vs 2.5 mg/kg respectively. This difference in toxicity can be the consequence of a weaker affinity conjugation of the ZZ-PE38 component to the Fc domain of chFRP5 IgG1 which can lead to unspecific binding of the ZZ-PE38 fusion protein to endogenous mouse immunoglobulins that have stronger affinity to the ZZ-PE38 component. In contrast, covalent-crosslinking of the chFRP5-ZZ-PE38 abrogated the excessive toxicity as mice were not killed following injection with 1.25 mg/kg of the crosslinked-chFRP5-ZZ-PE38 derivative up to 14 days postinjection. However, when ZZ-PE38 was injected to mice it was significantly toxic with an $LD_{50}$ of 0.375 mg/kg. This highlights the need for optimization of a crosslinking method, or alternative linking methods that preserve the integrity of the IgG-ZZ-PE38 complex and its full cytotoxic potency.

Example 17

Anti Tumor Activity of chFRP5-ZZ-PE38 Immunotoxin in Nude Mice

To study the in vivo activity of chFRP5-ZZ-PE38 immunoconjugate, we evaluated its anti tumor activity in the eradication of A431 tumor xenografts in athymic nude mice. We further compared the therapeutic potential of the bivalent immunoconjugate chFRP5-ZZ-PE38 with that of the monovalent scFv(FRP5)-ETA. Tumors were induced in athymic nude mice by s.c. injection of $1.5 \times 10^6$ A431 cells on day 0. Treatment was initiated on day 9 when the tumors averaged 30-40 mm³ in volume, and consisted of five i.v. injections on days 9, 12, 15, 18, and 21 of various doses of the immunotoxins. Control mice were treated with PBS only. As shown in FIGS. 22 and 23, chFRP5-ZZ-PE38 exhibited a significant antitumor effect. Mice treated at a dose of 0.5 mg/kg (FIG. 23D) exhibited complete remission of the tumor that lasted for two months until the animals were sacrificed, and mice treated at a dose of 0.25 mg/kg (FIG. 23C), exhibited arrested tumor growth, in most cases for the duration of the experiment i.e until the animals were sacrificed after two months. In some animals, tumor growth resumed a few weeks after treatment.

In contrast, treatment of mice with 0.25 mg/kg of the monovalent scFv(FRP5)-ETA (FIG. 23B), a dose which correlates to 1.5 and 3 fold higher molar concentration as compared to the doses used with the bivalent immunoconjugate, resulted in minimal to no effect on tumor growth. Tumor size in control mice treated with PBS (FIG. 23A) increased progressively. By day 30, tumor size in control and scFv(FRP5)-ETA treated animals was about 1.0 cm³. When the experiment was terminated on day 30 by euthanization of the animals, the size of the tumors in the scFv(FRP5)-ETA-treated animals was 96% that of the tumor size in the control group as compared to 5.5% and 19% for animals treated with 0.5 and 0.25 mg/kg chFRP5-ZZ-PE38 respectively. No drug-induced toxicity in mice was observed at the doses of scFv(FRP5)-ETA and chFRP5-ZZ-PE38 used in this study.

The less than optimal anti tumor effects obtained with scFv(FRP5)-ETA at a dose of 0.25 mg/kg was not surprising as it was previously reported that A431 xenografts bearing athymic nude mice receiving twice-daily i.p. injections of 0.25 mg/kg of scFv(FRP5)-ETA for a total of 10 days led only to a modest inhibition of tumor growth, yielding tumors 44% of the size of the control group (Wels et al 1995, Int J Cancer 60, 137-44). Our results demonstrate the superiority of the bivalent immunoconjugate over its monovalent counterpart in targeted cancer therapy of live athymic nude mice bearing A431 tumor xenografts.

What is claimed is:

1. A method for killing a target cell in a subject in need thereof, which comprises:
   providing a recombinant fusion protein that comprises an immunoglobulin Fc-binding domain and a truncated form of *Pseudomonas* exotoxin;
   providing an antibody which is specific for an antigen present on the target cell and which is capable of being internalized into the target cell;
   combining the antibody and protein to form an antibody-protein combination; and
   exposing the target cell to an effective amount of the antibody-protein combination, thereby selectively killing a target cell in a subject in need thereof.

2. The method of claim 1, wherein the protein comprises an amino acid sequence of SEQ ID NO:1.

3. The method of claim 1, wherein the truncated form of *Pseudomonas* exotoxin comprises an amino acid sequence of SEQ ID NO:3.

4. The method of claim 1, wherein the target cell is selected from the group consisting of a cancer cell, a parasite-infected cell, a virus-infected cell and a pathogen infected cell.

5. The method of claim 4, wherein the cancer cell is derived from the lung, colon, rectum, breast, ovary, prostate gland, head, neck, bone, kidney, liver, skin or the immune system.

6. The method of claim 1, wherein the antigen is selected from the group consisting of a tumor-associated antigen, a pathogen-associated antigen, a parasite-associated antigen, a virus-associated antigen, or any combination thereof.

7. The method of claim 6, wherein the tumor-associated antigen is selected from the group consisting of: MUC1 and ErbB2.

8. The method of claim 1, wherein the exposing comprises intravenously, intraperitonealy, subcutaneously, intramuscularly, or intralymphatically administering the combination to the subject.

9. The method of claim 1, wherein the combining comprises forming a covalent bond between the antibody and the protein, conjugating the antibody and the protein, cross-inking the antibody and the protein, or any combination thereof.

10. A method for treating a subject afflicted with cancer, which comprises administering to the subject a composition comprising a recombinant fusion protein and an antibody specific for an antigen present on a cancer cell, wherein the protein comprises an immunoglobulin Fc-binding domain and a truncated form of *Pseudomonas* exotoxin and the antibody is capable of being internalized into the cell, thereby treating a subject afflicted with cancer.

11. The method of claim 10, wherein the cancer is lung cancer, breast cancer, or a combination thereof.

12. The method of claim 10, wherein the protein comprises an amino acid sequence of SEQ ID NO:1.

13. The method of claim 10, wherein the truncated form of *Pseudomonas* exotoxin comprises an amino acid sequence of SEQ ID NO:3.

14. The method of claim 10, wherein the antigen is MUC1 or ErbB2.

15. The method of claim 10, wherein the administering comprises intravenously, intraperitonealy, subcutaneously, intramuscularly, or intralymphatically administering.

16. The method of claim 10, wherein the protein and the antibody are combined via: conjugation, cross-linking, or covalent bonding to form an antibody-protein combination.

17. The method of claim 1, wherein the protein comprises a first segment which is an immunoglobulin Fc-binding domain present in multiple copies, and a second segment which is a truncated form of *Pseudomonas* exotoxin, and wherein the first and second segments are joined by a peptide linker.

18. The method of claim 1, wherein the Fc-binding domain is derived from *S. aureus* protein A and comprises domain B of protein A or is denoted as ZZ and has the amino acid sequence of SEQ ID NO: 2.

19. The method of claim 10, wherein the protein comprises a first segment which is an immunoglobulin Fc-binding domain present in multiple copies, and a second segment which is a truncated form of *Pseudomonas* exotoxin, and wherein the first and second segments are joined by a peptide linker.

20. The method of claim 1, wherein said antigen is a tumor-associated antigen.

* * * * *

SEQUENCE LISTING

<160> NUMBER OF SEQ ID NOS: 27

<210> SEQ ID NO 1
<211> LENGTH: 492
<212> TYPE: PRT
<213> ORGANISM: Artificial Sequence
<220> FEATURE:
<223> OTHER INFORMATION: Synthetic

<400> SEQUENCE: 1

Met Lys Tyr Leu Leu Pro Thr Ala Ala Ala Gly Leu Leu Leu Leu Ala
1               5                   10                  15

Ala Gln Pro Ala Met Ala Met Val Asp Asn Lys Phe Asn Lys Glu Gln
            20                  25                  30

Gln Asn Ala Phe Tyr Glu Ile Leu His Leu Pro Asn Leu Asn Glu Glu
        35                  40                  45

Gln Arg Asn Ala Phe Ile Gln Ser Leu Lys Asp Asp Pro Ser Gln Ser
    50                  55                  60

Ala Asn Leu Leu Ala Glu Ala Lys Lys Leu Asn Asp Ala Gln Ala Pro
65                  70                  75                  80

Lys Val Asp Asn Lys Phe Asn Lys Glu Gln Gln Asn Ala Phe Tyr Glu
                85                  90                  95

Ile Leu His Leu Pro Asn Leu Asn Glu Glu Gln Arg Asn Ala Phe Ile
            100                 105                 110

Gln Ser Leu Lys Asp Asp Pro Ser Gln Ser Ala Asn Leu Leu Ala Glu
        115                 120                 125

Ala Lys Lys Leu Asn Asp Ala Gln Ala Pro Lys Ala Ala Ala Ser Gly
    130                 135                 140

Gly Pro Glu Gly Gly Ser Leu Ala Ala Leu Thr Ala His Gln Ala Cys
145                 150                 155                 160

His Leu Pro Leu Glu Thr Phe Thr Arg His Arg Gln Pro Arg Gly Trp
                165                 170                 175

Glu Gln Leu Glu Gln Cys Gly Tyr Pro Val Gln Arg Leu Val Ala Leu
            180                 185                 190

Tyr Leu Ala Ala Arg Leu Ser Trp Asn Gln Val Asp Gln Val Ile Arg
        195                 200                 205

Asn Ala Leu Ala Ser Pro Gly Ser Gly Gly Asp Leu Gly Glu Ala Ile
    210                 215                 220

Arg Glu Gln Pro Glu Gln Ala Arg Leu Ala Leu Thr Leu Ala Ala Ala
225                 230                 235                 240

Glu Ser Glu Arg Phe Val Arg Gln Gly Thr Gly Asn Asp Glu Ala Gly
                245                 250                 255

Ala Ala Asn Gly Pro Ala Asp Ser Gly Asp Ala Leu Leu Glu Arg Asn
            260                 265                 270

Tyr Pro Thr Gly Ala Glu Phe Leu Gly Asp Gly Gly Asp Val Ser Phe
        275                 280                 285

Ser Thr Arg Gly Thr Gln Asn Trp Thr Val Glu Arg Leu Leu Gln Ala
    290                 295                 300

His Arg Gln Leu Glu Glu Arg Gly Tyr Val Phe Val Gly Tyr His Gly
305                 310                 315                 320

Thr Phe Leu Glu Ala Ala Gln Ser Ile Val Phe Gly Gly Val Arg Ala
                325                 330                 335

Arg Ser Gln Asp Leu Asp Ala Ile Trp Arg Gly Phe Tyr Ile Ala Gly
            340                 345                 350

-continued

Asp Pro Ala Leu Ala Tyr Gly Tyr Ala Gln Asp Gln Glu Pro Asp Ala
            355                 360                 365

Arg Gly Arg Ile Arg Asn Gly Ala Leu Leu Arg Val Tyr Val Pro Arg
370                 375                 380

Ser Ser Leu Pro Gly Phe Tyr Arg Thr Ser Leu Thr Leu Ala Ala Pro
385                 390                 395                 400

Glu Ala Ala Gly Glu Val Glu Arg Leu Ile Gly His Pro Leu Pro Leu
                405                 410                 415

Arg Leu Asp Ala Ile Thr Gly Pro Glu Glu Gly Gly Arg Leu Glu
            420                 425                 430

Thr Ile Leu Gly Trp Pro Leu Ala Glu Arg Thr Val Val Ile Pro Ser
            435                 440                 445

Ala Ile Pro Thr Asp Pro Arg Asn Val Gly Gly Asp Leu Asp Pro Ser
    450                 455                 460

Ser Ile Pro Asp Lys Glu Gln Ala Ile Ser Ala Leu Pro Asp Tyr Ala
465                 470                 475                 480

Ser Gln Pro Gly Lys Pro Pro Arg Glu Asp Leu Lys
                485                 490

<210> SEQ ID NO 2
<211> LENGTH: 139
<212> TYPE: PRT
<213> ORGANISM: Artificial Sequence
<220> FEATURE:
<223> OTHER INFORMATION: Synthetic

<400> SEQUENCE: 2

Met Lys Tyr Leu Leu Pro Thr Ala Ala Ala Gly Leu Leu Leu Leu Ala
1               5                   10                  15

Ala Gln Pro Ala Met Ala Met Val Asp Asn Lys Phe Asn Lys Glu Gln
            20                  25                  30

Gln Asn Ala Phe Tyr Glu Ile Leu His Leu Pro Asn Leu Asn Glu Glu
        35                  40                  45

Gln Arg Asn Ala Phe Ile Gln Ser Leu Lys Asp Asp Pro Ser Gln Ser
    50                  55                  60

Ala Asn Leu Leu Ala Glu Ala Lys Lys Leu Asn Asp Ala Gln Ala Pro
65                  70                  75                  80

Lys Val Asp Asn Lys Phe Asn Lys Glu Gln Gln Asn Ala Phe Tyr Glu
                85                  90                  95

Ile Leu His Leu Pro Asn Leu Asn Glu Glu Gln Arg Asn Ala Phe Ile
            100                 105                 110

Gln Ser Leu Lys Asp Asp Pro Ser Gln Ser Ala Asn Leu Leu Ala Glu
        115                 120                 125

Ala Lys Lys Leu Asn Asp Ala Gln Ala Pro Lys
    130                 135

<210> SEQ ID NO 3
<211> LENGTH: 345
<212> TYPE: PRT
<213> ORGANISM: Artificial Sequence
<220> FEATURE:
<223> OTHER INFORMATION: Synthetic

<400> SEQUENCE: 3

Gly Gly Ser Leu Ala Ala Leu Thr Ala His Gln Ala Cys His Leu Pro
1               5                   10                  15

Leu Glu Thr Phe Thr Arg His Arg Gln Pro Arg Gly Trp Glu Gln Leu
            20                  25                  30

Glu Gln Cys Gly Tyr Pro Val Gln Arg Leu Val Ala Leu Tyr Leu Ala
            35                  40                  45

Ala Arg Leu Ser Trp Asn Gln Val Asp Gln Val Ile Arg Asn Ala Leu
 50                  55                  60

Ala Ser Pro Gly Ser Gly Gly Asp Leu Gly Glu Ala Ile Arg Glu Gln
 65                  70                  75                  80

Pro Glu Gln Ala Arg Leu Ala Leu Thr Leu Ala Ala Glu Ser Glu
                85                  90                  95

Arg Phe Val Arg Gln Gly Thr Gly Asn Asp Glu Ala Gly Ala Ala Asn
                100                 105                 110

Gly Pro Ala Asp Ser Gly Asp Ala Leu Leu Glu Arg Asn Tyr Pro Thr
            115                 120                 125

Gly Ala Glu Phe Leu Gly Asp Gly Gly Asp Val Ser Phe Ser Thr Arg
130                 135                 140

Gly Thr Gln Asn Trp Thr Val Glu Arg Leu Leu Gln Ala His Arg Gln
145                 150                 155                 160

Leu Glu Glu Arg Gly Tyr Val Phe Val Gly Tyr His Gly Thr Phe Leu
                165                 170                 175

Glu Ala Ala Gln Ser Ile Val Phe Gly Gly Val Arg Ala Arg Ser Gln
                180                 185                 190

Asp Leu Asp Ala Ile Trp Arg Gly Phe Tyr Ile Ala Gly Asp Pro Ala
            195                 200                 205

Leu Ala Tyr Gly Tyr Ala Gln Asp Gln Glu Pro Asp Ala Arg Gly Arg
210                 215                 220

Ile Arg Asn Gly Ala Leu Leu Arg Val Tyr Val Pro Arg Ser Ser Leu
225                 230                 235                 240

Pro Gly Phe Tyr Arg Thr Ser Leu Thr Leu Ala Ala Pro Glu Ala Ala
                245                 250                 255

Gly Glu Val Glu Arg Leu Ile Gly His Pro Leu Pro Leu Arg Leu Asp
                260                 265                 270

Ala Ile Thr Gly Pro Glu Glu Gly Gly Arg Leu Glu Thr Ile Leu
            275                 280                 285

Gly Trp Pro Leu Ala Glu Arg Thr Val Val Ile Pro Ser Ala Ile Pro
290                 295                 300

Thr Asp Pro Arg Asn Val Gly Gly Asp Leu Asp Pro Ser Ser Ile Pro
305                 310                 315                 320

Asp Lys Glu Gln Ala Ile Ser Ala Leu Pro Asp Tyr Ala Ser Gln Pro
                325                 330                 335

Gly Lys Pro Pro Arg Glu Asp Leu Lys
            340                 345

<210> SEQ ID NO 4
<211> LENGTH: 613
<212> TYPE: PRT
<213> ORGANISM: Artificial Sequence
<220> FEATURE:
<223> OTHER INFORMATION: Synthetic

<400> SEQUENCE: 4

Ala Glu Glu Ala Phe Asp Leu Trp Asn Glu Cys Ala Lys Ala Cys Val
1               5                   10                  15

Leu Asp Leu Lys Asp Gly Val Arg Ser Ser Arg Met Ser Val Asp Pro
                20                  25                  30

Ala Ile Ala Asp Thr Asn Gly Gln Gly Val Leu His Tyr Ser Met Val
            35                  40                  45

Leu Glu Gly Gly Asn Asp Ala Leu Lys Leu Ala Ile Asp Asn Ala Leu

```
            50                  55                  60
Ser Ile Thr Ser Asp Gly Leu Thr Ile Arg Leu Glu Gly Gly Val Glu
 65                  70                  75                  80

Pro Asn Lys Pro Val Arg Tyr Ser Tyr Thr Arg Gln Ala Arg Gly Ser
                 85                  90                  95

Trp Ser Leu Asn Trp Leu Val Pro Ile Gly His Glu Lys Pro Ser Asn
                100                 105                 110

Ile Lys Val Phe Ile His Glu Leu Asn Ala Gly Asn Gln Leu Ser His
                115                 120                 125

Met Ser Pro Ile Tyr Thr Ile Glu Met Gly Asp Glu Leu Leu Ala Lys
130                 135                 140

Leu Ala Arg Asp Ala Thr Phe Phe Val Arg Ala His Glu Ser Asn Glu
145                 150                 155                 160

Met Gln Pro Thr Leu Ala Ile Ser His Ala Gly Val Ser Val Val Met
                165                 170                 175

Ala Gln Thr Gln Pro Arg Arg Glu Lys Arg Trp Ser Glu Trp Ala Ser
                180                 185                 190

Gly Lys Val Leu Cys Leu Leu Asp Pro Leu Asp Gly Val Tyr Asn Tyr
                195                 200                 205

Leu Ala Gln Gln Arg Cys Asn Leu Asp Asp Thr Trp Glu Gly Lys Ile
210                 215                 220

Tyr Arg Val Leu Ala Gly Asn Pro Ala Lys His Asp Leu Asp Ile Lys
225                 230                 235                 240

Pro Thr Val Ile Ser His Arg Leu His Phe Pro Glu Gly Gly Ser Leu
                245                 250                 255

Ala Ala Leu Thr Ala His Gln Ala Cys His Leu Pro Leu Glu Thr Phe
                260                 265                 270

Thr Arg His Arg Gln Pro Arg Gly Trp Glu Gln Leu Glu Gln Cys Gly
                275                 280                 285

Tyr Pro Val Gln Arg Leu Val Ala Leu Tyr Leu Ala Ala Arg Leu Ser
290                 295                 300

Trp Asn Gln Val Asp Gln Val Ile Arg Asn Ala Leu Ala Ser Pro Gly
305                 310                 315                 320

Ser Gly Gly Asp Leu Gly Glu Ala Ile Arg Glu Gln Pro Glu Gln Ala
                325                 330                 335

Arg Leu Ala Leu Thr Leu Ala Ala Ala Glu Ser Glu Arg Phe Val Arg
                340                 345                 350

Gln Gly Thr Gly Asn Asp Glu Ala Gly Ala Ala Asn Ala Asp Val Val
                355                 360                 365

Ser Leu Thr Cys Pro Val Ala Ala Gly Glu Cys Ala Gly Pro Ala Asp
370                 375                 380

Ser Gly Asp Ala Leu Leu Glu Arg Asn Tyr Pro Thr Gly Ala Glu Phe
385                 390                 395                 400

Leu Gly Asp Gly Gly Asp Val Ser Phe Ser Thr Arg Gly Thr Gln Asn
                405                 410                 415

Trp Thr Val Glu Arg Leu Leu Gln Ala His Arg Gln Leu Glu Glu Arg
                420                 425                 430

Gly Tyr Val Phe Val Gly Tyr His Gly Thr Phe Leu Glu Ala Ala Gln
                435                 440                 445

Ser Ile Val Phe Gly Gly Val Arg Ala Arg Ser Gln Asp Leu Asp Ala
                450                 455                 460

Ile Trp Arg Gly Phe Tyr Ile Ala Gly Asp Pro Ala Leu Ala Tyr Gly
465                 470                 475                 480
```

```
Tyr Ala Gln Asp Gln Glu Pro Asp Ala Arg Gly Ile Arg Asn Gly
                485                 490                 495

Ala Leu Leu Arg Val Tyr Val Pro Arg Ser Ser Leu Pro Gly Phe Tyr
            500                 505                 510

Arg Thr Ser Leu Thr Leu Ala Ala Pro Glu Ala Ala Gly Glu Val Glu
            515                 520                 525

Arg Leu Ile Gly His Pro Leu Pro Leu Arg Leu Asp Ala Ile Thr Gly
        530                 535                 540

Pro Glu Glu Glu Gly Gly Arg Leu Glu Thr Ile Leu Gly Trp Pro Leu
545                 550                 555                 560

Ala Glu Arg Thr Val Val Ile Pro Ser Ala Ile Pro Thr Asp Pro Arg
                565                 570                 575

Asn Val Gly Gly Asp Leu Asp Pro Ser Ser Ile Pro Asp Lys Glu Gln
            580                 585                 590

Ala Ile Ser Ala Leu Pro Asp Tyr Ala Ser Gln Pro Gly Lys Pro Pro
        595                 600                 605

Arg Glu Asp Leu Lys
    610

<210> SEQ ID NO 5
<211> LENGTH: 6972
<212> TYPE: DNA
<213> ORGANISM: Artificial Sequence
<220> FEATURE:
<223> OTHER INFORMATION: Synthetic

<400> SEQUENCE: 5
agatctcgat cccgcgaaat taatacgact cactataggg gaattgtgag cggataacaa      60
ttcccctcta gaaataattt tgtttaactt taagaaggag atatacatat gaaatacctg     120
ctgccgaccg ctgctgctgg tctgctgctc ctcgctgccc agccggcgat ggccatggta     180
gacaacaaat tcaacaaaga caacaaaacg cgttctatg  agatcttaca tttacctaac     240
ttaaacgaag aacaacgaaa cgccttcatc caaagtttaa aagatgaccc aagccaaagc     300
gctaaccttt tagcagaagc taaaaagcta aatgatgctc aggcgccgaa agtagacaac     360
aaattcaaca agaacaaca aaacgcgttc tatgagatct acatttacc taacttaaac      420 gaagaacaac gaaacgcctt catccaaagt ttaaaagatg acccaagcca aagcgctaac     480
cttttagcag aagctaaaaa gctaaatgat gctcaggcgc cgaaagcggc cgcatccgga     540
ggtcccgagg cggcagcct ggccgcgctg accgcgcacc aggcttgcca cctgccgctg     600
gagactttca cccgtcatcg ccagccgcgc ggctgggaac aactggagca gtgcggctat     660
ccggtgcagc ggctggtcgc cctctacctg gcggcgcggc tgtcgtggaa ccaggtcgac     720
caggtgatcc gcaacgccct ggccagcccc ggcagcggcg gcgacctggg cgaagcgatc     780
cgcgagcagc cggagcaggc ccgtctggcc ctgaccctgg ccgccgccga gagcgagcgc     840
ttcgtccggc agggcaccgg caacgacgag gccggcgcgg ccaacggccc ggcggacagc     900
ggcgacgccc tgctggagcg caactatccc actggcgcgg agttcctcgg cgacggcggc     960
gacgtcagct tcagcacccg cggcacgcag aactggacga tggagcggct gctccaggcg    1020
caccgccaac tggaggagcg cggctatgtg ttcgtcggct accacggcac cttcctcgaa    1080
gcggcgcaaa gcatcgtctt cggcggggtg cgcgcgcgca gccaggacct cgacgcgatc    1140
tggcgcggtt tctatatcgc cggcgatccg cgctggcct acggctacgc ccaggaccag    1200
gaacccgacg cacgcggccg gatccgcaac ggtgccctgc tgcgggtcta tgtgccgcgc    1260
tcgagcctgc cgggcttcta ccgcaccagc ctgaccctgg ccgcgccgga ggcggcgggc    1320
```

```
gaggtcgaac ggctgatcgg ccatccgctg ccgctgcgcc tggacgccat caccggcccc    1380
gaggaggaag gcgggcgcct ggagaccatt ctcggctggc cgctggccga gcgcaccgtg    1440
gtgattccct cggcgatccc caccgacccg cgcaacgtcg gcggcgacct cgacccgtcc    1500
agcatccccg acaaggaaca ggcgatcagc gccctgccgg actacgccag ccagcccggc    1560
aaaccgccgc gcgaggacct gaagtaactg ccgcgaccgg ccggctccct tcgcaggagc    1620
cggccttctc ggggcctggc catacatcag gttttcctga tgccagccca atcgaatatg    1680
aattcgagct ccgtcgacaa gcttgcggcc gcactgagcc accaccacca ccaccactga    1740
gatccggctg ctaacaaagc ccgaaaggaa gctgagttgg ctgctgccac cgctgagcaa    1800
taactagcat aacccCttgg ggcctctaaa cgggtcttga ggggttttTt gctgaaagga    1860
ggaactatat ccggattggc gaatgggacg cgccctgtag cggcgcatta agcgcggcgg    1920
gtgtggtggt tacgcgcagc gtgaccgcta cacttgccag cgccctagcg cccgctcctt    1980
tcgctttctt cccttccttt ctcgccacgt tcgccggctt tccccgtcaa gctctaaatc    2040
gggggctccc tttagggttc cgatttagtg ctttacggca cctcgacccc aaaaaacttg    2100
attagggtga tggttcacgt agtgggccat cgccctgata cggttttt cgccctttga    2160 cgttggagtc cacgttcttt aatagtggac tcttgttcca aactggaaca acactcaacc    2220
ctatctcggt ctattctttt gatttataag ggattttgcc gatttcggcc tattggttaa    2280
aaaatgagct gatttaacaa aaatttaacg cgaattttaa caaaatatta cgtttacaa     2340 tttcaggtgg cacttttcgg ggaaatgtgc gcggaacccc tatttgttta ttttctaaa     2400 tacattcaaa tatgtatccg ctcatgagac aataaccctg ataaatgctt caataatatt    2460
gaaaaaggaa gagtatgagt attcaacatt tccgtgtcgc ccttattccc ttttttgcgg    2520
cattttgcct tcctgttttt gctcacccag aaacgctggt gaaagtaaaa gatgctgaag    2580
atcagttggg tgcacgagtg ggttacatcg aactggatct caacagcggt aagatccttg    2640
agagttttcg ccccgaagaa cgttttccaa tgatgagcac ttttaaagtt ctgctatgtg    2700
gcgcggtatt atcccgtatt gacgccgggc aagagcaact cggtcgccgc atacactatt    2760
ctcagaatga cttggttgag tactcaccag tcacagaaaa gcatcttacg gatggcatga    2820
cagtaagaga attatgcagt gctgccataa ccatgagtga taacactgcg gccaacttac    2880
ttctgacaac gatcggagga ccgaaggagc taaccgcttt tttgcacaac atgggggatc    2940
atgtaactcg ccttgatcgt tgggaaccgg agctgaatga agccatacca aacgacgagc    3000
gtgacaccac gatgcctgca gcaatggcaa caacgttgcg caaactatta actggcgaac    3060
tacttactct agcttcccgg caacaattaa tagactggat ggaggcggat aaagttgcag    3120
gaccacttct gcgctcggcc cttccggctg gctggtttat tgctgataaa tctggagccg    3180
gtgagcgtgg gtctcgcggt atcattgcag cactggggcc agatggtaag ccctcccgta    3240
tcgtagttat ctacacgacg gggagtcagg caactatgga tgaacgaaat agacagatcg    3300
ctgagatagg tgcctcactg attaagcatt ggtaactgtc agaccaagtt tactcatata    3360
tactttagat tgatttaaaa cttcattttt aatttaaaag gatctaggtg aagatccttt    3420
ttgataatct catgaccaaa atcccttaac gtgagttttc gttccactga gcgtcagacc    3480
ccgtagaaaa gatcaaagga tcttcttgag atccttttt tctgcgcgta atctgctgct    3540
tgcaaacaaa aaaaccaccg ctaccagcgg tggtttgttt gccggatcaa gagctaccaa    3600 ctcttttttcc gaaggtaact ggcttcagca gagcgcagat accaaatact gtccttctag    3660
tgtagccgta gttaggccac cacttcaaga actctgtagc accgcctaca tacctcgctc    3720
```

```
tgctaatcct gttaccagtg gctgctgcca gtggcgataa gtcgtgtctt accgggttgg   3780
actcaagacg atagttaccg gataaggcgc agcggtcggg ctgaacgggg ggttcgtgca   3840
cacagcccag cttggagcga acgacctaca ccgaactgag atacctacag cgtgagctat   3900
gagaaagcgc cacgcttccc gaagggagaa aggcggacag gtatccggta agcggcaggg   3960
tcggaacagg agagcgcacg agggagcttc caggggaaac gcctggtat ctttatagtc    4020 ctgtcgggtt cgccacctc tgacttgagc gtcgattttt gtgatgctcg tcaggggggc    4080
ggagcctatg gaaaaacgcc agcaacgcgg ccttttacg gttcctggcc ttttgctggc    4140
cttttgctca catgttcttt cctgcgttat cccctgattc tgtggataac cgtattaccg    4200
cctttgagtg agctgatacc gctcgccgca gccgaacgac cgagcgcagc gagtcagtga    4260
gcgaggaagc ggaagagcgc ctgatgcggt attttctcct tacgcatctg tgcggtattt    4320
cacaccgcat atatggtgca ctctcagtac aatctgctct gatgccgcat agttaagcca    4380
gtatacactc cgctatcgct acgtgactgg gtcatggctg cgccccgaca cccgccaaca    4440
cccgctgacg cgccctgacg ggcttgtctg ctcccggcat ccgcttacag acaagctgtg    4500
accgtctccg ggagctgcat gtgtcagagg ttttcaccgt catcaccgaa acgcgcgagg    4560
cagctgcggt aaagctcatc agcgtggtcg tgaagcgatt cacagatgtc tgcctgttca    4620
tccgcgtcca gctcgttgag tttctccaga agcgttaatg tctggcttct gataaagcgg    4680
gccatgttaa gggcggtttt tcctgtttg gtcactgatg cctccgtgta aggggggattt    4740 ctgttcatgg gggtaatgat accgatgaaa cgagagagga tgctcacgat acgggttact    4800
gatgatgaac atgcccggtt actggaacgt tgtgagggta acaactggc ggtatggatg     4860 cggcgggacc agagaaaaat cactcagggt caatgccagc gcttcgttaa tacagatgta    4920
ggtgttccac agggtagcca gcagcatcct gcgatgcaga tccggaacat aatggtgcag    4980
ggcgctgact tccgcgtttc cagactttac gaaacacgga aaccgaagac cattcatgtt    5040
gttgctcagg tcgcagacgt tttgcagcag cagtcgcttc acgttcgctc gcgtatcggt    5100
gattcattct gctaaccagt aaggcaaccc cgccagccta gccgggtcct caacgacagg    5160
agcacgatca tgcgcacccg tggggccgcc atgccggcga taatggcctg cttctcgccg    5220
aaacgtttgg tggcgggacc agtgacgaag gcttgagcga gggcgtgcaa gattccgaat    5280
accgcaagcg acaggccgat catcgtcgcg ctccagcgaa agcggtcctc gccgaaaatg    5340
acccagagcg ctgccggcac ctgtcctacg agttgcatga taaagaagac agtcataagt    5400
gcggcgacga tagtcatgcc ccgcgcccac cggaaggagc tgactgggtt gaaggctctc    5460
aagggcatcg gtcgagatcc cggtgcctaa tgagtgagct aacttacatt aattgcgttg    5520
cgctcactgc ccgctttcca gtcgggaaac ctgtcgtgcc agctgcatta atgaatcggc    5580
caacgcgcgg ggagaggcgg tttgcgtatt gggcgccagg gtggttttc ttttcaccag     5640 tgagacgggc aacagctgat tgcccttcac cgcctggccc tgagagagtt gcagcaagcg    5700
gtccacgctg gtttgcccca gcaggcgaaa atcctgtttg atggtggtta acggcgggat    5760
ataacatgag ctgtcttcgg tatcgtcgta tcccactacc gagatatccg caccaacgcg    5820
cagcccggac tcggtaatgg cgcgcattgc gcccagcgcc atctgatcgt tggcaaccag    5880
catcgcagtg ggaacgatgc cctcattcag catttgcatg gtttgttgaa aaccggacat    5940
ggcactccag tcgccttccc gttccgctat cggctgaatt tgattgcgag tgagatattt    6000
atgccagcca gccagacgca gacgcgccga gacagaactt aatgggcccg ctaacagcgc    6060
gatttgctgg tgacccaatg cgaccagatg ctccacgccc agtcgcgtac cgtcttcatg    6120
```

-continued

```
ggagaaaata atactgttga tgggtgtctg gtcagagaca tcaagaaata acgccggaac      6180
attagtgcag gcagcttcca cagcaatggc atcctggtca tccagcggat agttaatgat      6240
cagcccactg acgcgttgcg cgagaagatt gtgcaccgcc gctttacagg cttcgacgcc      6300
gcttcgttct accatcgaca ccaccacgct ggcacccagt tgatcggcgc gagatttaat      6360
cgccgcgaca atttgcgacg gcgcgtgcag ggccagactg gaggtggcaa cgccaatcag      6420
caacgactgt ttgcccgcca gttgttgtgc cacgcggttg ggaatgtaat tcagctccgc      6480
catcgccgct tccactttt cccgcgtttt cgcagaaacg tggctggcct ggttcaccac       6540
gcgggaaacg gtctgataag agacaccggc atactctgcg acatcgtata acgttactgg      6600
tttcacattc accaccctga attgactctc ttccgggcgc tatcatgcca taccgcgaaa      6660
ggttttgcgc cattcgatgg tgtccgggat ctcgacgctc tcccttatgc gactcctgca      6720
ttaggaagca gcccagtagt aggttgaggc cgttgagcac cgccgccgca aggaatggtg      6780
catgcaagga gatggcgccc aacagtcccc cggccacggg gcctgccacc atacccacgc      6840
cgaaacaagc gctcatgagc ccgaagtggc gagcccgatc ttccccatcg gtgatgtcgg      6900
cgatataggc gccagcaacc gcacctgtgg gccggtgat gccggccacg atgcgtccgg       6960
cgtagaggat cg                                                         6972
```

<210> SEQ ID NO 6
<211> LENGTH: 1413
<212> TYPE: DNA
<213> ORGANISM: Artificial Sequence
<220> FEATURE:
<223> OTHER INFORMATION: Synthetic

<400> SEQUENCE: 6

```
atggtagaca caaattcaa caaagaacaa caaaacgcgt tctatgagat cttacattta        60
cctaacttaa acgaagaaca acgaaacgcc ttcatccaaa gtttaaaaga tgacccaagc      120
caaagcgcta accttttagc agaagctaaa aagctaaatg atgctcaggc gccgaaagta      180
gacaacaaat tcaacaaaga caacaaaaac gcgttctatg agatcttaca tttacctaac      240
ttaaacgaag aacaacgaaa cgccttcatc caaagtttaa aagatgaccc aagccaaagc      300
gctaaccttt tagcagaagc taaaaagcta aatgatgctc aggcgccgaa agcggccgca      360
tccggaggtc ccgagggcgg cagcctggcc gcgctgaccg cgcaccaggc ttgccacctg      420
ccgctggaga ctttcacccg tcatcgccag ccgcgcggct gggaacaact ggagcagtgc      480
ggctatccgg tgcagcggct ggtcgccctc tacctggcgg cgcggctgtc gtggaaccag      540
gtcgaccagg tgatccgcaa cgccctggcc agccccggca gcggcggcga cctgggcgaa      600
gcgatccgcg agcagccgga gcaggcccgt ctggccctga ccctggccgc cgccgagagc      660
gagcgcttcg tccggcaggg caccggcaac gacgaggccg cgcggccaa cggcccggcg       720 gacagcggcg acgccctgct ggagcgcaac tatcccactg gcgcggagtt cctcggcgac      780
ggcggcgacg tcagcttcag cacccgcggc acgcagaact ggacggtgga gcggctgctc      840
caggcgcacc gccaactgga ggagcgcggc tatgtgttcg tcggctacca cggcaccttc      900
ctcgaagcgg cgcaaagcat cgtcttcggc ggggtgcgcg cgcgcagcca ggacctcgac      960
gcgatctggc gcggtttcta tatcgccggc gatccggcg tggcctacgg ctacgcccag       1020
gaccaggaac ccgacgcacg cggccggatc cgcaacggtg ccctgctgcg ggtctatgtg      1080
ccgcgctcga gcctgccggg cttctaccgc accagcctga ccctgccgc gccggaggcg       1140 gcgggcgagg tcgaacggct gatcggccat ccgctgccgc tgcgcctgga cgccatcacc      1200
```

```
ggccccgagg aggaaggcgg gcgcctggag accattctcg gctggccgct ggccgagcgc    1260
accgtggtga ttccctcggc gatccccacc gacccgcgca acgtcggcgg cgacctcgac    1320
ccgtccagca tccccgacaa ggaacaggcg atcagcgccc tgccggacta cgccagccag    1380
cccggcaaac cgccgcgcga ggacctgaag taa                                 1413

<210> SEQ ID NO 7
<211> LENGTH: 6302
<212> TYPE: DNA
<213> ORGANISM: Artificial Sequence
<220> FEATURE:
<223> OTHER INFORMATION: Synthetic

<400> SEQUENCE: 7
gtaccgaatt cacattgatt attgagtagt tattaatagt aatcaattac ggggtcatta      60
gttcatagcc catatatgga gttccgcgtt acataactta cggtaaatgg cccgcctggc     120
tgaccgccca acgacccccg cccattgacg tcaataatga cgtatgttcc catagtaacg     180 ccaatagga ctttccattg acgtcaatgg gtggagtatt tacggtaaac tgcccacttg      240
gcagtacatc aagtgtatca tatgccaagt acgcccccta ttgacgtcaa tgacggtaaa     300
tggcccgcct ggcattatgc ccagtacatg accttatggg actttcctac ttggcagtac     360
atctacggtt agtcatcgct attaccatag tgatgcggtt ttggcagtac atcaatgggc     420
gtggatagcg gtttgactca cggggatttc caagtctcca ccccattgac gtcaatggga     480
gtttgttttg gcaccaaaat caacgggact ttccaaaatg tcgtaacaac tccgccccat     540
tgacgcaaat gggcggtagg cgtgtacggt gggaggtcta taagcaga gctttctggc       600 taactagaga acccactgct tactggcacg tggaaattaa tacgacgtgg ccaccatggg     660
atggagctgt atcatcctct tcttggtagc aacagctaca ggtaagggt taacagtagc      720 aggcttgagt tctggacata tatgggtg acaatgacat ccactttgcc tttctctcca       780
caggcgcgca ctccgaagtg aagcttgagg agtctggagg aggcttggtg caacctggac     840
gatccatgaa actctcctgt gttgcctctg gattcacttt cagtaactac tggatgaact     900
gggtccgcca gtctccagag aaggggcttg agtgggttgc tgagattaga ttgaaatcta    960
ataattatgc aacacattat gcggagtctg tgaaagggag gttcaccatc tcaagagatg    1020
attccaaaag tagtgtctac ctgcaaatga acaacttaag agctgaagac actggcattt    1080
attactgtac cttcggtaat agctttgctt actgggggcca aggactctg gtcactgtct    1140 ctgcagctag caccaagggc ccatcggtct tcccctggc accctcctcc aagagcacct    1200 ctggggggcac agcggccctg ggctgcctgg tcaaggacta cttccccgaa ccggtgacgg    1260
tgtcgtggaa ctcaggcgcc ctgaccagcg gcgtgcacac cttcccggct gtcctacagt    1320
cctcaggact ctactccctc agcagcgtgg tgaccgtgcc ctccagcagc ttgggcaccc    1380
agacctacat ctgcaacgtg aatcacaagc ccagcaacac caaggtggac aagagagttg    1440
agcccaaatc ttgtgacaaa actcacacat gcccaccgtg cccagcacct gaactcctgg    1500
ggggaccgtc agtcttcctc ttccccccaa aacccaagga caccctcatg atctcccgga    1560
cccctgaggt cacatgcgtg gtggtggacg tgagccacga agaccctgag gtcaagttca    1620
actggtacgt ggacggcgtg gaggtgcata atgccaagac aaagccgcgg gaggagcagt    1680
acaacagcac gtaccgtgtg gtcagcgtcc tcaccgtcct gcaccaggac tggctgaatg    1740
gcaaggagta caagtgcaag gtctccaaca aagccctccc agcccccatc gagaaaacca    1800
tctccaaagc caaagggcag ccccgagaac cacaggtgta caccctgccc ccatcccggg    1860
```

```
aggagatgac caagaaccag gtcagcctga cctgcctggt caaaggcttc tatcccagcg   1920
acatcgccgt ggagtgggag agcaatgggc agccggagaa caactacaag accacgcctc   1980
ccgtgctgga ctccgacggc tccttcttcc tctatagcaa gctcaccgtg gacaagagca   2040
ggtggcagca ggggaacgtc ttctcatgct ccgtgatgca tgaggctctg cacaaccact   2100
acacgcagaa gagcctctcc ctgtccccgg gtaaatgatc tagaagctcg ctgatcagcc   2160
tcgactgtgc cttctagttg ccagccatct gttgtttgcc cctccccgt gccttccttg    2220 accctggaag gtgccactcc cactgtcctt tcctaataaa atgaggaaat tgcatcgcat   2280
tgtctgagta ggtgtcattc tattctgggg ggtggggtgg ggcaggacag caaggggag    2340 gattgggaag acaatagcag gcatgctggg gatggcccgg gctctatggc ttctgaggcg   2400
gaaagaacca gctgggctc tagggggtat ccccacgcgc cctgtagcgg cgcattaagc    2460
gcggcgggtg tggtggttac gcgcagcgtg accgctacac ttgccagcgc cctagcgccc   2520
gctcctttcg ctttcttccc ttcctttctc gccacgttcg ccggctttcc ccgtcaagct   2580
ctaaatcggg ggctcccttt agggttccga tttagtgctt tacggcacct ctcccccaaa   2640
aaacttgatt agggtgatgg ttcacgtagt gggccatcgc cctgatagac ggttttcgc    2700 cctttgacgt tggagtccac gttctttaat agtggactct tgttccaaac tggaacaaca   2760 ctcaaccta tctcggtcta ttctttttgat ttataaggga ttttgccgat ttcggcctat   2820
tggttaaaaa atgagctgat ttaacaaaaa tttaacgcga attaattctg tggaatgtgt   2880
gtcagttagg gtgtggaaag tccccaggct ccccagcagg cagaagtatg caaagcatgc   2940
atctcaatta gtcagcaacc aggtgtggaa agtccccagg ctccccagca ggcagaagta   3000
tgcaaagcat gcatctcaat tagtcagcaa ccatagtccc gcccctaact ccgcccatcc   3060
cgcccctaac tccgcccagt tccgcccatt ctccgcccct aggctgacta attttttta    3120 tttatgcaga ggccgaggcc gcctctgcct ctgagctatt ccagaagtag tgaggaggct   3180 ttttggagg cctaggcttt tgcaaaaagc tcccccccg ggaggtccac aatggttgaa     3240
caagatggat tgcacgcagg ttctccggcc gcttgggtgg agaggctatt cggctatgac   3300
tgggcacaac agacaatcgg ctgctctgat gccgccgtgt tccggctgtc agcgcagggg   3360
cgcccggttc ttttttgtcaa gaccgacctg tccggtgccc tgaatgaact ccaggacgag   3420
gcagcgcggc tatcgtggct ggccacgacg gcgttccttg cgcagctgt gctcgacgtt    3480 gtcactgaag cggaaggga ctggctgcta ttgggcgaag tgccggggca ggatctcctg    3540
tcatctcacc ttgctcctgc cgagaaagta tccatcatgg ctgatgcaat gcggcggctg   3600
catacgcttg atccggctac ctgcccattc gaccaccaag cgaaacatcg catcgagcga   3660
gcacgtactc ggatggaagc cggtcttgtc gatcaggatg atctggacga agagcatcag   3720
gggctcgcgc cagccgaact gttcgccagg ctcaaggcgc gtatgcccga cggcgaggat   3780
ctcgtcgtga ctcatggcga tgcctgcttg ccgaatatca tggtggaaaa tggccgcttt   3840
tctggattca tcgactgtgg ccggctgggt gtggcggacc gctatcagga catagcgttg   3900
gctacccgtg atattgctga agagcttggc ggcgaatggg ctgaccgctt cctcgtgctt   3960
tacggtatcg ccgctcccga ttcgcagcgc atcgccttct atcgccttct tgacgagttc   4020
ttctgagcgg gactctgggg ttcgaaatga ccgaccaagc gacgcccaac ctgccatcac   4080
gagatttcga ttccaccgcc gccttctatg aaaggttggg cttcggaatc gttttccggg   4140
acgccggctg gatgatcctc cagcgcgggg atctcatgct ggagttcttc gcccacccca   4200
acttgtttat tgcagcttat aatggttaca ataaagcaa tagcatcaca aatttcacaa    4260
```

```
ataaagcatt tttttcactg cattctagtt gtggtttgtc caaactcatc aatgtatctt    4320
atcatgtctg tataccgtcg atctttccgc ttcctcgctc actgactcgc tgcgctcggt    4380
cgttcggctg cggcgagcgg tatcagctca ctcaaaggcg gtaatacggt tatccacaga    4440 atcagggga t aacgcaggaa agaacatgtg agcaaaaggc cagcaaaagg ccaggaaccg    4500
taaaaaggcc gcgttgctgg cgttttttcca taggctccgc cccccctgacg agcatcacaa    4560 aaatcgacgc tcaagtcaga ggtggcgaaa cccgacagga ctataaagat accaggcgtt    4620
tccccctgga agctccctcg tgcgctctcc tgttccgacc ctgccgctta ccggatacct    4680
gtccgccttt ctcccttcgg gaagcgtggc gctttctcat agctcacgct gtaggtatct    4740
cagttcggtg taggtcgttc gctccaagct gggctgtatg cacgaacccc ccgttcagcc    4800
cgaccgctgc gccttatccg gtaactatcg tcttgagtcc aacccggtaa gacacgactt    4860
atcgccactg gcagcagcca ctggtaacag gattagcaga gcgaggtatg taggcggtgc    4920
tacagagttc ttgaagtggt ggcctaacta cggctacact agaagaacag tatttggtat    4980
ctgcgctctg ctgaagccag ttaccttcgg aaaaagagtt ggtagctctt gatccggcaa    5040
acaaaccacc gctggtagcg gtggtttttt tgtttgcaag cagcagatta cgcgcagaaa    5100
aaaaggatct caagaagatc ctttgatctt ttctacgggg tctgacgctc agtggaacga    5160
aaactcacgt taagggattt tggtcatgag attatcaaaa aggatcttca cctagatcct    5220
tttaaattaa aaatgaagtt ttaaatcaat ctaaagtata tatgagtaaa cttggtctga    5280
cagttaccaa tgcttaatca gtgaggcacc tatctcagcg atctgtctat ttcgttcatc    5340
catagttgcc tgactccccg tcgtgtagat aactacgata cgggagggct taccatctgg    5400
ccccagtgct gcaatgatac cgcgagaccc acgctcaccg gctccagatt tatcagcaat    5460
aaaccagcca gccggaaggg ccgagcgcag aagtggtcct gcaactttat ccgcctccat    5520
ccagtctatt aattgttgcc gggaagctag agtaagtagt tcgccagtta atagtttgcg    5580
caacgttgtt gccattgcta caggcatcgt ggtgtcacgc tcgtcgtttg gtatggcttc    5640
attcagctcc ggttcccaac gatcaaggcg agttacatga tcccccatgt tgtgcaaaaa    5700
agcggttagc tccttcggtc ctccgatcgt tgtcagaagt aagttggccg cagtgttatc    5760
actcatggtt atggcagcac tgcataattc tcttactgtc atgccatccg taagatgctt    5820
ttctgtgact ggtgagtact caaccaagtc attctgagaa tagtgtatgc ggcgaccgag    5880
ttgctcttgc ccggcgtcaa tacgggataa taccgcgcca catagcagaa ctttaaaagt    5940
gctcatcatt ggaaaacgtt cttcggggcg aaaactctca aggatcttac cgctgttgag    6000
atccagttcg atgtaaccca ctcgggcacc caactgatct tcagcatctt ttactttcac    6060
cagcgtttct gggtgagcaa aaacaggaag gcaaaatgcc gcaaaaaagg gaataagggc    6120
gacacggaaa tgttgaatac tcatactctt ccttttttcaa tattattgaa gcatttatca    6180
gggttattgt ctcatgagcg gatacatatt tgaatgtatt tagaaaaata aacaaatagg    6240
ggttccgcgc acatttcccc gaaaagtgcc acctgacgtc agatcgacgg atcgggagat    6300
cg                                                                  6302
```

<210> SEQ ID NO 8
<211> LENGTH: 6076
<212> TYPE: DNA
<213> ORGANISM: Artificial Sequence
<220> FEATURE:
<223> OTHER INFORMATION: Synthetic

<400> SEQUENCE: 8

```
gtaccgaatt cacattgatt attgagtagt tattaatagt aatcaattac ggggtcatta     60
gttcatagcc catatatgga gttccgcgtt acataactta cggtaaatgg cccgcctggc    120
tgaccgccca acgaccccg cccattgacg tcaataatga cgtatgttcc catagtaacg    180
ccaataggga ctttccattg acgtcaatgg gtggagtatt tacggtaaac tgcccacttg    240
gcagtacatc aagtgtatca tatgccaagt acgccccta ttgacgtcaa tgacggtaaa    300
tggcccgcct ggcattatgc ccagtacatg accttatggg actttcctac ttggcagtac    360
atctacggtt agtcatcgct attaccatag tgatgcggtt ttggcagtac atcaatgggc    420
gtggatagcg gtttgactca cggggatttc caagtctcca ccccattgac gtcaatggga    480
gtttgttttg gcaccaaaat caacgggact ttccaaaatg tcgtaacaac tccgccccat    540
tgacgcaaat gggcggtagg cgtgtacggt gggaggtcta tataagcaga gctttctggc    600
taactagaga acccactgct tactggcacg tggaaattaa tacgacgtgg ccaccatggg    660
atggagctgt atcatcctct tcttggtagc aacagctaca ggtaagggt taacagtagc    720 aggcttgagg tctggacata tatgggtg acaatgacat ccactttgcc tttctctcca    780
caggcgcgca ctccgaaatg gttctcaccc agtctccagt atccataact gcatctcgag    840
gggagaaggt caccatcacc tgccgtgcca gctcaagtat aagttccaat tacttacact    900
ggtaccagca gaagccagga tcctcccta aactttgat ttataggaca tccatcctgg    960
catctggagt cctagacagc ttcagtggca gtgggtctga gagctcttac actctgacaa   1020
tcagctgcat gcaggacgaa gttgctgcca cttactattg tcaacagggg agtagtagcc   1080
cacccacgtt cggtgctggg accaagctgg agctgaaacg tacggtggct gcaccatctg   1140
tcttcatctt cccgccatct gatgagcagt tgaaatctgg aactgcctct gttgtgtgcc   1200
tgctgaataa cttctatccc agagaggcca agtacagtg gaaggtggat aacgccctcc   1260
aatcgggtaa ctcccaggag agtgtcacag agcaggacag caaggacagc acctacagcc   1320
tcagcagcac cctgacgctg agcaaagcag actacgagaa acacaaagtc tacgcctgcg   1380
aagtcaccca tcagggcctg agctcgcccg tcacaaagag cttcaacagg ggagagtgtt   1440
aataatctag agggcccgtt ttttaaaccg ctgatcagcc tcgactgtgc cttctagttg   1500
ccagccatct gttgtttgcc cctcccccgt gccttccttg accctggaag gtgccactcc   1560
cactgtcctt tcctaataaa atgaggaaat tgcatcgcat tgtctgagta ggtgtcattc   1620
tattctgggg ggtggggtgg ggcaggacag caagggggag gattgggaag acaatagcag   1680
gcatgctggg gatgcggtgg gctctatggc ttctgaggcg gaaagaacca gctggggctc   1740 taggggggtat cccacgcgc cctgtagcgg cgcattaagc gcggcgggtg tggtggttac   1800
gcgcagcgtg accgctacac ttgccagcgc cctagcgccc gctcctttcg ctttcttccc   1860
ttcctttctc gccacgttcg ccggctttcc ccgtcaagct ctaaatcggg gctccctt    1920 agggttccga tttagtgctt tacggcacct cgaccccaaa aaacttgatt agggtgatgg   1980
ttcacgtagt gggccatcgc cctgatagac ggttttcgc cctttgacgt tggagtccac   2040
gttctttaat agtggactct tgttccaaac tggaacaaca ctcaaccta tctcggtcta   2100 ttcttttgat ttataaggga ttttggccat tcggcctat tggttaaaaa atgagctgat   2160
ttaacaaaaa tttaacgcga attaattctg tggaatgtgt gtcagttagg gtgtggaaag   2220
tccccaggct ccccagcagg cagaagtatg caaagcatgc atctcaatta gtcagcaacc   2280
aggtgtggaa agtccccagg ctccccagca ggcagaagta tgcaaagcat gcatctcaat   2340
tagtcagcaa ccatagtccc gcccctaact ccgcccatcc cgcccctaac tccgcccagt   2400
```

```
tccgcccatt ctccgcccca tggctgacta attttttta tttatgcaga ggccgaggcc    2460
gcctctgcct ctgagctatt ccagaagtag tgaggaggct tttttggagg cctaggcttt    2520
tgcaaaaagc tcccgggagc ttgtatatcc attttcggat ctgatcagca cgtgatgaaa    2580
aagcctgaac tcaccgcgac gtctgtcgag aagtttctga tcgaaaagtt cgacagcgtc    2640
tccgacctga tgcagctctc ggagggcgaa gaatctcgtg ctttcagctt cgatgtagga    2700
gggcgtggat atgtcctgcg ggtaaatagc tgcgccgatg gtttctacaa agatcgttat    2760
gtttatcggc actttgcatc ggccgcgctc ccgattccgg aagtgcttga cattggggaa    2820
ttcagcgaga gcctgaccta ttgcatctcc cgccgtgcac agggtgtcac gttgcaagac    2880
ctgcctgaaa ccgaactgcc cgctgttctg cagccggtcg cggaggccat ggatgcgatc    2940
gctgcggccg atcttagcca gacgagcggg ttcggcccat tcggaccgca aggaatcggt    3000
caatacacta catggcgtga tttcatatgc gcgattgctg atcccatgt gtatcactgg     3060 caaactgtga tggacgacac cgtcagtgcg tccgtcgcgc aggctctcga tgagctgatg    3120 cttttgggccg aggactgccc cgaagtccgg cacctcgtgc acgcggattt cggctccaac   3180
aatgtcctga cggacaatgg ccgcataaca gcggtcattg actggagcga ggcgatgttc    3240
ggggattccc aatacgaggt cgccaacatc ttcttctgga ggccgtggtt ggcttgtatg    3300
gagcagcaga cgcgctactt cgagcggagg catccggagc ttgcaggatc gccgcggctc    3360
cgggcgtata tgctccgcat tggtcttgac caactctatc agagcttggt tgacggcaat    3420
ttcgatgatg cagcttgggc gcagggtcga tgcgacgcaa tcgtccgatc cggagccggg    3480
actgtcgggc gtacacaaat cgcccgcaga agcgcggccg tctggaccga tggctgtgta    3540
gaagtactcg ccgatagtgg aaaccgacgc cccagcactc gtccgagggc aaaggaatag    3600
cacgtgctac gagatttcga ttccaccgcc gccttctatg aaaggttggg cttcggaatc    3660
gttttccggg acgccggctg gatgatcctc cagcgcgggg atctcatgct ggagttcttc    3720
gcccacccca acttgtttat tgcagcttat aatggttaca aataaagcaa tagcatcaca    3780
aatttcacaa ataaagcatt tttttcactg cattctagtt gtggtttgtc caaactcatc    3840
aatgtatctt atcatgtctg tataccgtcg acctctagct agagcttggc gtaatcatgg    3900
tcatagctgt ttcctgtgtg aaattgttat ccgctcacaa ttccacacaa catacgagcc    3960
ggaagcataa agtgtaaagc ctggggtgcc taatgagtga gctaactcac attaattgcg    4020
ttgcgctcac tgcccgcttt ccagtcggga aacctgtcgt gccagctgca ttaatgaatc    4080
ggccaacgcg cggggagagg cggtttgcgt attgggcgct cttccgcttc ctcgctcact    4140
gactcgctgc gctcggtcgt tcggctgcgg cgagcggtat cagctcactc aaaggcggta    4200
atacggttat ccacagaatc aggggataac gcaggaaaga acatgtgagc aaaaggccag    4260
caaaaggcca ggaaccgtaa aaaggccgcg ttgctggcgt ttttccatag gctccgcccc    4320
cctgacgagc atcacaaaaa tcgacgctca agtcagaggt ggcgaaaccc gacaggacta    4380
taaagatacc aggcgtttcc ccctggaagc tccctcgtgc gctctcctgt tccgaccctg    4440
ccgcttaccg gatacctgtc cgcctttctc ccttcgggaa gcgtggcgct ttctcatagc    4500
tcacgctgta ggtatctcag ttcggtgtag gtcgttcgct ccaagctggg ctgtgtgcac    4560
gaaccccccg ttcagcccga ccgctgcgcc ttatccggta actatcgtct tgagtccaac    4620
ccggtaagac acgacttatc gccactggca gcagccactg gtaacaggat tagcagagcg    4680
aggtatgtag gcggtgctac agagttcttg aagtggtggc ctaactacgg ctacactaga    4740
agaacagtat ttggtatctg cgctctgctg aagccagtta ccttcggaaa aagagttggt    4800
```

```
agctcttgat ccggcaaaca aaccaccgct ggtagcggtt ttttgtttg caagcagcag      4860 attacgcgca gaaaaaaagg atctcaagaa gatcctttga tcttttctac ggggtctgac      4920
gctcagtgga acgaaaactc acgttaaggg attttggtca tgagattatc aaaaaggatc      4980
ttcacctaga tccttttaaa ttaaaaatga agttttaaat caatctaaag tatatatgag      5040
taaacttggt ctgacagtta ccaatgctta atcagtgagg cacctatctc agcgatctgt      5100
ctatttcgtt catccatagt tgcctgactc cccgtcgtgt agataactac gatacgggag      5160
ggcttaccat ctggccccag tgctgcaatg ataccgcgag acccacgctc accggctcca      5220
gatttatcag caataaacca gccagccgga agggccgagc gcagaagtgg tcctgcaact      5280
ttatccgcct ccatccagtc tattaattgt tgccgggaag ctagagtaag tagttcgcca      5340
gttaatagtt tgcgcaacgt tgttgccatt gctacaggca tcgtggtgtc acgctcgtcg      5400
tttggtatgg cttcattcag ctccggttcc caacgatcaa ggcgagttac atgatccccc      5460
atgttgtgca aaaaagcggt tagctccttc ggtcctccga tcgttgtcag aagtaagttg      5520
gccgcagtgt tatcactcat ggttatggca gcactgcata attctcttac tgtcatgcca      5580
tccgtaagat gcttttctgt gactggtgag tactcaacca agtcattctg agaatagtgt      5640
atgcggcgac cgagttgctc ttgcccggcg tcaatacggg ataataccgc gccacatagc      5700
agaactttaa aagtgctcat cattggaaaa cgttcttcgg ggcgaaaact ctcaaggatc      5760
ttaccgctgt tgagatccag ttcgatgtaa cccactcgtg cacccaactg atcttcagca      5820
tcttttactt tcaccagcgt ttctgggtga gcaaaaacag gaaggcaaaa tgccgcaaaa      5880
aagggaataa gggcgacacg gaaatgttga atactcatac tcttcctttt tcaatattat      5940
tgaagcattt atcagggtta ttgtctcatg agcggataca tatttgaatg tatttagaaa      6000
aataaacaaa taggggttcc gcgcacattt ccccgaaaag tgccacctga cgtcagatcg      6060
acggatcggg agatcg                                                      6076

<210> SEQ ID NO 9
<211> LENGTH: 6308
<212> TYPE: DNA
<213> ORGANISM: Artificial Sequence
<220> FEATURE:
<223> OTHER INFORMATION: Synthetic

<400> SEQUENCE: 9
gtaccgaatt cacattgatt attgagtagt tattaatagt aatcaattac ggggtcatta       60
gttcatagcc catatatgga gttccgcgtt acataactta cggtaaatgg cccgcctggc      120
tgaccgccca acgaccccg cccattgacg tcaataatga cgtatgttcc catagtaacg      180
ccaataggga ctttccattg acgtcaatgg gtggagtatt tacggtaaac tgcccacttg      240
gcagtacatc aagtgtatca tatgccaagt acgccccta ttgacgtcaa tgacggtaaa      300
tggcccgcct ggcattatgc ccagtacatg accttatggg actttcctac ttggcagtac      360
atctacggtt agtcatcgct attaccatag tgatgcggtt ttggcagtac atcaatgggc      420
gtggatagcg gtttgactca cggggatttc caagtctcca ccccattgac gtcaatggga      480
gtttgttttg gcaccaaaat caacgggact ttccaaaatg tcgtaacaac tccgccccat      540
tgacgcaaat gggcggtagg cgtgtacggt gggaggtcta taagcagag ctttctggc      600 taactagaga acccactgct tactggcacg tggaaattaa tacgacgtgg ccaccatggg      660
atggagctgt atcatcctct tcttggtagc aacagctaca ggtaagggt taacagtagc      720 aggcttgagg tctggacata tatatgggtg acaatgacat ccactttgcc tttctctcca      780
```

```
caggcgcgca ctcccaggta caactgcagc agtctggacc tgaactgaag aagcctggag      840
agacagtcaa gatctcctgc aaggcctctg gtatcctttt cacaaactat ggaatgaact      900
gggtgaagca ggctccagga cagggtttaa agtggatggg ctggattaac acctccactg      960
gagagtcaac atttgctgat gacttcaagg gacggtttga cttctctttg gaaacctctg     1020
ccaacactgc ctatttgcag atcaacaacc tcaaaagtga agacatggct acatatttct     1080
gtgcaagatg ggaggtttac cacggctacg ttccttactg gggccaaggg accacggtca     1140
ccgtttcctc tgctagcacc aagggcccat cggtcttccc cctggcaccc tcctccaaga     1200
gcacctctgg gggcacagcg gccctgggct gcctggtcaa ggactacttc cccgaaccgg     1260
tgacggtgtc gtggaactca ggcgccctga ccagcggcgt gcacaccttc ccggctgtcc     1320
tacagtcctc aggactctac tccctcagca gcgtggtgac cgtgccctcc agcagcttgg     1380
gcacccagac ctacatctgc aacgtgaatc acaagcccag caacaccaag gtggacaaga     1440
gagttgagcc caaatcttgt gacaaaactc acacatgccc accgtgccca gcacctgaac     1500
tcctgggggg accgtcagtc ttcctcttcc ccccaaaacc caaggacacc ctcatgatct     1560
cccggacccc tgaggtcaca tgcgtggtgg tggacgtgag ccacgaagac cctgaggtca     1620
agttcaactg gtacgtggac ggcgtggagg tgcataatgc caagacaaag ccgcgggagg     1680
agcagtacaa cagcacgtac cgtgtggtca gcgtcctcac cgtcctgcac caggactggc     1740
tgaatggcaa ggagtacaag tgcaaggtct ccaacaaagc cctcccagcc cccatcgaga     1800
aaaccatctc caaagccaaa gggcagcccc gagaaccaca ggtgtacacc ctgcccccat     1860
cccgggagga gatgaccaag aaccaggtca gcctgacctg cctggtcaaa ggcttctatc     1920
ccagcgacat cgccgtggag tgggagagca atgggcagcc ggagaacaac tacaagacca     1980
cgcctcccgt gctggactcc gacggctcct tcttcctcta tagcaagctc accgtggaca     2040
agagcaggtg gcagcagggg aacgtcttct catgctccgt gatgcatgag gctctgcaca     2100
accactacac gcagaagagc ctctccctgt ccccgggtaa atgatctaga agctcgctga     2160
tcagcctcga ctgtgccttc tagttgccag ccatctgttg tttgcccctc cccgtgcct      2220 tccttgaccc tggaaggtgc cactcccact gtcctttcct aataaaatga ggaaattgca     2280
tcgcattgtc tgagtaggtg tcattctatt ctggggggtg gggtggggca ggacagcaag     2340
ggggaggatt gggaagacaa tagcaggcat gctggggatg gccgggctc tatggcttct      2400 gaggcggaaa gaaccagctg gggctctagg gggtatcccc acgcgccctg tagcggcgca     2460
ttaagcgcgg cgggtgtggt ggttacgcgc agcgtgaccg ctacacttgc cagcgcccta     2520
gcgcccgctc ctttcgcttt cttcccttcc tttctcgcca cgttcgccgg ctttccccgt     2580
caagctctaa atcgggggct ccctttaggg ttccgattta gtgctttacg gcacctctcc     2640
cccaaaaaac ttgattaggg tgatggttca cgtagtgggc catcgccctg atagacggtt     2700
tttcgccctt tgacgttgga gtccacgttc tttaatagtg gactcttgtt ccaaactgga     2760
acaacactca accctatctc ggtctattct tttgatttat aagggatttt gccgatttcg     2820
gcctattggt taaaaaatga gctgatttaa caaaaattta cgcgaatta attctgtgga      2880 atgtgtgtca gttagggtgt ggaaagtccc caggctcccc agcaggcaga agtatgcaaa     2940
gcatgcatct caattagtca gcaaccaggt gtggaaagtc cccaggctcc ccagcaggca     3000
gaagtatgca aagcatgcat ctcaattagt cagcaaccat agtcccgccc ctaactccgc     3060
ccatcccgcc cctaactccg cccagttccg cccattctcc gccccaggc tgactaattt       3120 tttttatttta tgcagaggcc gaggccgcct ctgcctctga gctattccag aagtagtgag     3180
```

```
gaggcttttt tggaggccta ggcttttgca aaaagctccc cccccgggag gtccacaatg   3240
gttgaacaag atggattgca cgcaggttct ccggccgctt gggtggagag gctattcggc   3300
tatgactggg cacaacagac aatcggctgc tctgatgccg ccgtgttccg gctgtcagcg   3360
caggggcgcc cggttctttt tgtcaagacc gacctgtccg gtgccctgaa tgaactccag   3420
gacgaggcag cgcggctatc gtggctggcc acgacgggcg ttccttgcgc agctgtgctc   3480
gacgttgtca ctgaagcggg aagggactgg ctgctattgg gcgaagtgcc ggggcaggat   3540
ctcctgtcat ctcaccttgc tcctgccgag aaagtatcca tcatggctga tgcaatgcgg   3600
cggctgcata cgcttgatcc ggctacctgc ccattcgacc accaagcgaa acatcgcatc   3660
gagcgagcac gtactcggat ggaagccggt cttgtcgatc aggatgatct ggacgaagag   3720 catcagggc tcgcgccagc cgaactgttc gccaggctca aggcgcgtat gcccgacggc   3780
gaggatctcg tcgtgactca tggcgatgcc tgcttgccga atatcatggt ggaaaatggc   3840
cgcttttctg gattcatcga ctgtggccgg ctgggtgtgg cggaccgcta tcaggacata   3900
gcgttggcta cccgtgatat tgctgaagag cttggcggcg aatgggctga ccgcttcctc   3960
gtgctttacg gtatcgccgc tcccgattcg cagcgcatcg ccttctatcg ccttcttgac   4020
gagttcttct gagcgggact ctggggttcg aaatgaccga ccaagcgacg cccaacctgc   4080
catcacgaga tttcgattcc accgccgcct tctatgaaag gttgggcttc ggaatcgttt   4140
tccgggacgc cggctggatg atcctccagc gcggggatct catgctggag ttcttcgccc   4200
accccaactt gtttattgca gcttataatg gttacaaata aagcaatagc atcacaaatt   4260
tcacaaataa agcatttttt tcactgcatt ctagttgtgg tttgtccaaa ctcatcaatg   4320
tatcttatca tgtctgtata ccgtcgatct ttccgcttcc tcgctcactg actcgctgcg   4380
ctcggtcgtt cggctgcggc gagcggtatc agctcactca aaggcggtaa tacggttatc   4440
cacagaatca ggggataacg caggaaagaa catgtgagca aaaggccagc aaaaggccag   4500
gaaccgtaaa aaggccgcgt tgctggcgtt tttccatagg ctccgccccc ctgacgagca   4560
tcacaaaaat cgacgctcaa gtcagaggtg gcgaaacccg acaggactat aaagatacca   4620
ggcgtttccc cctggaagct ccctcgtgcg ctctcctgtt ccgaccctgc cgcttaccgg   4680
atacctgtcc gcctttctcc cttcgggaag cgtggcgctt tctcatagct cacgctgtag   4740
gtatctcagt tcggtgtagg tcgttcgctc caagctgggc tgtatgcacg aaccccccgt   4800
tcagcccgac cgctgcgcct tatccggtaa ctatcgtctt gagtccaacc cggtaagaca   4860
cgacttatcg ccactggcag cagccactgg taacaggatt agcagagcga ggtatgtagg   4920
cggtgctaca gagttcttga agtggtggcc taactacggc tacactagaa gaacagtatt   4980
tggtatctgc gctctgctga agccagttac cttcggaaaa agagttggta gctcttgatc   5040
cggcaaacaa accaccgctg gtagcggtgg tttttttgtt tgcaagcagc agattacgcg   5100
cagaaaaaaa ggatctcaag aagatccttt gatcttttct acggggtctg acgctcagtg   5160
gaacgaaaac tcacgttaag ggattttggt catgagatta tcaaaaagga tcttcaccta   5220
gatcctttta aattaaaaat gaagttttaa atcaatctaa agtatatatg agtaaacttg   5280
gtctgacagt taccaatgct taatcagtga ggcacctatc tcagcgatct gtctatttcg   5340
ttcatccata gttgcctgac tccccgtcgt gtagataact acgatacggg agggcttacc   5400
atctggcccc agtgctgcaa tgataccgcg agacccacgc tcaccggctc cagatttatc   5460
agcaataaac cagccagccg gaagggccga gcgcagaagt ggtcctgcaa ctttatccgc   5520
ctccatccag tctattaatt gttgccggga agctagagta agtagttcgc cagttaatag   5580
```

```
tttgcgcaac gttgttgcca ttgctacagg catcgtggtg tcacgctcgt cgtttggtat    5640
ggcttcattc agctccggtt cccaacgatc aaggcgagtt acatgatccc ccatgttgtg    5700
caaaaaagcg gttagctcct tcggtcctcc gatcgttgtc agaagtaagt tggccgcagt    5760
gttatcactc atggttatgg cagcactgca taattctctt actgtcatgc catccgtaag    5820
atgcttttct gtgactggtg agtactcaac caagtcattc tgagaatagt gtatgcggcg    5880
accgagttgc tcttgcccgg cgtcaatacg ggataatacc gcgccacata gcagaacttt    5940
aaaagtgctc atcattggaa aacgttcttc ggggcgaaaa ctctcaagga tcttaccgct    6000
gttgagatcc agttcgatgt aacccactcg gcacccaac tgatcttcag catcttttac     6060
tttcaccagc gtttctgggt gagcaaaaac aggaaggcaa aatgccgcaa aaagggaat     6120 aagggcgaca cggaaatgtt gaatactcat actcttcctt tttcaatatt attgaagcat    6180
ttatcagggt tattgtctca tgagcggata catatttgaa tgtatttaga aaaataaaca    6240
aataggggtt ccgcgcacat ttccccgaaa agtgccacct gacgtcagat cgacggatcg    6300
ggagatcg                                                             6308
```

<210> SEQ ID NO 10
<211> LENGTH: 6073
<212> TYPE: DNA
<213> ORGANISM: Artificial Sequence
<220> FEATURE:
<223> OTHER INFORMATION: Synthetic

<400> SEQUENCE: 10

```
gtaccgaatt cacattgatt attgagtagt tattaatagt aatcaattac ggggtcatta      60
gttcatagcc catatatgga gttccgcgtt acataactta cggtaaatgg cccgcctggc     120
tgaccgccca acgaccccg cccattgacg tcaataatga cgtatgttcc catagtaacg      180
ccaatagggg ctttccattg acgtcaatgg gtggagtatt tacggtaaac tgcccacttg     240
gcagtacatc aagtgtatca tatgccaagt acgcccccta ttgacgtcaa tgacggtaaa     300
tggcccgcct ggcattatgc ccagtacatg accttatggg actttcctac ttggcagtac     360
atctacggtt agtcatcgct attaccatag tgatgcggtt ttggcagtac atcaatgggc     420
gtggatagcg gtttgactca cggggatttc caagtctcca ccccattgac gtcaatggga     480
gtttgttttg gcaccaaaat caacgggact ttccaaaatg tcgtaacaac tccgccccat     540
tgacgcaaat gggcggtagg cgtgtacggt gggaggtcta taagcaga gctttctggc       600 taactagaga acccactgct tactggcacg tggaaattaa tacgacgtgg ccaccatggg     660
atggagctgt atcatcctct tcttggtagc aacagctaca ggtaaggggt taacagtagc     720
aggcttgagg tctggacata tatgggtg acaatgacat ccactttgcc tttctctcca      780
caggcgcgca ctccgacatc cagctgaccc agtctcacaa attcctgtcc acttcagtag    840
gagacagggt cagcatcacc tgcaaggcca gtcaggatgt gtataatgct gttgcctggt     900
atcaacagaa accaggacaa tctcctaaac ttctgattta ctcggcatcc tcccggtaca     960
ctggagtccc ttctcgcttc actggcagtg gctctgggcc ggatttcact ttcaccatca    1020
gcagtgtgca ggctgaagac ctggcagttt atttctgtca gcaacatttt cgtactccat    1080
tcacgttcgg ctcggggaca aaattggaga tcaaacgtac ggtggctgca ccatctgtct    1140
tcatcttccc gccatctgat gagcagttga aatctggaac tgcctctgtt gtgtgcctgc    1200
tgaataactt ctatcccaga gaggccaaag tacagtggaa ggtggataac gccctccaat    1260
cgggtaactc ccaggagagt gtcacagagc aggacagcaa ggacagcacc tacagcctca    1320
```

```
gcagcaccct gacgctgagc aaagcagact acgagaaaca caaagtctac gcctgcgaag    1380
tcacccatca gggcctgagc tcgcccgtca caaagagctt caacagggga gagtgttaat    1440
aatctagagg gcccgttttt taaaccgctg atcagcctcg actgtgcctt ctagttgcca    1500
gccatctgtt gtttgcccct cccccgtgcc ttccttgacc ctggaaggtg ccactcccac    1560
tgtcctttcc taataaaatg aggaaattgc atcgcattgt ctgagtaggt gtcattctat    1620
tctggggggt ggggtggggc aggacagcaa ggggggaggat tgggaagaca atagcaggca    1680
tgctggggat gcggtgggct ctatggcttc tgaggcggaa agaaccagct ggggctctag    1740
ggggtatccc cacgcgccct gtagcggcgc attaagcgcg gcgggtgtgg tggttacgcg    1800
cagcgtgacc gctacacttg ccagcgccct agcgcccgct cctttcgctt tcttcccttc    1860
ctttctcgcc acgttcgccg gctttccccg tcaagctcta aatcggggc tcccttagg    1920 gttccgattt agtgctttac ggcacctcga ccccaaaaaa cttgattagg gtgatggttc    1980
acgtagtggg ccatcgccct gatagacggt ttttcgccct ttgacgttgg agtccacgtt    2040
ctttaatagt ggactcttgt tccaaactgg aacaacactc aaccctatct cggtctattc    2100
ttttgattta aagggatttt tggccatttc ggcctattgg ttaaaaaatg agctgattta    2160
acaaaaattt aacgcgaatt aattctgtgg aatgtgtgtc agttagggtg tggaaagtcc    2220
ccaggctccc cagcaggcag aagtatgcaa agcatgcatc tcaattagtc agcaaccagg    2280
tgtggaaagt ccccaggctc cccagcaggc agaagtatgc aaagcatgca tctcaattag    2340
tcagcaacca tagtcccgcc cctaactccg cccatcccgc ccctaactcc gcccagttcc    2400
gcccattctc cgccccatgg ctgactaatt ttttttattt atgcagaggc cgaggccgcc    2460
tctgcctctg agctattcca gaagtagtga ggaggctttt ttggaggcct aggcttttgc    2520
aaaaagctcc cgggagcttg tatatccatt ttcggatctg atcagcacgt gatgaaaaag    2580
cctgaactca ccgcgacgtc tgtcgagaag tttctgatcg aaaagttcga cagcgtctcc    2640
gacctgatgc agctctcgga gggcgaagaa tctcgtgctt tcagcttcga tgtaggaggg    2700
cgtggatatg tcctgcgggt aaatagctgc gccgatggtt tctacaaaga tcgttatgtt    2760
tatcggcact ttgcatcggc cgcgctcccg attccggaag tgcttgacat tggggaattc    2820
agcgagagcc tgacctattg catctcccgc cgtgcacagg gtgtcacgtt gcaagacctg    2880
cctgaaaccg aactgcccgc tgttctgcag ccggtcgcgg aggccatgga tgcgatcgct    2940
gcggccgatc ttagccagac gagcgggttc ggcccattcg gaccgcaagg aatcggtcaa    3000
tacactacat ggcgtgattt catatgcgcg attgctgatc cccatgtgta tcactggcaa    3060
actgtgatgg acgacaccgt cagtgcgtcc gtcgcgcagg ctctcgatga gctgatgctt    3120
tgggccgagg actgccccga agtccggcac ctcgtgcacg cggatttcgg ctccaacaat    3180
gtcctgacgg acaatggccg cataacagcg gtcattgact ggagcgaggc gatgttcggg    3240
gattcccaat acgaggtcgc caacatcttc ttctggaggc cgtggttggc ttgtatggag    3300
cagcagacgc gctacttcga gcggaggcat ccggagcttg caggatcgcc gcggctccgg    3360
gcgtatatgc tccgcattgg tcttgaccaa ctctatcaga gcttggttga cggcaatttc    3420
gatgatgcag cttgggcgca gggtcgatgc gacgcaatcg tccgatccgg agccgggact    3480
gtcgggcgta cacaaatcgc ccgcagaagc gcggccgtct ggaccgatgg ctgtgtagaa    3540
gtactcgccg atagtggaaa ccgacgcccc agcactcgtc cgagggcaaa ggaatagcac    3600
gtgctacgag atttcgattc caccgccgcc ttctatgaaa ggttgggctt cggaatcgtt    3660
ttccgggacg ccggctggat gatcctccag cgcggggatc tcatgctgga gttcttcgcc    3720
```

```
caccccaact tgtttattgc agcttataat ggttacaaat aaagcaatag catcacaaat    3780
ttcacaaata aagcatttttt ttcactgcat tctagttgtg gtttgtccaa actcatcaat    3840
gtatcttatc atgtctgtat accgtcgacc tctagctaga gcttggcgta atcatggtca    3900
tagctgtttc ctgtgtgaaa ttgttatccg ctcacaattc cacacaacat acgagccgga    3960
agcataaagt gtaaagcctg ggtgcctaa tgagtgagct aactcacatt aattgcgttg    4020
cgctcactgc ccgctttcca gtcgggaaac ctgtcgtgcc agctgcatta atgaatcggc    4080
caacgcgcgg ggagaggcgg tttgcgtatt gggcgctctt ccgcttcctc gctcactgac    4140
tcgctgcgct cggtcgttcg gctgcggcga gcggtatcag ctcactcaaa ggcggtaata    4200
cggttatcca cagaatcagg ggataacgca ggaaagaaca tgtgagcaaa aggccagcaa    4260
aaggccagga accgtaaaaa ggccgcgttg ctggcgtttt tccataggct ccgcccccct    4320
gacgagcatc acaaaaatcg acgctcaagt cagaggtggc gaaacccgac aggactataa    4380
agataccagg cgtttccccc tggaagctcc ctcgtgcgct ctcctgttcc gaccctgccg    4440
cttaccggat acctgtccgc ctttctccct tcgggaagcg tggcgctttc tcatagctca    4500
cgctgtaggt atctcagttc ggtgtaggtc gttcgctcca agctgggctg tgtgcacgaa    4560
ccccccgttc agcccgaccg ctgcgcctta tccggtaact atcgtcttga gtccaacccg    4620
gtaagacacg acttatcgcc actggcagca gccactggta acaggattag cagagcgagg    4680
tatgtaggcg gtgctacaga gttcttgaag tggtggccta actacggcta cactagaaga    4740
acagtatttg gtatctgcgc tctgctgaag ccagttacct tcggaaaaag agttggtagc    4800
tcttgatccg gcaaacaaac caccgctggt agcggttttt tgtttgcaa gcagcagatt    4860
acgcgcagaa aaaaggatc tcaagaagat ccttttgatct tttctacggg gtctgacgct    4920
cagtggaacg aaaactcacg ttaagggatt ttggtcatga gattatcaaa aaggatcttc    4980
acctagatcc ttttaaatta aaaatgaagt tttaaatcaa tctaaagtat atatgagtaa    5040
acttggtctg acagttacca atgcttaatc agtgaggcac ctatctcagc gatctgtcta    5100
tttcgttcat ccatagttgc ctgactcccc gtcgtgtaga taactacgat acgggagggc    5160
ttaccatctg gccccagtgc tgcaatgata ccgcgagacc cacgctcacc ggctccagat    5220
ttatcagcaa taaaccagcc agccggaagg gccgagcgca gaagtggtcc tgcaacttta    5280
tccgcctcca tccagtctat taattgttgc cgggaagcta gagtaagtag ttcgccagtt    5340
aatagtttgc gcaacgttgt tgccattgct acaggcatcg tggtgtcacg ctcgtcgttt    5400
ggtatggctt cattcagctc cggttcccaa cgatcaaggc gagttacatg atcccccatg    5460
ttgtgcaaaa aagcggttag ctccttcggt cctccgatcg ttgtcagaag taagttggcc    5520
gcagtgttat cactcatggt tatggcagca ctgcataatt ctcttactgt catgccatcc    5580
gtaagatgct tttctgtgac tggtgagtac tcaaccaagt cattctgaga atagtgtatg    5640
cggcgaccga gttgctcttg cccggcgtca atacgggata ataccgcgcc acatagcaga    5700
actttaaaag tgctcatcat tggaaaacgt tcttcggggc gaaaactctc aaggatctta    5760
ccgctgttga gatccagttc gatgtaaccc actcgtgcac ccaactgatc ttcagcatct    5820
tttactttca ccagcgtttc tgggtgagca aaaacaggaa ggcaaaatgc cgcaaaaaag    5880
ggaataaggg cgacacggaa atgttgaata ctcatactct tcctttttca atattattga    5940
agcatttatc agggttattg tctcatgagc ggatacatat ttgaatgtat ttagaaaaat    6000
aaacaaatag gggttccgcg cacatttccc cgaaaagtgc cacctgacgt cagatcgacg    6060
gatcgggaga tcg                                                       6073
```

<210> SEQ ID NO 11
<211> LENGTH: 56
<212> TYPE: DNA
<213> ORGANISM: Artificial Sequence
<220> FEATURE:
<223> OTHER INFORMATION: Synthetic

<400> SEQUENCE: 11
ccacaggcgc gcactccgag gtccaactgc aggctagcac caagggccca tcggtc      56

<210> SEQ ID NO 12
<211> LENGTH: 32
<212> TYPE: DNA
<213> ORGANISM: Artificial Sequence
<220> FEATURE:
<223> OTHER INFORMATION: Synthetic

<400> SEQUENCE: 12
tgtgtgtcta gattatttac ccggggacag gg      32

<210> SEQ ID NO 13
<211> LENGTH: 40
<212> TYPE: DNA
<213> ORGANISM: Artificial Sequence
<220> FEATURE:
<223> OTHER INFORMATION: Synthetic

<400> SEQUENCE: 13
ccacaggcgc gcactccgaa gtgaagcttg aggagtctgg      40

<210> SEQ ID NO 14
<211> LENGTH: 33
<212> TYPE: DNA
<213> ORGANISM: Artificial Sequence
<220> FEATURE:
<223> OTHER INFORMATION: Synthetic

<400> SEQUENCE: 14
cttggtgcta gccgaagaga cagtgaccag agt      33

<210> SEQ ID NO 15
<211> LENGTH: 37
<212> TYPE: DNA
<213> ORGANISM: Artificial Sequence
<220> FEATURE:
<223> OTHER INFORMATION: Synthetic

<400> SEQUENCE: 15
ccacaggcgc gcactcccag ctccagatga cccagtc      37

<210> SEQ ID NO 16
<211> LENGTH: 35
<212> TYPE: DNA
<213> ORGANISM: Artificial Sequence
<220> FEATURE:
<223> OTHER INFORMATION: Synthetic

<400> SEQUENCE: 16
tctctctcta gattaacact ctcccctgtt gaagc      35

<210> SEQ ID NO 17
<211> LENGTH: 40
<212> TYPE: DNA
<213> ORGANISM: Artificial Sequence
<220> FEATURE:
<223> OTHER INFORMATION: Synthetic

<400> SEQUENCE: 17
ccacaggcgc gcactcccag gtacaactgc agcagtctgg                               40

<210> SEQ ID NO 18
<211> LENGTH: 35
<212> TYPE: DNA
<213> ORGANISM: Artificial Sequence
<220> FEATURE:
<223> OTHER INFORMATION: Synthetic

<400> SEQUENCE: 18
cttggtgcta gcagaggaaa cggtgaccgt ggtcc                                    35

<210> SEQ ID NO 19
<211> LENGTH: 37
<212> TYPE: DNA
<213> ORGANISM: Artificial Sequence
<220> FEATURE:
<223> OTHER INFORMATION: Synthetic

<400> SEQUENCE: 19
ccacaggcgc gcactcccga catccagctg cccagtc                                  37

<210> SEQ ID NO 20
<211> LENGTH: 39
<212> TYPE: DNA
<213> ORGANISM: Artificial Sequence
<220> FEATURE:
<223> OTHER INFORMATION: Synthetic

<400> SEQUENCE: 20
agccaccgta cgtttgatct ccaattttgt cccccgagc                                39

<210> SEQ ID NO 21
<211> LENGTH: 33
<212> TYPE: DNA
<213> ORGANISM: Artificial Sequence
<220> FEATURE:
<223> OTHER INFORMATION: Synthetic

<400> SEQUENCE: 21
ccgcttccat ggtagacaac aaattcaaca aag                                      33

<210> SEQ ID NO 22
<211> LENGTH: 39
<212> TYPE: DNA
<213> ORGANISM: Artificial Sequence
<220> FEATURE:
<223> OTHER INFORMATION: Synthetic

<400> SEQUENCE: 22
gggtttagcg gccgctttcg gcgcctgagc atcatttag                                39

<210> SEQ ID NO 23
<211> LENGTH: 345
<212> TYPE: PRT
<213> ORGANISM: Artificial Sequence
<220> FEATURE:
<223> OTHER INFORMATION: Synthetic

<400> SEQUENCE: 23

Gly Gly Ser Leu Ala Ala Leu Thr Ala His Gln Ala Cys His Leu Pro
1               5                   10                  15

Leu Glu Thr Phe Thr Arg His Arg Gln Pro Arg Gly Trp Glu Gln Leu
            20                  25                  30

Glu Gln Cys Gly Tyr Pro Val Gln Arg Leu Val Ala Leu Tyr Leu Ala
            35                  40                  45

Ala Arg Leu Ser Trp Asn Gln Val Asp Gln Val Ile Arg Asn Ala Leu
 50                  55                  60

Ala Ser Pro Gly Ser Gly Gly Asp Leu Gly Glu Ala Ile Arg Glu Gln
 65                  70                  75                  80

Pro Glu Gln Ala Arg Leu Ala Leu Thr Leu Ala Ala Glu Ser Glu
                85                  90                  95

Arg Phe Val Arg Gln Gly Thr Gly Asn Asp Glu Ala Gly Ala Ala Asn
                100                 105                 110

Gly Pro Ala Asp Ser Gly Asp Ala Leu Leu Glu Arg Asn Tyr Pro Thr
            115                 120                 125

Gly Ala Glu Phe Leu Gly Asp Gly Gly Asp Val Ser Phe Ser Thr Arg
            130                 135                 140

Gly Thr Gln Asn Trp Thr Val Glu Arg Leu Leu Gln Ala His Arg Gln
145                 150                 155                 160

Leu Glu Glu Arg Gly Tyr Val Phe Val Gly Tyr His Gly Thr Phe Leu
                165                 170                 175

Glu Ala Ala Gln Ser Ile Val Phe Gly Val Arg Ala Arg Ser Gln
            180                 185                 190

Asp Leu Asp Ala Ile Trp Arg Gly Phe Tyr Ile Ala Gly Asp Pro Ala
            195                 200                 205

Leu Ala Tyr Gly Tyr Ala Gln Asp Gln Glu Pro Asp Ala Arg Gly Arg
            210                 215                 220

Ile Arg Asn Gly Ala Leu Leu Arg Val Tyr Val Pro Arg Ser Ser Leu
225                 230                 235                 240

Pro Gly Phe Tyr Arg Thr Ser Leu Thr Leu Ala Ala Pro Glu Ala Ala
                245                 250                 255

Gly Glu Val Glu Arg Leu Ile Gly His Pro Leu Pro Leu Arg Leu Asp
            260                 265                 270

Ala Ile Thr Gly Pro Glu Glu Gly Gly Arg Leu Glu Thr Ile Leu
            275                 280                 285

Gly Trp Pro Leu Ala Glu Arg Thr Val Val Ile Pro Ser Ala Ile Pro
290                 295                 300

Thr Asp Pro Arg Asn Val Gly Gly Asp Leu Asp Pro Ser Ser Ile Pro
305                 310                 315                 320

Asp Lys Glu Gln Ala Ile Ser Ala Leu Pro Asp Tyr Ala Ser Gln Pro
                325                 330                 335

Gly Lys Pro Pro Arg Lys Asp Glu Leu
            340                 345

<210> SEQ ID NO 24
<211> LENGTH: 345
<212> TYPE: PRT
<213> ORGANISM: Artificial Sequence
<220> FEATURE:
<223> OTHER INFORMATION: Synthetic

<400> SEQUENCE: 24

Gly Gly Ser Leu Ala Ala Leu Thr Ala His Gln Ala Cys His Leu Pro
1               5                   10                  15

Leu Glu Thr Phe Thr Arg His Arg Gln Pro Arg Gly Trp Glu Gln Leu
                20                  25                  30

Glu Gln Cys Gly Tyr Pro Val Gln Arg Leu Val Ala Leu Tyr Leu Ala
            35                  40                  45

Ala Arg Leu Ser Trp Asn Gln Val Asp Gln Val Ile Arg Asn Ala Leu
    50                  55                  60

Ala Ser Pro Gly Ser Gly Asp Leu Gly Glu Ala Ile Arg Glu Gln
65                  70                  75                  80

Pro Glu Gln Ala Arg Leu Ala Leu Thr Leu Ala Ala Glu Ser Glu
                85                  90                  95

Arg Phe Val Arg Gln Gly Thr Gly Asn Asp Glu Ala Gly Ala Ala Asn
                100                 105                 110

Gly Pro Ala Asp Ser Gly Asp Ala Leu Leu Glu Arg Asn Tyr Pro Thr
            115                 120                 125

Gly Ala Glu Phe Leu Gly Asp Gly Asp Val Ser Phe Ser Thr Arg
    130                 135                 140

Gly Thr Gln Asn Trp Thr Val Glu Arg Leu Leu Gln Ala His Arg Gln
145                 150                 155                 160

Leu Glu Glu Arg Gly Tyr Val Phe Val Gly Tyr His Gly Thr Phe Leu
                165                 170                 175

Glu Ala Ala Gln Ser Ile Val Phe Gly Val Arg Ala Arg Ser Gln
            180                 185                 190

Asp Leu Asp Ala Ile Trp Arg Gly Phe Tyr Ile Ala Gly Asp Pro Ala
                195                 200                 205

Leu Ala Tyr Gly Tyr Ala Gln Asp Gln Glu Pro Asp Ala Arg Gly Arg
    210                 215                 220

Ile Arg Asn Gly Ala Leu Leu Arg Val Tyr Val Pro Arg Ser Ser Leu
225                 230                 235                 240

Pro Gly Phe Tyr Arg Thr Ser Leu Thr Leu Ala Ala Pro Glu Ala Ala
                245                 250                 255

Gly Glu Val Glu Arg Leu Ile Gly His Pro Leu Pro Leu Arg Leu Asp
            260                 265                 270

Ala Ile Thr Gly Pro Glu Glu Gly Gly Arg Leu Glu Thr Ile Leu
    275                 280                 285

Gly Trp Pro Leu Ala Glu Arg Thr Val Val Ile Pro Ser Ala Ile Pro
290                 295                 300

Thr Asp Pro Arg Asn Val Gly Gly Asp Leu Asp Pro Ser Ser Ile Pro
305                 310                 315                 320

Asp Lys Glu Gln Ala Ile Ser Ala Leu Pro Asp Tyr Ala Ser Gln Pro
                325                 330                 335

Gly Lys Pro Pro Arg Arg Asp Glu Leu
            340                 345

<210> SEQ ID NO 25
<211> LENGTH: 334
<212> TYPE: PRT
<213> ORGANISM: Artificial Sequence
<220> FEATURE:
<223> OTHER INFORMATION: Synthetic

<400> SEQUENCE: 25

Met Trp Glu Gln Leu Glu Gln Ser Gly Tyr Pro Val Gln Arg Leu Val
1               5                   10                  15

Ala Leu Tyr Leu Ala Ala Arg Leu Ser Trp Asn Gln Val Asp Gln Val
                20                  25                  30

Ile Arg Asn Ala Leu Ala Ser Pro Gly Ser Gly Gly Asp Leu Gly Glu
            35                  40                  45

Ala Ile Arg Glu Gln Pro Glu Gln Ala Arg Leu Ala Leu Thr Leu Ala
    50                  55                  60

Ala Ala Glu Ser Glu Arg Phe Val Arg Gln Gly Thr Gly Asn Asp Glu

```
                65                  70                  75                  80
Ala Gly Ala Ala Asn Ala Asp Val Val Ser Leu Thr Cys Pro Val Ala
                    85                  90                  95

Ala Gly Glu Cys Ala Gly Pro Ala Asp Ser Gly Asp Ala Leu Leu Glu
                    100                 105                 110

Arg Asn Tyr Pro Thr Gly Ala Glu Phe Leu Gly Asp Gly Gly Asp Val
                    115                 120                 125

Ser Phe Ser Thr Arg Gly Thr Gln Asn Trp Thr Val Glu Arg Leu Leu
                    130                 135                 140

Gln Ala His Arg Gln Leu Glu Glu Arg Gly Tyr Val Phe Val Gly Tyr
145                 150                 155                 160

His Gly Thr Phe Leu Glu Ala Ala Gln Ser Ile Val Phe Gly Gly Val
                    165                 170                 175

Arg Ala Arg Ser Gln Asp Leu Asp Ala Ile Trp Arg Gly Phe Tyr Ile
                    180                 185                 190

Ala Gly Asp Pro Ala Leu Ala Tyr Gly Tyr Ala Gln Asp Gln Glu Pro
                    195                 200                 205

Asp Ala Arg Gly Arg Ile Arg Asn Gly Ala Leu Leu Arg Val Tyr Val
                    210                 215                 220

Pro Arg Ser Ser Leu Pro Gly Phe Tyr Arg Thr Ser Leu Thr Leu Ala
225                 230                 235                 240

Ala Pro Glu Ala Ala Gly Glu Val Glu Arg Leu Ile Gly His Pro Leu
                    245                 250                 255

Pro Leu Arg Leu Asp Ala Ile Thr Gly Pro Glu Glu Gly Gly Arg
                    260                 265                 270

Leu Glu Thr Ile Leu Gly Trp Pro Leu Ala Glu Arg Thr Val Val Ile
                    275                 280                 285

Pro Ser Ala Ile Pro Thr Asp Pro Arg Asn Val Gly Gly Asp Leu Asp
                    290                 295                 300

Pro Ser Ser Ile Pro Asp Lys Glu Gln Ala Ile Ser Ala Leu Pro Asp
305                 310                 315                 320

Tyr Ala Ser Gln Pro Gly Lys Pro Pro Arg Glu Asp Leu Lys
                    325                 330

<210> SEQ ID NO 26
<211> LENGTH: 361
<212> TYPE: PRT
<213> ORGANISM: Artificial Sequence
<220> FEATURE:
<223> OTHER INFORMATION: Synthetic

<400> SEQUENCE: 26

Gly Gly Ser Leu Ala Ala Leu Thr Ala His Gln Ala Cys His Leu Pro
1               5                   10                  15

Leu Glu Thr Phe Thr Arg His Arg Gln Pro Arg Gly Trp Glu Gln Leu
                20                  25                  30

Glu Gln Cys Gly Tyr Pro Val Gln Arg Leu Val Ala Leu Tyr Leu Ala
                35                  40                  45

Ala Arg Leu Ser Trp Asn Gln Val Asp Gln Val Ile Arg Asn Ala Leu
                50                  55                  60

Ala Ser Pro Gly Ser Gly Gly Asp Leu Gly Glu Ala Ile Arg Glu Gln
65                  70                  75                  80

Pro Glu Gln Ala Arg Leu Ala Leu Thr Leu Ala Ala Ala Glu Ser Glu
                85                  90                  95

Arg Phe Val Arg Gln Gly Thr Gly Asn Asp Glu Ala Gly Ala Ala Asn
                100                 105                 110
```

-continued

```
Ala Asp Val Val Ser Leu Thr Cys Pro Val Ala Ala Gly Glu Cys Ala
            115                 120                 125

Gly Pro Ala Asp Ser Gly Asp Ala Leu Leu Glu Arg Asn Tyr Pro Thr
    130                 135                 140

Gly Ala Glu Phe Leu Gly Asp Gly Gly Asp Val Ser Phe Ser Thr Arg
145                 150                 155                 160

Gly Thr Gln Asn Trp Thr Val Glu Arg Leu Leu Gln Ala His Arg Gln
                165                 170                 175

Leu Glu Glu Arg Gly Tyr Val Phe Val Gly Tyr His Gly Thr Phe Leu
            180                 185                 190

Glu Ala Ala Gln Ser Ile Val Phe Gly Gly Val Arg Ala Arg Ser Gln
            195                 200                 205

Asp Leu Asp Ala Ile Trp Arg Gly Phe Tyr Ile Ala Gly Asp Pro Ala
            210                 215                 220

Leu Ala Tyr Gly Tyr Ala Gln Asp Gln Glu Pro Asp Ala Arg Gly Arg
225                 230                 235                 240

Ile Arg Asn Gly Ala Leu Leu Arg Val Tyr Val Pro Arg Ser Ser Leu
                245                 250                 255

Pro Gly Phe Tyr Arg Thr Ser Leu Thr Leu Ala Ala Pro Glu Ala Ala
                260                 265                 270

Gly Glu Val Glu Arg Leu Ile Gly His Pro Leu Pro Leu Arg Leu Asp
            275                 280                 285

Ala Ile Thr Gly Pro Glu Glu Glu Gly Gly Arg Leu Glu Thr Ile Leu
            290                 295                 300

Gly Trp Pro Leu Ala Glu Arg Thr Val Val Ile Pro Ser Ala Ile Pro
305                 310                 315                 320

Thr Asp Pro Arg Asn Val Gly Gly Asp Leu Asp Pro Ser Ser Ile Pro
                325                 330                 335

Asp Lys Glu Gln Ala Ile Ser Ala Leu Pro Asp Tyr Ala Ser Gln Pro
            340                 345                 350

Gly Lys Pro Pro Arg Glu Asp Leu Lys
            355                 360

<210> SEQ ID NO 27
<211> LENGTH: 8
<212> TYPE: PRT
<213> ORGANISM: Artificial Sequence
<220> FEATURE:
<223> OTHER INFORMATION: Synthetic

<400> SEQUENCE: 27

Ala Ala Ala Ser Gly Gly Pro Glu
1               5
```